(12) United States Patent
Penichet et al.

(10) Patent No.: US 7,736,652 B2
(45) Date of Patent: Jun. 15, 2010

(54) ANTIBODY FUSION PROTEINS: EFFECTIVE ADJUVANTS OF PROTEIN VACCINATION

(75) Inventors: Manuel L. Penichet, Los Angeles, CA (US); Jay Dela Cruz, Inglewood, CA (US); Lisan Peng, Tuscon, AZ (US); Sherie L. Morrison, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 144 days.

(21) Appl. No.: 10/118,473

(22) Filed: Apr. 5, 2002

(65) Prior Publication Data
US 2003/0187225 A1    Oct. 2, 2003

Related U.S. Application Data

(60) Provisional application No. 60/366,917, filed on Mar. 21, 2002.

(51) Int. Cl.
*A61K 39/44* (2006.01)
*A61K 39/395* (2006.01)
*C12P 21/08* (2006.01)
*C12N 5/08* (2006.01)

(52) U.S. Cl. .............. 424/178.1; 424/134.1; 424/156.1; 424/277.1; 435/372; 530/387.3

(58) Field of Classification Search .................. 435/69.1
See application file for complete search history.

(56) References Cited

U.S. PATENT DOCUMENTS 5,650,150 A    7/1997  Gillies
5,977,322 A   11/1999  Marks et al.
6,194,177 B1   2/2001  Campbell et al.
6,617,135 B1   9/2003  Gillies et al.
2004/0057969 A1  3/2004  Smith et al.

FOREIGN PATENT DOCUMENTS

WO    WO 97/30089    *  8/1997

OTHER PUBLICATIONS

Lustgarten et al, Jan. 1, 1999. The Journal of Immunology. 162(1):359-65.*
Wu, 2002. Clinica Chimica Acta. 322: 11-19.*
Lode et al, 2000. Drugs Today (Barc). 36(5): 321-336.*
Bulfone-Paus et al (1998. Cancer Research. 58: 2707-2710).*
Helguera et al, 2002, Clinical Immunology, 105(3): 233-246.*
Dela Cruz et al, 2005, Vaccine 23: 4793-4803.*
Wells (Sep. 18, 1990) Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*

(Continued)

*Primary Examiner*—Bridget E Bunner
*Assistant Examiner*—Zachary C Howard
(74) *Attorney, Agent, or Firm*—Quine Intellectual Property Law Group, P.C.; Paul Littlepage

(57) ABSTRACT

The present invention provides methods of use of various antibody-immunostimulant fusion proteins as adjuvants of antigenic protein vaccinations to elicit humoral and/or cellular immune responses in vaccinated subjects. Compositions which include these fusion proteins and innate and/or exogenous antigenic proteins are also provided.

19 Claims, 10 Drawing Sheets

OTHER PUBLICATIONS

Bork (2000) Genome Research 10:398.*
Skolnick and Fetrow (2000) Trends in Biotech. 18(1): 34.*
Doerks et al. (Jun. 1998) Trends in Genetics 14(6): 248.*
Smith and Zhang (Nov. 1997) Nature Biotechnology 15:1222.*
Brenner (Apr. 1999) Trends in Genetics 15(4): 132.*
Bork and Bairoch (Oct. 1996) Trends in Genetics 12(10): 425.*
Larregina et al (1997. Immunology. 91: 303-313).*
Dela Cruz et al (2006; Molecular Immunology; 43: 667-676).*
Braun and Pantel (1998) "Prognostic significance of micrometastatic bone marrow involvement," *Breast Cancer Research and Treatment*, 52:201-216.
Bowie et al. (1990) "Deciphering the message in protein sequences: tolerance to amino acids substitutions," *Science*, 247:1306-1310.
Ngo et al. (1994) "Computational complexity, protein structure prediction, and the Levinthal paradox," *The Protein Folding Problem and Tertiary Structure Prediction*, Merz et al., eds, Birkhauser, Boston, p. 433-506.
Pawelec (2004) "Tumour escape: antitumor effectors too much of a good thing?" *Cancer Immuunol. Imminother.*, 53:262-274.
Penichet et al. (1997) "Antibody-IL-2 fusion proteins: a novel strategy for immune potentiation," *Human Antibodies*, 8(3):106-118.
Anselmino, et al., 1989 "Human basophils selectively express the Fc gamma RII (CDw32) subtype of IgG receptor" *J Allergy Clin Immunol* 84:907-914.
Arai, et al., 1990 "Cytokines: coordinators of immune and inflammatory responses" *Annu Rev Biochem* 59:783-836.
Baselga, et al., 1996 "Phase II study of weekly intravenous recombinant humanized anti-p185HER2 monoclonal antibody in patients with HER2/neu-overexpressing metastatic breast cancer" *J Clin Oncol* 14:737-744.
Becker et al., 1996 "An antibody-interleukin 2 fusion protein overcomes tumor heterogeneity by induction of a cellular immune response" Proc Natl Acad Sci USA 93:7826-7831.
Becker et al., 1996 "Long-lived and transferable tumor immunity in mice after targeted interleukin-2 therapy" J Clin Invest 98:2801-4.
Becker et al., 1996 "T cell-mediated eradication of murine metastatic melanoma induced by targeted interleukin 2 therapy" J Exp Med 183:2361-6.
Boyle, 1990, in Bacterial Immunoglobulin-Binding Proteins, ed. Boyle, M.P.D. (Academic, San Diego), vol. 1, pp. 17-28.
Brossart, P., et al., 2000 "Induction of cytotoxic T-lymphocyte responses in vivo after vaccinations with peptide-pulsed dendritic cells" *Blood* 96:3102.
Buckle, et al., 1989 "The effect of IFN-gamma and colony-stimulating factors on the expression of neutrophil cell membrane receptors" *J Immunol* 143:2295-2301.
Chen et al, 1998 "DNA vaccines encoding full-length or truncated Neu induce protective immunity against Neu-expressing mammary tumors" Cancer Res 58:1965-1971.
Chen, et al., 1995 "Monocyte-mediated lysis of acute myeloid leukemia cells in the presence of the bispecific antibody 251 x 22 (anti-CD33 x antiCD64)" *Clin Cancer Res* 1:1319-1325.
Colombo et al. 1992 "Local Cytokine Availability Elicicts Tumor Rejection and Systemic Immunity through Granulocyte-T-Lymphocyte Cross-Talk," *Cancer Res* 52:4853-4857.
Dela Cruz et al., 2000 "Recombinant anti-human HER2/neu IgG3-(GMCSF) fusion protein retains antigen specificity, cytokine function and demonstrates anti-tumor activity" *J Immunol* 165:5112-21.
Disis 1999, "Generation of immunity to the HER-2/neu oncogenic protein in patients with breast and ovarian cancer using a peptide-based vaccine" *Clin Cancer Res* 5:1289-1297.
Disis, et al 2001 "Clinical translation of peptide-based vaccine trials: the HER-2/neu model" *Crit Rev Immunol* 21:263-273.
Disis, et al. 1996 "Peptide-based, but not whole protein, vaccines elicit immunity to HER-2/neu, oncogenic self-protein" *J Immunol* 156:3151-3158.
Disis, et al., 1998 "HER-2/neu oncogenic protein: issues in vaccine development", *Crit Rev Immunol* 18:37-45.
Disis, M. L., et al., 2001 "Cancer vaccines targeting the HER2/*neu* oncogenic protein" *Semin Oncol* 28:12-20.

Foy, et al. 2001 "Vaccination with Her-2/neu DNA or protein subunits protects against growth of a Her-2/neu-expressing murine tumor" *Vaccine* 19:2598-2606.
Graille M., et al. 2000, "Crystal structure of a *Staphylococcus aureus* protein A domain complexed with the Fab fragment of a human IgM antibody: structural basis for recognition of B-cell receptors and superantigen activity" *Proc Natl Acad Sci USA* 97: 5399-5404.
Hartnell, et al., 1992 "IFN-gamma induces expression of Fc gamma RIII (CD16) on human eosinophils" *J Immunol* 148:1471-1478.
Harvill et al., 1996 "In vivo properties of an IgG3-II-2 fusion protein. A general strategy for immune potentiation" *J Immunol* 157:3165-70.
Hillson et al., 1993 "The structural basis of germline-encoded $V_H3$ immunoglobulin binding to staphylococcal protein A" *J Exp Med* 178:331-6.
Hiltbold et al., 2000, "The mechanism of unresponsiveness to circulating tumor antigen MUC1 is a block in intracellular sorting and processing by dendritic cells" *J Immunol* 165:3730-41.
Hornick et al., 1997 "Chimeric CLL-1 antibody fusion proteins containing granulocyte-macrophage colony-stimulating factor or interleukin-2 with specificity for B-cell malignancies exhibit enhanced effector functions while retaining tumor targeting properties" *Blood* 89:4437.
Johnson, et al. "Superantigens in human disease" *Scientific American* Apr. 1992, p. 92-101.
Klebanoff, et al., 1992 "Effects of gamma-interferon on human neutrophils: protection from deterioration on storage" *Blood* 80:225-234.
Lachman, et al. 2001 "DNA vaccination against neu reduces breast cancer incidence and metastasis in mice" *Cancer Gene Ther* 8:259-268.
Liu et al., 1998 "Treatment of B-cell lymphoma with chimeric IgG and single-chain Fv antibody-interleukin-2 fusion proteins" *Blood* 92:2103-2112.
Meininger et al. 2000 "Characterization of the binding interface between the E-domain of Staphylococcal protein A and an antibody Fv-fragment" *Biochemistry* 39: 26-36.
Mire-Sluis, 1993 "Cytokines and disease," *TIBTECH* 11:74-77.
Murray, et al., 2000 "Clinical trials of HER-2/neu-specific vaccines" *Semin Oncol* 27:71-75.
Nagata, et al. 1997 "Peptides derived from a wild-type murine proto-oncogene c-erbB-2? HER2/*neu* can induce CTL and tumor suppression in syngeneic hosts" *J Immunol* 159:1336.
Peng et al., 1999, "A single-chain IL-12 IgG3 antibody fusion protein retains antibody specificity and IL-12 bioactivity and demonstrates antitumor activity" *J Immunol* 163:250-8.
Penichet et al., 1998 "An IgG3-IL-2 fusion protein recognizing a murine B cell lymphoma exhibits effective tumor imaging and anti-tumor activity" *J Interferon Cytokine Res* 18:597-607.
Penichet et al., 2001 "Antibody-cytokine fusion proteins for the therapy of cancer" *J Immunol Methods* 248:91-101.
Penichet et al., 2001, "A recombinant IgG3-(IL-2) fusion protein for the treatment of human HER2/neu expressing tumors" *Human Antibodies* 10:43-49.
Penichet, et al. 1999 "In vivo properties of three human HER2/neu-expresing murine cell lines in immunocompetent mice" *Lab Anim Sci* 49:179-188.
Pupa, et al. "Prevention of spontaneous neu-expressing mammary tumor development in mice transgenic for rat proto-neu by DNA vaccination" *Gene Ther* 8:75-79, Date: 2001.
Rodolfo, et al., 1998 "IgG2a induced by interleukin (IL) 12-producing tumor cell vaccines but not IgG1 induced by IL-4 vaccine is associated with the eradication of experimental metastases" *Cancer Res* 58:5812-5817.
Rovero, et al. 2000 "DNA vaccination against rat her-2/Neu p185 more effectively inhibits carcinogenesis than transplantable carcinomas in transgenic BALB/c mice" *J Immunol* 165:5133-5142.
Sekaly, R. (ed.) "Bacterial Superantigens" *Seminars in Immunol.* vol. 5, 1993, p. 1-2.
Shiku, et al. 2000 "Development of a cancer vaccine: peptides, proteins, and DNA" *Cancer Chemother Pharmacol* 46:S77-82.

Su, et al., 2002 "IL-12 is required for antibody-mediated protective immunity against blood-stage *Plasmodium chabaudi* AS malaria infection in mice" *J Immunol* 168:1348-1355.

Tashiro M., et al. 1995, "Structures of bacterial immunoglobulin-binding domains and their complexes with immunoglobulins" *Curr Opin Struct Biol* 4: 471-81.

Taub, 1996 "Chemokine-Leukocyte Interactions. The Voodoo That They Do So Well" *Cytokine Growth Factor Rev* 7:355-376.

Taylor, et al., 1996 "Humoral and cellular responses raised against the human HER2 oncoprotein are cross-reactive with the homologous product of the new proto-oncogene, but do not protect rats against B104 tumors expressing mutated neu" *Cancer Immunol Immunother* 42:179-184.

Taylor, et al., 1998 "Manipulation of the immune response of mice against neu/HER2-expressing tumours" *Oncol Rep* 5:1535-1539.

teVelde, et al., 1992 "IL-10 stimulates monocyte Fc gamma R surface expression and cytotoxic activity. Distinct regulation of antibody-dependent cellular cytotoxicity by IFN-gamma, IL-4, and IL-10" *J Immunol* 149:4048-4052.

Vaickus, et al., 1990 "Interferon gamma augments Lym-1-dependent, granulocyte-mediated tumor cell lysis" *Blood* 75:2408-2416.

Vidal M. A., et al. 1985 "Alternative mechanism of protein A-immunoglobulin interaction the $V_H$-associated reactivity of a monoclonal human IgM" *J Immunol* 135:1232-8.

Xiang et al., 1997 "Elimination of established murine colon carcinoma metastases by antibody-interleukin 2 fusion protein therapy" *Cancer Res* 57:4948-55.

Xiang et al., 1999 "T cell memory against colon carcinoma is long-lived in the absence of antigen" *J Immunol* 163:3676-83.

Yip, et al., 2001 "Identification of epitope regions recognized by tumor inhibitory and stimulatory anti-ErbB-2 monoclonal antibodies: implications for vaccine design" *J Immunol* 166:5271.

\* cited by examiner

ANTIBODY FUSION PROTEINS: EFFECTIVE ADJUVANTS OF PROTEIN VACCINATION

CROSS-REFERENCES TO RELATED APPLICATIONS

Pursuant to 35 USC §119(e), this application claims priority to and benefit of U.S. Provisional Patent Application Ser. No. 60/366,917, filed on Mar. 21, 2002, the disclosure of which is incorporated herein in its entirety for all purposes.

STATEMENT AS TO RIGHTS TO INVENTIONS MADE UNDER FEDERALLY SPONSORED RESEARCH AND DEVELOPMENT

This invention was made with Government support under Grant Nos. CA86915 & DAMD17-99-1-9098, awarded by the National Institutes of Health and Army. The Government has certain rights in this invention.

BACKGROUND OF THE INVENTION

Despite considerable advancement in the therapy of various tumors and cancers, residual disease is still a major problem in the clinical management of these conditions. Additionally, treatment and especially prevention of infectious diseases remains a continuing concern due to, e.g., spread of viral diseases such as HIV and emergence of treatment-resistant variants of more well known diseases such as tuberculosis, *staphylococcus* infection, etc.

In the case of tumor treatment, chemotherapeutic strategies are necessarily limited by severe toxicities, and are of limited efficacy against non-proliferating tumor cells. Therefore, new methods emphasizing non-chemotherapeutic approaches are desired. For example, treatment of patients with advanced HER2/neu expressing tumors (e.g., breast cancers) through use of a humanized anti-HER2/neu monoclonal antibody, Trastuzumab (previously known as rhuMAb HER2), directed at the extracellular domain of HER2/neu can lead to a measurable response in some patients with tumors that overexpress the HER2/neu oncoprotein. However, only a subset of patients treated with Trastuzumab show an objective response, and although a combination of Trastuzumab with chemotherapy enhances its anti-tumor activity, still not all patients respond positively. Furthermore, even more desirous than an effective treatment for such tumors would be an effective prevention of them (e.g., especially in individuals with a family history of particular cancers).

Previously, antibody-(IL-2) fusion proteins have been the best characterized and most broadly used in successful anti-tumor experiments using animal models (see, e.g., Penichet and Morrison, 2001, "Antibody-cytokine fusion proteins for the therapy of cancer" *J Immunol Met* 248:91-101). Numerous studies have explored various combinations of antibodies and, e.g., IL-2, as direct targeting agents of tumor cells. For example, a tumor specific antibody-(IL-2) fusion protein was previously developed by the inventors, and comprised a human IgG3 specific for the idiotype (Id) of the Ig expressed on the surface of the B cell lymphoma 38C13 with human IL-2 fused at the end of the $C_H3$ domain. See, Penichet et al., 1998 "An IgG3-IL-2 fusion protein recognizing a murine B cell lymphoma exhibits effective tumor imaging and antitumor activity" *J Interferon Cytokine Res* 18:597-607. That antibody fusion protein, IgG3-$C_H3$-(IL-2), was expressed in Sp2/0 and was properly assembled and secreted. Anti-Id IgG3-$C_H3$-(IL-2) has a half-life in mice of approximately 8 hours, which is 17-fold longer than the half-life reported for IL-2 (i.e., when not fused to another domain), and it showed a better localization of subcutaneous tumors in mice than the anti-Id IgG3 by itself. Most importantly, the anti-Id IgG3-$C_H3$-(IL-2) showed enhanced anti-tumor activity compared to the combination of antibody and IL-2 administered together. Again, see, Penichet et al., 1998, supra. Additionally, a chimeric anti-Id IgG1-(IL-2) fusion protein (chS5A8-IL-2) expressed in P3X63Ag8.653 has shown more effectiveness in the in vivo eradication of the 38C13 tumor than the combination of the anti-Id antibody and IL-2 or an antibody-(IL-2) fusion protein with an irrelevant specificity. See, Liu et al., 1998 "Treatment of B-cell lymphoma with chimeric IgG and single-chain Fv antibody-interleukin-2 fusion proteins" *Blood* 92:21030-12.

Another example of previous antibody fusion proteins in cancer treatment involved chimeric anti-$GD_2$ IgG1-(IL-2) fusion protein (ch14.18-IL-2) produced in Sp2/0 cells. See, Becker et al., 1996 "T cell-mediated eradication of murine metastatic melanoma induced by targeted interleukin 2 therapy" *J Exp Med* 183:2361-6; Becker et al., 1996 "An antibody-interleukin 2 fusion protein overcomes tumor heterogeneity by induction of a cellular immune response" *Proc Natl Acad Sci USA* 93:7826-31; and Becker et al., 1996 "Long-lived and transferable tumor immunity in mice after targeted interleukin-2 therapy" *J Clin Invest* 98:2801-4. The ch14.18-IL-2 treatment of mice which had pulmonary and hepatic metastases, as well as subcutaneous $GD_2$ expressing B16 melanoma, resulted in a specific and strong anti-tumor activity. This anti-tumor activity was significant compared to antibody (ch14.18) and IL-2 or irrelevant antibody-(IL-2) fusion proteins and resulted in the complete eradication of the tumor in a number of animals. See, Becker references, supra. Similar results have been obtained in mice bearing CT26-KSA hepatic and pulmonary metastases and treated with a humanized anti-KSA antibody-IL-2 fusion protein (huKS1/4-IL-2) produced in NS0. See, Xiang et al., 1997 "Elimination of established murine colon carcinoma metastases by antibody-interleukin 2 fusion protein therapy" *Cancer Res* 57:4948-55 and Xiang et al., 1999 "T cell memory against colon carcinoma is long-lived in the absence of antigen" *J Immunol* 163:3676-83.

Other examples of antibody fusion molecules include a chimeric anti-human MHC class II IgG1 fused to GMCSF (chCLL-1/GMCSF) expressed in NS0 (see, Hornick et al., 1997 "Chimeric CLL-1 antibody fusion proteins containing granulocyte-macrophage colony-stimulating factor or interleukin-2 with specificity for B-cell malignancies exhibit enhanced effector functions while retaining tumor targeting properties" *Blood* 89:4437-47) and a humanized anti-HER2/neu IgG3 fused to IL-12 (see, Peng et al., 1999, "A single-chain IL-12 IgG3 antibody fusion protein retains antibody specificity and IL-12 bioactivity and demonstrates antitumor activity" *J Immunol* 163:250-8), IL-2 (see, Penichet et al., 2001, "A recombinant IgG3-(IL-2) fusion protein for the treatment of human HER2/neu expressing tumors" *Human Antibodies* 10:43-49) and GMCSF expressed in P3X63Ag8.653 (see, Dela Cruz et al., 2000, "Recombinant anti-human HER2/neu IgG3-(GMCSF) fusion protein retains antigen specificity, cytokine function and demonstrates anti-tumor activity" *J Immunol* 165:5112-21).

In all of the above work, it is important to note that the antibody-cytokine fusion proteins containing IL-2, IL-12, or GMCSF, etc. have been used as direct antitumor agents which directly targeted tumors in animal models. The antibody fusion proteins bound to antigens on tumor surfaces, thus increasing the local concentration of, e.g., Il-2, etc. around the tumor. The increased, e.g., IL-2, thus lead to anti-tumor activity in some cases. See, e.g., Penichet, et al. 2001, supra.

Additionally, some prior work by the inventors described linking antigens to IL-2 via an IgG3-(IL-2) fusion protein with affinity for a convenient hapten antigen, dansyl (DNS). See, Harvill et al., 1996 "In vivo properties of an IgG3-Il-2 fusion protein. A general strategy for immune potentiation" *J Immunol* 147:3165-70. The antigen used in this work was highly artificial (bovine serum albumin) rather than a disease-related antigen. Using hapten-conjugated-bovine serum albumin (DNS-BSA) as a model antigen the inventors showed an antibody response elicited by anti-DNS-IgG3-(IL-2)-bound DNS-BSA injected into mice increased over that of DNS-BSA-Sepharose, anti-DNS-IgG3-bound DNS-BSA, or a non-specific IgG3-(IL-2)-bound DNS-BSA. Although, the binding of the antibody-(IL-2) fusion protein to the antigen (non-covalent physical linkage) was shown to enhance the immune response (see, Harvill et al., 1996, supra), only one antibody fusion protein (antibody-(IL-2) fusion protein was used and the study was restricted to the characterization of the humoral (antibody) immune response. Also, unfortunately, use of the dansyl group may create a low level of stability between the antigens and the antibodies. Such instability could be problematic in proper immune stimulation treatments in vivo. Additionally, the use of dansyl, entails the possibility that the dansyl groups could mask or alter specific epitopes on the antigen it is linked to, thus, interfering with proper immune response stimulation in subjects.

In the case of infectious diseases, numerous bacteria (such as *Staphylococcus aureus*), viruses, mycoplasms, fungi, parasites, etc. present a serious problem. For example, the bacteria *Staphylococcus aureus* is a common cause of hospital-acquired infections that result in high mortality. *Staphylococcus aureus* can cause, e.g., pneumonia, endocarditis, osteomyelitis, septic arthritis, postoperative wound infections, septicemia, toxic shock, etc. Unfortunately, many bacterium, including many strains of *Staphylococcus aureus*, are resistant to first-line drugs such as synthetic penicillins (e.g., methicillin). Other bacteria, including some strains of *Staphylococcus aureus*, are resistant to multiple drugs, including the so-called antibiotic of last resort, vancomycin. In the case of other infectious agents (e.g., viruses, fungi, etc.) no effective drug treatment may exist. See, e.g., Nickerson et al., 1995 "Mastitis in dairy heifers: initial studies on prevalence and control" *J Dairy Sci* 78:1607-18; Lowy, 1998 "*Staphylococcus aureus* infections" *N Engl J Med* 339:520-32; McKenney et al., 1999 "Broadly protective vaccine for *Staphylococcus aureus* based on an in vivo-expressed antigen" *Science* 284:1523-7; and Lorenz et al., 2000 "Human antibody response during sepsis against targets expressed by methicillin resistant *Staphylococcus aureus*" *FEMS Immunol Med Microbiol* 29:145-53. The existence of multiple drug resistant strains of bacterium (and, indeed, of other infectious agents such as fungi, mycoplasms, etc.) raises the specter of untreatable infections and presents an ongoing challenge to the medical and public health communities. Much previous work has been done on generation of vaccines (e.g., both DNA and protein vaccines) for numerous infectious organisms (especially viruses) and such work is well known to those skilled in the art.

A welcome addition to the art would be a convenient method of therapeutic and/or prophylactic treatment to potentiate an effective immune response (humoral and/or cellular) against antigens of tumors and infectious diseases. The current invention provides these and other approaches and methods in treatment.

SUMMARY OF THE INVENTION

The present invention provides methods of use of various antibody-immunostimulant protein fusions as adjuvants for antigenic protein vaccinations and methods of prophylactically and/or therapeutically treating a disease state in a subject. Compositions comprising the fusion proteins and antigens of the invention are also provided.

In one aspect, the invention comprises a composition of an antibody-immunostimulant fusion protein wherein the fusion protein comprises an effective adjuvant of a disease related antigen. In some embodiments of this aspect, the composition also includes the disease related antigen. Additional embodiments encompass wherein the antibody-immunostimulant fusion protein has antibody specificity against the disease related antigen. The immunostimulant domain of the fusion proteins in these compositions optionally comprises a cytokine (or a sequence or subsequence thereof), a chemokine (or a sequence or subsequence thereof), or an immunostimulant other than a chemokine or cytokine. Examples of such immunostimulant domains (e.g., as are included in optional embodiments of the compositions herein) include, but are not limited to, e.g., cytokines, chemokines, interleukins, interferons, C-X-C chemokines, C-C family chemokines, C chemokines, CX3C chemokines, super antigens, growth factors, IL-1, IL-2, IL-4, IL-6, IL-7, IL-8, IL-10, IL-12, IL-13, IL-17, IL-18, RANTES, mip1α, mip1β, GMCSF, GCSF, gamma interferon, alpha interferon, TNF, CSFs, mip2α, mip2β, PF4, platelet basic protein, hIP10, LD78, Act-2, MCAF, 1309, TCA3, IP-10, lymphotactin, fractalkine, KLH, and fragments thereof of any of the above. Additionally, any of the above embodiments optionally also has a linker.

The antibody domain of the fusion proteins in the compositions of the invention optionally includes an antibody specific for, but not limited to, e.g., a HER2/neu antigen, a tumor antigen, a bacterial antigen, a viral antigen, a mycoplasm antigen, a fungal antigen, a prion antigen, an autoimmune disorder antigen, or an antigen from a parasite (e.g., an infectious mammalian parasite). In other embodiments, such fusion proteins comprise antibody domains specific for antigens other than tumor antigens. Furthermore, in yet other embodiments, the antibody-immunostimulant fusion proteins in the compositions of the invention comprise an antibody fragment, or an Fab domain, an Fab' domain, an F(ab')$_2$ domain, an F(ab)$_2$ domain, an scFv domain, IgG, IgA, IgE, IgM, IgD, IgG1, IgG2, or IgG3.

Also, in some embodiments of the compositions of the invention, the antigen comprises, e.g., a soluble antigen, a soluble antigen bound to a matrix, an insoluble antigen bound to a matrix, an insoluble aggregate of antigens, a nonviable cell-associated antigen, or a nonviable organism-associated antigen, or an antigen conjugated with a liposome. Additionally, such antigen can comprise, e.g., HER2/neu (or HER2/neu shed from a tumor cell) or fragments thereof. Additionally, the antigen in such compositions optionally comprises: an antigen other than a tumor antigen, an antigen arising from a subject, an antigen arising from a disease state within the subject, an antigen arising from a disease related organism within a subject (e.g., a disease state caused by one or more of a tumor, a bacteria, a virus, a mycoplasm, a fungus, a prion, an autoimmune disorder, or an infectious parasite such as an infectious parasite of a mammal, etc.). The antigen can also comprise a tumor antigen, a bacterial antigen, a viral antigen, a mycoplasm antigen, a prion antigen, an autoimmune disorder related antigen, or an infectious parasite antigen. In some embodiments herein, the antigen is an exogenous antigen (which is optionally substantially identical to an antigen arising from a subject, or from a disease state within a subject or from a disease related organism within the subject).

In other embodiments of the compositions herein, the number of antigen molecules and the number of fusion protein molecules are optionally approximately 1:1. In other embodiments, they are optionally in ratios wherein the number of antigen molecules is greater than or lesser than the number of fusion protein molecules, or wherein the number of fusion proteins is substantially saturated by the number of antigen molecules, or wherein the number of antigen molecules is substantially saturated by the number of fusion protein molecules.

The compositions of the invention are optionally incubated for a specific period of time and under specific conditions (e.g., overnight at 4° C., etc. or for even brief periods of time such as 1 second or less, etc.). The compositions of the invention also optionally comprise an excipient (e.g., a pharmaceutically acceptable excipient).

In another aspect, the invention comprises a method of administering an immunological composition by providing an antibody-immunostimulant fusion protein and administering the fusion protein to a subject wherein the fusion protein comprises an effective adjuvant to a disease related antigen and wherein the fusion protein and the antigen in combination elicit an immune response in a subject. Furthermore, some embodiments of this aspect involve the administration of such fusion protein along with providing a disease related antigen (e.g., administering the fusion protein and the antigen to a subject wherein the fusion protein is an effective adjuvant of the antigen). In some embodiments, the fusion protein comprises a cytokine (or a sequence or subsequence thereof), a chemokine (or a sequence or subsequence thereof), or an immunostimulant other than a chemokine or cytokine. In other embodiments of this aspect, the method uses fusion proteins comprising an immunostimulant domain such as (but not limited to), e.g., cytokines, chemokines, interleukins, interferons, C-X-C chemokines, C-C family chemokines, C chemokines, CX3C chemokines, super antigens, growth factors, IL-1, IL-2, IL-4, IL-6, IL-7, IL-8, IL-10, IL-12, IL-13, IL-17, IL-18, RANTES, mip1α, mip1β, GMCSF, GCSF, gamma interferon, alpha interferon, TNF, CSFs, mip2α, mip2β, PF4, platelet basic protein, hIP10, LD78, Act-2, MCAF, 1309, TCA3, IP-10, lymphotactin, fractalkine, KLH, and fragments thereof of any of the above.

The antibody domain of the fusion proteins used in the methods of this aspect of the invention are optionally specific for, e.g., HER2/neu antigen, a tumor antigen, a bacterial antigen, a viral antigen, a mycoplasm antigen, a fungal antigen, a prion antigen, an autoimmune disorder related antigen, an infectious parasite antigen (e.g., a parasite of a mammal). In other embodiments the antibody domain is specific for antigen comprising an antigen other than a tumor antigen. The antibody domain of the fusion proteins in this method aspect of the invention, are optionally (but are not limited to), e.g., an antibody fragment, an Fab domain, an Fab' domain, an F(ab')$_2$ domain, an F(ab)$_2$domain, an scFv domain, IgG, IgA, IgE, IgM, IgD, IgG1, IgG2, or IgG3. In some embodiments of these methods, the fusion protein has antibody specificity for the antigen.

These methods herein also encompass embodiments wherein the antigen comprises, e.g., a tumor antigen, a bacterial antigen, a viral antigen, mycoplasm antigen, a prion antigen, an autoimmune disorder related antigen, a parasite antigen (e.g., one infecting a mammal), an antigen other than a tumor antigen, an antigen arising from the subject, an antigen arising form a disease state within the subject, or an antigen from a disease related organism within the subject. The disease state within the subject that optionally gives rise to such antigens, optionally is caused by, e.g., a tumor, a bacteria, a virus, a mycoplasm, a fungus, a prion, an autoimmune disorder, or a parasite (e.g., one infecting a mammal). The antigens in this aspect of the invention are also optionally exogenous antigens, which can optionally be substantially identical to a disease related antigen arising from a subject, arising from a disease state within a subject, or arising from a disease related organism within a subject. Such exogenous antigen is optionally administered prior to administration of the antibody-immunostimulant fusion proteins, or optionally after the fusion proteins are administered to the subject, or approximately concurrently with the fusion proteins to the subject. Prior to the optional concurrent administration the antigen and the fusion protein can be incubated for a specific time period and under specific conditions (e.g., from 1 second or almost instantaneous incubation up to overnight or longer; at, e.g., 4° C., etc.). The antigen used in the methods in this aspect of the invention also optionally comprises, e.g., HER2/neu, HER2/neu shed from tumor cells, or fragments of such HER2/neu. In some embodiments, the methods comprise wherein the number of antigen molecules and the number of fusion protein molecules are optionally approximately 1:1. In other embodiments, the number of antigen molecules and the number of fusion protein molecules are optionally in ratios wherein the number of antigen molecules is greater than or lesser than the number of fusion protein molecules, or wherein the number of fusion proteins is substantially saturated by the number of antigen molecules, or wherein the number of antigen molecules is substantially saturated by the number of fusion protein molecules. In other embodiments of these methods, more than one fusion protein is optionally used. Such multiple fusion proteins can comprise different immunostimulant domains (e.g., such as ones chosen from (but not limited to) non-cytokine/non-chemokine molecules, cytokines, chemokines, interleukins, interferons, C-X-C chemokines, C-C family chemokines, C chemokines, CX3C chemokines, super antigens, growth factors, IL-1, IL-2, IL-4, IL-6, IL-7, IL-8, IL-10, IL-12, IL-13, IL-17, IL-18, RANTES, mip1α, mip1β, GMCSF, GCSF, gamma interferon, alpha interferon, TNF, CSFs, mip2α, mip2β, PF4, platelet basic protein, hIP10, LD78, Act-2, MCAF, 1309, TCA3, IP-10, lymphotactin, fractalkine, KLH, and fragments thereof of any of the above. Furthermore, the multiple fusion proteins in the methods of this aspect optionally have different specificity. The optional multiple fusion proteins can be specific for, e.g., different antigens on a single molecule, different antigens on a single cell, different antigens on a single tumor, or different antigens on a single organism (e.g., a virus, bacteria, fungus, mycoplasm, prion, parasite), etc. The methods of administering an immunological composition also include embodiments wherein such administration elicits an immune response in a subject.

In yet another aspect, the current invention also includes methods of prophylactically and/or therapeutically treating a disease state in a subject. Such methods include administering an effective amount of an antibody-immunostimulant fusion protein to the subject, wherein the fusion protein comprises an effective adjuvant of a disease related antigen (e.g., one arising from the subject, arising from a disease state within the subject, or arising from a disease related organism within the subject) and wherein the administration elicits an immune response within the subject against the disease related antigen (or closely related antigens). Such method of prophylactically and/or therapeutically treating a disease state also optionally includes administering to the subject an effective amount of an antibody-immunostimulant fusion protein and administering a disease related antigen wherein the fusion protein comprises an effective adjuvant of the disease related antigen.

These and other objects and features of the invention will become more fully apparent when the following detailed description is read in conjunction with the accompanying figures.

DETAILED DISCUSSION OF THE INVENTION

Definitions

Figure 1:
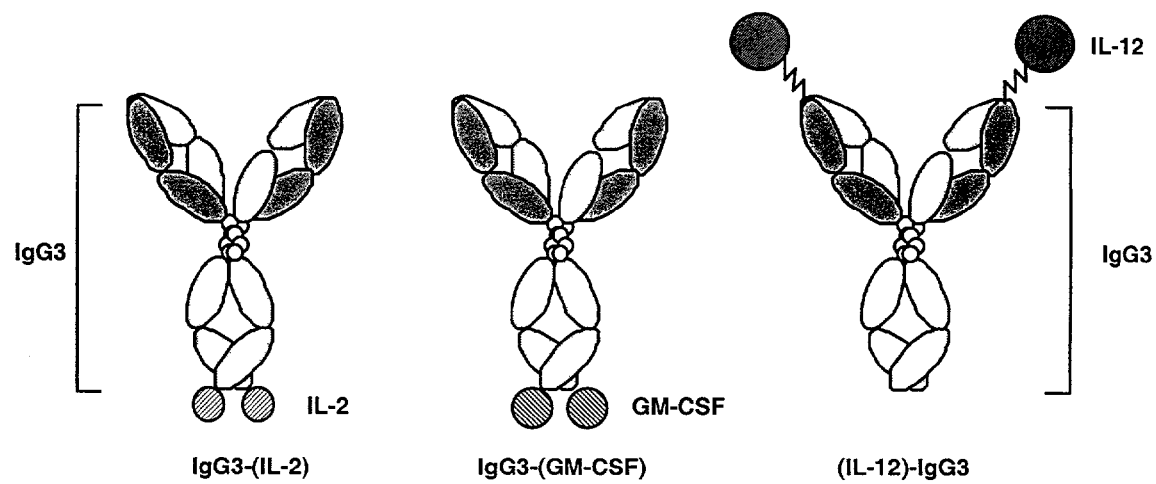
FIG. 1: Schematic diagrams of exemplary antibody-immunostimulant fusion proteins utilized by of the invention.

Unless otherwise defined herein, or below in the remainder of the specification, all technical and scientific terms used herein have the same meaning as commonly understood by those of ordinary skill in the art to which the present invention belongs.

The term "subject" as used herein includes, but is not limited to, a mammal, including, e.g., a human, non-human primate (e.g., monkey), mouse, pig, cow, goat, rabbit, rat, guinea pig, hamster, horse, monkey, sheep, or other non-human mammal, a non-mammal, including, e.g., a non-mammalian vertebrate, such as a bird (e.g., a chicken or duck) or a fish; and a non-mammalian invertebrate. In some embodiments, the methods and compositions of the invention are used to treat (both prophylactically and/or therapeutically) non-human animals. Many commercially important animals are susceptible to various cancers and, especially of concern, to various viral/bacterial, etc. infections which are optionally treated with the current invention.

The term "pharmaceutical composition" herein means a composition suitable for pharmaceutical use in a subject, including an animal or human. A pharmaceutical composition generally comprises an effective amount of an active agent (e.g., the antibody-immunostimulant fusion proteins and antigenic protein vaccinations of the invention) and a pharmaceutically acceptable carrier (e.g., a buffer, adjuvant, or the like).

The term "effective amount" means a dosage or amount sufficient to produce a desired result. The desired result may comprise an objective or subjective improvement in the recipient of the dosage or amount (e.g., long-term survival, decrease in number and/or size of tumors, effective prevention of a disease state, etc.).

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such a protein vaccination and its antibody-immunostimulant fusion protein adjuvant, or composition thereof, that, when administered to a subject who does not display signs or symptoms of a pathology, disease or disorder (or who displays only early signs or symptoms of a pathology, disease, or disorder) diminishes, prevents, or decreases the risk of the subject developing the pathology, disease, or disorder. A "prophylactically useful" agent or compound (e.g., a protein vaccination and its antibody-immunostimulant fusion protein adjuvant) refers to an agent or compound that is useful in diminishing, preventing, treating, or decreasing development of a pathology, disease or disorder.

A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such a protein vaccination and its antibody-immunostimulant fusion protein adjuvant, or composition thereof, that eliminates or diminishes signs or symptoms of a pathology, disease or disorder, when administered to a subject suffering from such signs or symptoms. A "therapeutically useful" agent or compound (e.g., a protein vaccination and its antibody-immunostimulant fusion protein adjuvant) indicates that an agent or compound is useful in diminishing, treating, or eliminating such signs or symptoms of the pathology, disease or disorder.

As used herein, an "antibody" refers to a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain ($V_H$) refer to these light and heavy chains, respectively.

Antibodies exist as intact immunoglobulins or as a number of well characterized fragments produced by digestion with various peptidases. Thus, for example, pepsin digests an antibody below the disulfide linkages in the hinge region to produce F(ab')$_2$, a dimer of Fab which itself is a light chain joined to V$_H$-C$_H$1 by a disulfide bond. The F(ab')$_2$ may be reduced under mild conditions to break the disulfide linkage in the hinge region thereby converting the F(ab')$_2$dimer into an Fab' monomer. The Fab' monomer is essentially an Fab with part of the hinge region (see, *Fundamental Immunology*, W. E. Paul, ed., Raven Press, New York (1999), for a more detailed description of other antibody fragments). While various antibody fragments are defined in terms of the digestion of an intact antibody, one of skill will appreciate that such Fab' fragments, etc. may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv or scFv) antibodies in which a variable heavy and a variable light chain are joined together (directly or through a peptide linker) to form a continuous polypeptide.

An "immunostimulant," or "immunostimulatory" molecule or domain or the like, herein refers to a molecule or domain, etc. which acts (or helps to act) to stimulate or elicit an immune response or immune action in a subject (either cellular or humoral or both). Typical examples of such molecules include, but are not limited to, e.g., cytokines and chemokines. Cytokines act to, e.g., stimulate humoral and/or cellular immune responses. Typical examples of such include, e.g., interleukins such as IL-2, IL-12, etc. Chemokines act to, e.g., selectively attract various leukocytes to specific locations within a subject. They can induce both cell migration and cell activation. Common examples of chemokines include, e.g., RANTES, C-X-C family molecules, Il-8, mip1α, mip1β, etc. For further information, see, e.g., Arai, K. et al, 1990, "Cytokines: coordinators of immune and inflammatory responses" *Annu Rev Biochem* 59:783+; Taub, 1996 "Chemokine-Leukocyte Interactions. The Voodoo That They Do So Well" *Cytokine Growth Factor Rev* 7:355-76.

A "disease related antigen" refers to an antigenic protein, peptide, carbohydrate, lipid, nucleic acid, or combination of any of such, which arises or is present in a subject due to a disease state (e.g., such as cancer or autoimmune disorders) or due to an infectious organism (e.g., such as from infection of a subject with such organisms as bacteria, viruses, prions, mycoplasms, fungi, parasites, etc.). The disease related antigen is optionally either wholly or partially soluble when used as a protein vaccination, alternatively such antigen is a soluble antigen bound to a matrix (e.g., a latex bead or other bead, etc.), an insoluble antigen bound to a matrix (e.g., a latex or other bead, etc.), an insoluble aggregate of antigens, a nonviable cell-associated antigen, a nonviable organism-associated antigen, or an antigen conjugated with a liposome, etc. In some embodiments herein the disease related antigen is exogenous. In other words, such antigen is from outside a subject. An exogenous disease related antigen is optionally identical or substantially identical to an innate or non-exogenous disease related antigen (e.g., one arising from within a subject, or from a disease state and/or infectious organism within a subject, etc.).

Antibody-Immunostimulant Fusion Proteins as Adjuvants of Protein Vaccination

The present invention is based on the use of antibody-immunostimulant fusion proteins not to directly target specific cells to destroy them, etc. (e.g., tumor cells, or infectious bacteria, etc.) but instead, the present invention is based upon targeting a soluble (or another sate, see, below) form of an antigen. The antigen, along with antibody-immunostimulant fusion protein acting as its adjuvant (e.g., a substance or molecule acting or helping to increase an immune response), elicits an immune response (humoral and/or cellular) within the subject against the antigen (e.g., the disease related antigen such as those present on tumor cells, on infectious organisms, etc.). The antigen to which the antibody immunostimulant fusion protein acts as an adjuvant need not be a soluble antigen, though that is often the case in many embodiments. Other embodiments comprise wherein the antigen to which the antibody-immunostimulant fusion protein acts as an adjuvant include such forms as, but not limited to, an antigen(s) (soluble or insoluble) bound to a matrix such as a bead, etc., an insoluble aggregate of antigens or aggregate of soluble antigens (both of which could also comprise other materials, e.g., to help in aggregation, etc., non-viable cell associated antigens (e.g., also including non-viable organismal associated antigens such as form bacteria, viruses, etc., antigens conjugated with liposomes, etc. Additionally, in yet other embodiments, the antibody-immunostimulant fusion protein which acts as the adjuvant to the antigen may itself be conjugated with, e.g., a liposome, etc. while the antigen is, or is not, so conjugated to a liposome.

The present invention provides methods of use of various antibody-immunostimulant protein fusions as adjuvants for antigenic protein vaccinations and methods of prophylactically and/or therapeutically treating a disease state in a subject. Compositions comprising the fusion proteins and antigens of the invention are also provided.

Furthermore, the immune response elicited by the methods and compositions of the invention are specific against, as explained in more detail below, the disease related antigen present within (or, if used in prophylactic treatment, expected or possibly expected within) the subject or closely antigenically related molecules. Thus, for example, an embodiment of the invention optionally comprises an anti-tumor associated (TAA) antigen antibody-immunostimulant and a soluble disease related antigen (e.g., here the TAA) used as a therapeutic treatment. The immune response elicited by such treatment is optionally against such antigen (or a closely related antigen) present on, e.g., the cell surface of tumors present within the subject.

It will be appreciated that the above, as well as the other sections herein, discusses "antigen," e.g., in terms of an antigen administered to a subject along with an antibody-immunostimulant fusion protein. This usage should be understood to describe e a disease related antigen as described previously unless otherwise stated.

The antibody-immunostimulant fusion proteins herein act as adjuvants to disease related antigens (e.g., tumor antigens presented by or on tumor cells or shed from tumor cells such as HER2/neu, or antigens presented by or on an infectious organism such as a virus, a bacteria (e.g., a protein A antigen from *Staphylococcus aureus*), a fungus, a prion, a parasite, an autoimmune disorder, etc.). The current invention utilizes the humoral and/or cellular immune response generated by the disease related antigen (and its antibody-immunostimulant adjuvant) as a means of therapeutic and/or prophylactic treatment of the subject against the organism or disease which generated or caused the disease related antigen's presence in the subject.

The subject's immune response is optionally elicited by the antibody fusion proteins binding their respective antigen (i.e., their respective disease-related antigen) to form an antibody-antigen immunocomplex. See, FIG. 2. Of course, such optional mechanism of action should not be construed as limiting. Other possible and/or additional mechanisms of action optionally are used by the efficacious methods and compositions of the invention. Optionally, this immunocomplex delivers the disease-related antigen to a dendritic cell (DC) or to another appropriate antigen presenting cell (APC) through the interaction of the antibody-immunostimulant fusion protein with surface receptors on the DC or APC such as GMCSF, IL-2, IL-12 receptors, etc. See, FIG. 2. Depending upon, e.g., the specific immunostimulant molecule used in the fusion proteins (e.g., the specific cytokine, chemokine, etc.) the presentation of the antigen to the DC or APC optionally leads to a potent activation of one or both arms of the immune response, i.e., cellular ($T_H1$) and humoral ($T_H2$). Such activation optionally produces a significant immunoprotective activity when the vaccinated subject is challenged with the same (or even, in some embodiments, a closely related) disease related antigen.

Again, it should be noted that the current invention encompasses a myriad of fusions and their uses against a myriad of diseases/conditions. In many examples herein, the anti-HER2/neu antibody fusion, etc. is used as one example, but such should not be construed as limiting. Discussion of HER2/neu protection, etc. is to illustrate the general concepts of the methods and compositions of the invention, namely that use of an antibody-immunostimulant fusion protein as an adjuvant of an antigen vaccination leads to humoral and/or cellular immune response in a subject and thus can be used as a therapeutic and/or prophylactic treatment of the subject for the disease or infection which presents such antigen.

Figure 2:
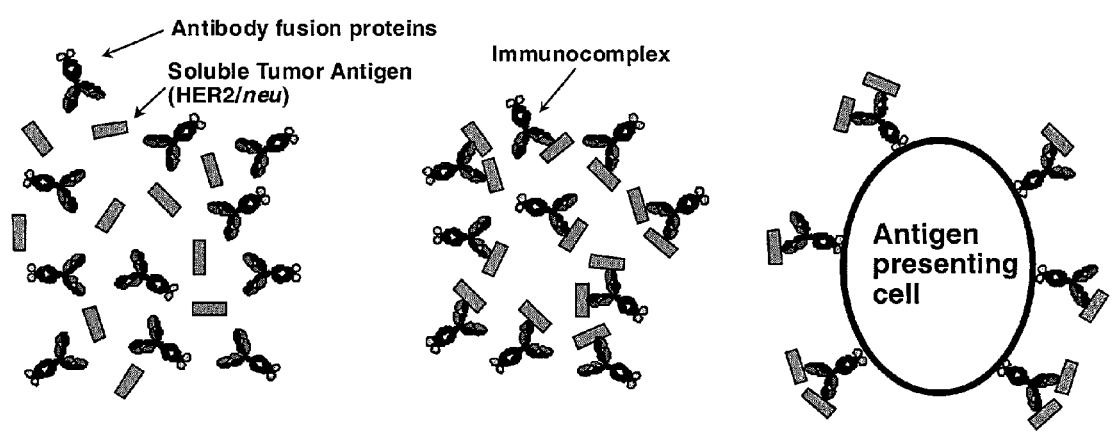
FIG. 2: Schematic diagram showing creation of immunocomplexes of antibody fusion proteins utilized by the invention and soluble antigens and presentation of such complexes to an antigen presenting cell.

The optional interaction of the antibody-immunostimulant fusions and the disease-related antigen with the APC or DC, as illustrated in FIG. 2 could change the quantity and/or quality of antigen presentation (e.g., from that which would occur with solely the disease related antigen used in treatment), which could result in (depending again upon, e.g., the specific immunostimulant fused with the antibody) a strong T and/or B cell immune response against the disease related antigen. Additionally, the general immunostimulatory activity of many immunostimulants (e.g., of cytokines) which are fused to the antibody fusion proteins of the invention may also optionally contribute (or may optionally) per se to the enhancement of the immune response against the targeted antigen (e.g., IL-2-cell proliferative signal, GMCSF-APC activation and IL-12-deviation to $T_H1$, etc.). Again, such optional mechanisms of action should not be construed as limiting; the efficaciousness of the methods and compositions of the invention are not limited to only these mechanisms of action.

The elicited immune response (i.e., produced through use of the methods, etc. of the current invention) is against the disease related antigens expressed on the surface of, e.g., cancer cells or infectious agents (humoral immune response) as well as against disease related antigen peptides associated with MHC class I on the surface of tumor cells or infectious agent cells, etc. (cellular immune response). In some embodiments, the current invention additionally elicits humoral and/or cellular immune responses against other closely related antigens (e.g., antigens closely related either structurally or conformationally to the antigen used as the protein vaccination). For example, since HER2/neu has high homology with other growth factor receptors such as epidermal growth factor receptors 1, 2, and 3 (EGF1, EGF2, EGF3), the elicited immune response (humoral and/or cellular) from the invention against HER2/neu is optionally directed not only against the targeted disease related antigen (HER2/neu), but also against other homologous receptors that are expressed on a cancer cell.

In some embodiments, the methods, etc. of the current invention (as well as the toxicological studies, use studies, etc. of the current invention) are carried out in animal models (see, e.g., Examples I and II below), however, the current invention also encompasses embodiments wherein human subjects are utilized (including clinical trials, etc.). In humans, as in other animal subjects, the antibody-immunostimulant fusion proteins serve as an adjuvant of, e.g., a soluble antigen in both, prophylactic or therapeutic vaccinations. Thus, the invention can target patients with specific antigen expressing tumors, e.g., HER2/neu breast cancers, etc. as well as disease-related antigens presented by infectious organisms (viruses, bacteria, etc.) both wherein the tumor/infectious organism, etc. is within a subject (therapeutic) or before such disease/infection arises in a subject (prophylactic). Thus, the applications allowed by the methods and compositions of the invention comprise a broad range of treatments for both human and other animals in protection against numerous disease states, including cancers and infection by microorganisms.

For example, in prophylactic vaccination, patients at high risk to develop tumors (e.g., those tumors that express HER2/neu) are optionally vaccinated with a mixture of antibody-immunostimulant fusion protein and an appropriate tumor antigen (e.g., HER2/neu, etc.). For example, women whose family history indicates a high probability of developing breast cancer are optionally prophylactically treated with an embodiment of the current invention. For example, antibody-immunostimulant fusion proteins comprising an antibody specific for HER2/neu fused with, e.g., IL-2, IL-12, and GMCSF (i.e., in different antibody constructs) are optionally administered to the woman along with an appropriate amount of HER2/neu antigen (see, below). Typically such fusion proteins and antigens are incubated together in order to form the appropriate immuno-complexes before administration to the subject. The use of the invention would thus cause the woman's immune system to develop an immune response against the HER2/neu protein and thus the woman would be better able to more effectively combat any HER2/neu expressing cancers that arose, and would optionally increase her chances of long-term survival.

Again, it should be noted that in other embodiments of the invention, different antibody/immunostimulant combinations are used against different diseases/conditions and thus against different antigens, etc. Thus the current invention is also optionally used to prophylactically treat subjects for exposure to particular viruses, bacteria, etc. For example, the current invention is optionally used to prophylactically treat persons such as health care workers who might be in environments where risk of exposure to particular viruses/bacteria is high. For example, health care workers likely to be exposed to, e.g., *S. aureus* contamination are optionally prophylactically treated with an anti-protein A antibody-immunostimulant fusion protein and the protein A antigen (see, e.g., Example II below for a similar example with mice). Alternatively, persons likely to encounter, e.g., certain viruses (e.g., such as HIV for sex workers, etc.) are optionally prophylactically treated with an appropriate antibody-immunostimulant fusion specific for an appropriate HIV antigen along with that particular antigen.

In therapeutic treatment vaccinations, patients, e.g., those bearing tumors expressing a particular antigen are vaccinated with a mixture of antigen-specific antibody-immunostimulant fusion protein(s) and the antigen(s) (optionally, the soluble antigen, see above). Again, therapeutic vaccinations are applicable to, e.g., myriad tumor types (and to different antigens presented on the same tumors) and to therapeutic treatment of various infections such as viral, bacterial, etc. So, similarly to a prophylactic treatment (see, above) the antigen targeted can be tumor associated, virus associated, bacterial associated, etc. Therapeutic treatment using the methods and compositions of the invention are especially useful in situations wherein the subject is having difficulty mounting an effective immune response against the disease state. For example, when disease related antigens are not being appropriately interacted with APCs, etc. or when the disease related antigens are recognized as "self" by the immune system, etc.

In some situations, it should be noted, patients will present disease profiles wherein high levels of the specific targeted antigen are present within the patient. For example, some tumors express high circulating levels of soluble antigen (due to, e.g., tumor shedding of the antigen). Such is the case with some HER2/neu expressing tumors; the tumors shed high levels of the antigen. Additionally, in some infections, high levels of a targeted antigen can be present in the patient. Some, e.g., bacterial infections can result in high levels of innately present antigen which is thus able to be targeted. For example, various septicemias can optionally present high levels of soluble antigen in a subject's blood stream. Therefore, in some cases the injection of antibody-immunostimulant fusion protein(s) alone is enough to target the desired antigen. In other words the patient's innate levels of antigen, e.g., soluble HER2/neu, bacterial antigen, etc. are high enough to be targeted by the antibody-immunostimulant fusion proteins and thus trigger the desired immune response. However, even if high levels of innate antigen exist, such patients can also optionally still be injected with a mixture of the antibody-immunostimulant fusion protein(s) and the targeted antigen.

The different antibody-immunostimulant fusion proteins and antigens herein can be used separately or in combination, thus creating an additive or a synergistic effect. In various embodiments of the invention, different immunostimulant domains are optionally used with the same antibody framework (i.e., the same antibody against the same antigen—see, as with the different fusions in Example I, below). Alternatively, and/or additionally, multiple antigens (e.g., two different surface antigens on a bacterial cell, mycoplasm, etc. or two different tumor associated antigens) are optionally used (i.e., the different antigens each have one or more antibody-immunostimulant fusion protein made to target them). Thus, various layers of fine-tuning and specificity are built into the current invention, which thus allow more precise control and targeting of disease treatment in subjects.

Additionally, the methods of the current invention (e.g., as illustrated by treatment with anti-HER2/neu antibody fusion proteins, etc.) are not necessarily a replacement of available therapeutic technologies such as the recombinant antibody Trastuzumab (Herceptin, Genentech, San Francisco, Calif.) treatment. Instead, the current invention is optionally used as an alternative therapy in combination with other treatments (e.g., anti-cancer approaches such as chemotherapy and/or radiotherapy, antibiotics, etc.). For example, in some situations patients with high levels of circulating antigen (e.g., as is seen with tumors that shed $ECD^{HER2}$) or with mutated forms of an antigen (e.g., a mutated form of HER2/neu) who do not respond to treatment with Trastuzumab (see, e.g., Baselga et al., 1996 "Phase II study of weekly intravenous recombinant humanized anti-p185HER2 monoclonal antibody in parities with HER2/neu-overexpressing metastatic breast cancer" *J Clin Oncol* 14:737-44), optionally can benefit from the methods, etc. of the current invention.

In addition, some embodiments of the current invention are also effective for ex vivo generation of mature dendritic cells. In such case, dendritic cells obtained from subjects are treated (in vitro) with a mixture of antibody-immunostimulant fusion protein(s) and the appropriate soluble (or other format, such as antigen on latex beads, etc.) antigen. Then, the mature and programmed dendritic cells are re-implanted into the patient. This is similar in some aspects to some optional embodiments above, i.e., the antibody-immunostimulant complexes form and interact with an APC, etc., but here, such interaction occurs ex vivo.

Components and Construction of Antibody-Immunostimulant Fusion Proteins and Antigen Vaccines It will be appreciated that while, e.g., antibody-cytokine fusion proteins of anti-HER2/neu and IL-2, IL-12, and GMCSF were utilized in the examples herein, the current invention encompasses myriad other combinations of immunostimulant molecules and antibodies in the antibody-immunostimulant fusion proteins it uses. In other words, depending upon the specific condition/disease being considered or treated, various combinations of immunostimulant molecules (e.g., cytokines, chemokines, etc.) and antibodies (e.g., different antibody fragments, antibodies of different isotype, and different antibodies with specificity against different antigens) are encompassed within the current invention.

For example, exemplary non-limiting illustrations of antibody-immunostimulant fusion proteins specific for the extracellular domain of the human tumor associated antigen HER2/neu ($ECD^{HER2}$) were constructed and used in Example I, etc. (using cytokines in the examples detailed). These antibody fusion proteins were composed of human IgG3 containing the variable region of Trastuzumab (Herceptin, Genentech, San Francisco, Calif.) which was genetically fused to the immunostimulatory cytokines interleukin-2 (IL-2), interleukin-12 (IL-12), or granulocyte-macrophage colony stimulator factor (GMCSF). These recombinant proteins are illustrated in FIG. 1.

In addition to the variability of the immunostimulant domain of the fusion proteins utilized herein, the specific antibody domain used also optionally varies. The antibody domains utilized in the examples herein are not to be construed as limiting. For example, different antibodies (e.g., against bacterial antigens, against viral antigens, against different tumor associated antigens, against mycoplasm antigens, against antigens of parasites, prions, autoimmune disorders, etc.) are all optional embodiments of the current invention. This optional variation in antigen specificity allows the methods and compositions of the current invention to be used to treat and/or prevent myriad specific conditions, disease states, etc. Not only is the antigen specificity of the antibody domain variable, but the type of antibody framework which comprises the protein fusion can vary as well. For example the antibody domain of the antibody fusion proteins herein can optionally comprise Fab, Fab', $F(ab)_2$, $F(ab')_2$, Fv, scFv, an antibody fragment, and various combinations thereof, etc.

Antibodies

The current invention utilizes antibody-immunostimulant fusion proteins as adjuvants of protein vaccinations. The antibody immunostimulant fusion proteins used comprise an immunoglobulin molecule (or a portion thereof) that, typically, is specific for the antigen used in the protein vaccination. In typical embodiments, the antibody is specific for a disease related antigen.

The antibody domain of the fusion protein optionally comprises all or part of an immunoglobin molecule and optionally contains all or part of an immunoglobin variable region (i.e., the area of specificity for the disease related antigen) and optionally comprises region(s) encoded by a V gene, and/or a D gene and/or a J gene.

As explained above (see, Definitions, supra) the antibodies used herein optionally comprise F(ab)$_2$, F(ab')$_2$, Fab, Fab', scFv, etc. depending upon the specific requirements of the embodiment. Some embodiments utilize fusion proteins comprising IgG domains. However, other embodiments comprise alternate immunoglobins such as IgM, IgA, IgD, and IgE. Furthermore, all possible isotypes of the various immunoglobins are also encompassed within the current embodiments. Thus, IgG1, IgG2, IgG3, etc. are all possible molecules in the antibody domains of the antibody-immunostimulant fusion proteins used in the invention. In addition to choice in selection of the type of immunoglobin and isotype, different embodiments of the invention comprise various hinge regions (or functional equivalents thereof). Such hinge regions provide flexibility between the different domains of the antibody-immunostimulant fusion proteins. See, e.g., Penichet, et al. 2001 "Antibody-cytokine fusion proteins for the therapy of cancer" *J Immunol Methods* 248: 91-101.

The use of antibody domains fused with various immunostimulants is relatively well known in the art and the use, selection, and construction (or purchase) of appropriate immunoglobins is known to those of skill in the art. See, e.g., Dela Cruz et al., 2000 "Recombinant anti-human HER2/neu IgG3-(GMCSF) fusion protein retains antigen specificity, cytokine function and demonstrates anti-tumor activity" *J Immunol* 165:5112-21; Penichet et al., 2001, "A recombinant IgG3-(IL-2) fusion protein for the treatment of human HER2/neu expressing tumors" *Human Antibodies* 10:43-49; Penichet et al., 2001 "Antibody-cytokine fusion proteins for the therapy of cancer" *J Immunol Methods* 248:91-101 (and the references cited therein); and Peng et al., 1999, "A single-chain IL-12 IgG3 antibody fusion protein retains antibody specificity and Il-12 bioactivity and demonstrates antitumor activity" *J Immunol* 163:250-8, all of which are incorporated for all purposes herein.

Immunostimulants

Another domain which comprises the antibody-immunostimulant fusion proteins of the invention is the immunostimulant domain. As described above, an immunostimulant molecule (or domain) acts to stimulate or elicit an immune response or an action of the immune system of a subject. Immunostimulant domains that are part of the antibody-immunostimulant fusion protein are typically (but not only) of several broad types. Typically, embodiments include, but are not limited to, cytokines and chemokines. In general, cytokines act to, e.g., stimulate humoral and/or cellular immune responses, while chemokines in general induce immune cell migration and activation. The choice of which immunostimulant to include in a particular embodiment depends upon, e.g., which particular immune response effects are desired, e.g., a humoral response, or a cellular immune response, or both. In typical embodiments both cellular and humoral immune responses against a disease related antigen are desired. Thus, as illustrated in Examples I and II below, multiple fusion proteins with varying immunostimulant domains are optionally used in the methods and compositions of the invention.

It will be appreciated that the discussion herein of immunostimulants comprising the listed molecules (e.g., IL-2, etc.) is not to be taken as limiting. In other words, it is to be understood that various embodiments of the invention comprise different combinations of immunostimulant molecules (e.g., other cytokines, chemokines, etc. besides, or in addition to, those listed herein). Thus, specific cytokines/chemokines, etc. (e.g., various interleukin molecules, interferons, IL-2, IL-10, IL-12, IL-17, IL-18, RANTES, mip1α, mip1B, GMCSF, GCSF, gamma interferon, alpha interferon, etc.) fused in the antibody-fusions herein are not limiting and different specific cytokines, chemokines, immunostimulants, etc. can be utilized for different applications, all of which are part of the current invention herein.

For example, one common immunostimulant domain capable of use in the current invention comprises cytokines. Cytokines comprise a large family of growth factors that are primarily secreted from leukocytes and include, e.g., IL-1, IL-2, IL-4, IL-6, IL-7, IL-10, IL-13, interferons, interleukins, IFNs (interferons), TNF (tumor necrosis factor) and CSFs (colony stimulating factors). Various cytokines can stimulate humoral and/or cellular immune responses in subjects and can active phagocytic cells. Interleukins are one species of cytokines which are secreted by leukocytes and which also affect the various cellular responses/actions of leukocytes (e.g., IL-2, IL-12, etc.). In various embodiments, interleukins are used as an immunostimulant domain in the methods/compositions of the invention. Additionally, in other embodiments of the invention, non-interleukin cytokines comprise the immunostimulant domain of the antibody-immunostimulant fusions. See, e.g., Mire-Sluis 1993 *TIBTECH* 11:74-77; Colombo et al. 1992 *Cancer Res* 52:4853-4857; Arai, K. et al, 1990, "Cytokines: coordinators of immune and inflammatory responses" *Annu Rev Biochem* 59:783+, etc.

More specific examples of possible cytokines used in particular embodiments of the current invention include (but are not limited to) the following.

IL-2. IL-2 is a common immunostimulant used to construct antibody-immunostimulant fusion proteins. See, e.g., Penichet et al. 2001 "Antibody-cytokine fusion proteins for the therapy of cancer" *J Immunol Methods* 248:91-101, and the references cited therein. IL-2 stimulates T cells to proliferate and to become cytotoxic. Additionally, IL-2 induces NK cells to respond with increased cytotoxicity toward cells (e.g., tumor cells). Additionally, IL-2 increases vascular permeability leading to the efflux of intravascular fluids into extravascular areas.

IL-12. IL-12 is normally released by professional antigen presenting cells and promotes cell-mediated immunity. It does so by inducing naïve CD4+ cells to differentiate into $T_H1$ cells. IL-12 also can enhance the cytotoxicity of NK and CD8+ T cells. The IFN-γ produced by T and NK cells that are stimulated by IL-12 can lead to other immune actions as well. IL-12 can exist as single chain or double chain (heterodimers) variants. Either permutation of IL-12 is optionally used herein as an immunostimulant domain in the antibody-immunostimulants used herein.

GMCSF. GMCSF is associated with growth and differentiation of hematopoietic cells and is a potent immunostimulator with pleiotropic effects (e.g., augmentation of antigen presentation in numerous cells). Additionally, it is involved in increased expression of MHC II on monocytes and adhesion molecules on granulocytes and monocytes. Furthermore, GMCSF is involved in the amplification of T cell proliferation. In certain embodiments of the current invention, GMCSF comprises the immunostimulant domain in the antibody-immunostimulant fusions used in the invention.

In other common embodiments of the invention, the immunostimulant domain comprises a chemokine (or a fragment thereof). Chemokines, e.g., selectively attract various leukocytes to specific locations and can induce not only cell migration but also activation. Chemokines are typically classified into alpha, beta, and gamma sub-types. Their classification is divided according to the configuration of the first cysteine residues at the amino terminus of the protein. Different classifications of chemokines act to attract different classes of inflammatory cells. Thus, use of such different chemokines in the fusion proteins used in the current invention can result in different immune responses activated in a subject that is treated with such fusion proteins. Chemokines capable of use in the fusion proteins used in the current invention include (but are not limited to) C-X-C group chemokines, IL-8, mip2α, mip2β, PF4, platelet basic protein, hIP10, C-C family chemokines, LD78, Act-2, MCAF, 1309, RANTES, TCA3, IP-10, C chemokines, lymphotactin, CX3C (or c-x3-c) chemokines, fractalkine, etc.

Other embodiments of the invention comprise antibody-immunostimulant fusion proteins comprising immunostimulants other than cytokines or chemokines. For example, antibody-immunostimulant fusion proteins optionally comprise KLH (keyhole limpet hemocyanin) or other such immunogenic compounds, as well as "super antigens" which cause direct stimulation of T cells and/or B cells without direct antigen presentation. Super antigens and compounds such as KLH (as well as their use, etc.) are well known by those in the art. See, e.g., Johnson, et al. "Superantigens in human disease" *Scientific American* April 1992, p. 92-101, and Sekaly, R. (ed.) "Bacterial Superantigens" *Seminars in Immunol*. Vol. 5, 1993.

Again, the actual specific immunostimulant molecule in various embodiments of the fusion proteins used in the invention (whether comprising a cytokine, chemokine, etc.) will depend upon, e.g., the specific disease state/condition, the specific antigen targeted, the specific action desired (e.g., elicitation of a humoral immune response, a cellular immune response, or both), etc.

Construction

The construction of antibody-immunostimulant fusion proteins is well known to those versed in the art. For example, Penichet et al. 2001 "A recombinant IgG3-(IL-2) fusion protein for the treatment of human Her2/neu expressing tumors" *Hum Antibodies* 10:43+; Peng, 1999, supra; and Dela Cruz, 2000, supra all describe antibody-immunostimulant fusion proteins and their construction. Numerous other sources are replete throughout the literature.

The specific antibody-immunostimulant fusion proteins utilized in the current invention are optionally obtained or created by any method known in the art (including purchase from commercial sources). For example, nucleic acid sequences encoding the appropriate antibody framework (see, above) are optionally cloned and ligated into appropriate vectors (e.g., expression vectors for, e.g., prokaryotic or eukaryotic organisms). Additionally, nucleic acid sequences encoding the appropriate immunostimulant molecule are optionally cloned into the same vector in the appropriate orientation and location so that expression from the vector produces an antibody-immunostimulant fusion protein. Some optional embodiments also require post-expression modification, e.g., assembly of antibody subunits, etc. The techniques and art for the above (and similar) manipulations are well known to those skilled in the art. Pertinent instructions are found in, e.g., Sambrook et al., *Molecular Cloning—A Laboratory Manual* (2nd Ed.), Vols. 1-3, Cold Spring Harbor Laboratory, Cold Spring Harbor, N.Y., 1989 and *Current Protocols in Molecular Biology*, F. M. Ausubel et al., eds., Current Protocols, a joint venture between Greene Publishing Associates, Inc. and John Wiley & Sons, Inc. (supplemented through 1999). In some alternate embodiments, the antibody domain and the immunostimulant domain are assembled post-expression through, e.g., chemical means.

Administration of Antibody-Immunostimulants as Adjuvants of Protein Vaccination

Compositions

The antibody-immunostimulant fusion proteins and/or protein vaccinations (e.g., the disease related antigens) are optionally administered to subjects in need of treatment (either therapeutically or prophylactically) in any appropriate sterile pharmaceutical carrier. Such pharmaceutical carrier acts to maintain the solubility and action of the fusion proteins and antigens. In some embodiments, it may be desired to administer additional components in conjunction with the fusion proteins/antigens. For example, in some treatment regimes, chemotherapeutic agents, antibiotics, additional antibody fusion proteins comprising growth factors, etc. are all optionally included with the compositions of the invention.

In typically embodiments, preparations for administration to subjects include sterile aqueous or non-aqueous solutions, suspensions, and emulsions. Some embodiments include non-aqueous solvents such as propylene glycol, polyethylene glycol, vegetable oils (e.g., olive oils), organic esters (e.g., ethyl oleate) and other solvents known to those of skill in the art. Physiologically acceptable carriers (or excipients) are optionally used in certain embodiments of the invention. Examples of such include, e.g., saline, PBS, Ringer's solution, lactated Ringer's solution, etc. Additionally, preservatives and additives are optionally added to the compositions to help ensure stability and sterility. For example, antibiotics and other bacteriocides, antioxidants, chelating agents, and the like are all optionally present in various embodiments of the compositions herein.

In the preparation of the compositions herein, typical embodiments include wherein the antibody-immunostimulant fusion proteins and the specific disease related antigen are incubated together for specific periods of time (e.g., in order for the appropriate immunocomplexes to form between the antigen and the fusion protein) before the composition is administered to the subject. Typical embodiments include wherein such incubations are done at 4° C., e.g. overnight. However, other embodiments include wherein the incubation temperatures and times vary. For example, the compositions may be incubated at a variety of lengths and temperatures. The determination of the conditions/temperatures is determined based upon, e.g., the specific antigen involved, the specific antibody fusion proteins involved, the affinity between the antigen and the antibodies, etc. In some embodiments of the invention, the ratio of the number of molecules of an antibody-immunostimulant fusion protein and the number of molecules of an appropriate antigen are roughly or approximately equal (e.g., 1:1). However, in other embodiments the ratio is optionally not 1:1. For example, some embodiments optionally comprise wherein the number of molecules of antibody-fusion proteins is greater than the number of molecule of antigen or wherein the number of molecules of antigen are greater than the number of molecules of antibody fusion protein. In some embodiments the number of antigen molecules is great enough to totally saturate the number of antibody fusion protein molecules. In other words, all available antibodies will have antigen immunocomplexed to them. In other embodiments, the antigen is limiting (e.g., there is more than enough antibody so that all available antigen is immunocomplexed with the antibody). In other embodiments, the various amounts of the disease related antigen and the antibody-immunostimulant fusion protein are allocated so that an equal molarity (or an approximately equal molarity) exists between the components. In some typical embodiments, the amount of each component is allocated so that the binding unit equivalents of each component are equal or roughly/approximately equal. See, Example I, below.

In some embodiments, the various constituents of the compositions come pre-measured and/or prepackaged and/or ready for use without additional measurement, etc. The present invention also optionally comprises kits for conducting/using the methods and/or the compositions of the invention. In particular, these kits optionally include, e.g., appropriate antibody-immunostimulant fusion proteins (and optionally mixtures of a number of such proteins for performing synergistic treatments, see, above), and optionally appropriate disease related antigen(s) as well). Additionally, such kits can also comprise appropriate excipients (e.g., pharmaceutically acceptable excipients) for performing therapeutic and/or prophylactic treatments of the invention. Such kits optionally contain additional components for the assembly and/or use of the compositions of the invention including, but not limited to, e.g., diluents, adjuvants, etc.

The compositions described herein are optionally packaged to include all (or almost all) necessary components for performing the methods of the invention or for using the compositions of the invention (optionally including, e.g., written instructions for the use of the methods/compositions of the invention). For example, the kits can optionally include such components as, e.g., buffers, reagents, serum proteins, antibodies, substrates, etc. In the case of prepackaged reagents, the kits optionally include pre-measured or pre-dosed amounts that are ready to incorporate into the methods without measurement, e.g., pre-measured fluid aliquots, or pre-weighed or pre-measured solid reagents that can be easily reconstituted by the end-user of the kit.

Such kits also typically include appropriate instructions for performing the methods of the invention and/or using the compositions of the invention. In some embodiments, the components of the kits/packages are provided in a stabilized form, so as to prevent degradation or other loss during prolonged storage, e.g., from leakage. A number of stabilizing processes/agents are widely used for reagents, etc. that are to be stored, such as the inclusion of chemical stabilizers (i.e., enzymatic inhibitors, microbicides/bacteriostats, anticoagulants), etc.

In some embodiments, the multiple compositions are used to treat the subject. For example, multiple dosages of the fusion protein/antigen mixture are optionally given to a subject over a prescribed time period. Ranges for such are optionally highly variable depending upon, e.g., the subject's response to treatment, any toxicities and/or or adverse reactions to treatment, etc. and are optionally adjusted to suit each individual treatment regime/subject. Additionally, the fusion protein is optionally given to the subject in a separate composition than the antigen mixture. For example, the antigen composition is optionally administered to the subject prior to, approximately concurrently to, or after the fusion protein composition is administered to the subject. Furthermore, as mentioned herein, some disease states/conditions present situations wherein a separate administration of disease related antigen is not given. For example, some HER2/neu expressing tumors shed large amounts of the HER2/neu antigen. In optional embodiments, the current invention utilizes such shed antigen by optionally using such to form immunocomplexes with the fusion proteins administered. Again, such optional mechanism of action should not be construed as limiting upon the efficaciousness of the methods and compositions of the current invention.

In some embodiments herein, the invention comprises a composition of an antibody-immunostimulant fusion protein wherein the fusion protein comprises an effective adjuvant of a disease related antigen. In some embodiments, the composition also includes the disease related antigen. Additional embodiments encompass wherein the antibody-immunostimulant fusion protein has antibody specificity against the disease related antigen. The immunostimulant domain of the fusion proteins in these compositions optionally comprises a cytokine (or a sequence or subsequence thereof), a chemokine (or a sequence or subsequence thereof), or an immunostimulant other than a chemokine or cytokine. Examples of such immunostimulant domains (e.g., as are included in optional embodiments of the compositions herein) include, but are not limited to, e.g., cytokines, chemokines, interleukins, interferons, C-X-C chemokines, C-C family chemokines, C chemokines, CX3C chemokines, super antigens, growth factors, IL-1, IL-2, IL-4, IL-6, IL-7, IL-8, IL-10, IL-12, IL-13, IL-17, IL-18, RANTES, mip1α, mip1β, GMCSF, GCSF, gamma interferon, alpha interferon, TNF, CSFs, mip2α, mip2β, PF4, platelet basic protein, hIP10, LD78, Act-2, MCAF, 1309, TCA3, IP-10, lymphotactin, fractalkine, KLH, and fragments thereof of any of the above. Additionally, any of the above embodiments optionally also has a linker (other embodiments optionally do not have linkers). Linker regions or domains are optionally between, e.g., the immunostimulant domain and the antibody domain in the fusion proteins, etc.

The antibody domain of the fusion proteins in the compositions of the invention optionally includes an antibody specific for, but not limited to, e.g., a HER2/neu antigen, a tumor antigen, a bacterial antigen, a viral antigen, a mycoplasm antigen, a fungal antigen, a prion antigen, an autoimmune disorder antigen, or an antigen from a parasite (e.g., an infectious mammalian parasite). In other embodiments, such fusion proteins comprise antibody domains specific for antigens other than tumor antigens. Furthermore, in yet other embodiments, the antibody-immunostimulant fusion proteins in the compositions of the invention comprise an antibody fragment, or an Fab domain, an Fab' domain, an F(ab')$_2$ domain, an F(ab)$_2$ domain, an scFv domain, IgG, IgA, IgE, IgM, IgD, IgG1, IgG2, or IgG3.

Also, in some embodiments of the compositions of the invention, the antigen comprises, e.g., a soluble antigen, a soluble antigen bound to a matrix, an insoluble antigen bound to a matrix, an insoluble aggregate of antigens, a nonviable cell-associated antigen, or a nonviable organism-associated antigen, or an antigen conjugated with a liposome. Additionally, such antigen can comprise, e.g., HER2/neu (or HER2/neu shed from a tumor cell) or fragments thereof. Additionally, the antigen in such compositions optionally comprises: an antigen other than a tumor antigen, an antigen arising from a subject, an antigen arising from a disease state within the subject, an antigen arising from a disease related organism within a subject (e.g., a disease state caused by one or more of a tumor, a bacteria, a virus, a mycoplasm, a fungus, a prion, an autoimmune disorder, or an infectious parasite such as an infectious parasite of a mammal, etc.). The antigen can also comprise a tumor antigen, a bacterial antigen, a viral antigen, a mycoplasm antigen, a prion antigen, an autoimmune disorder related antigen, or an infectious parasite antigen. In some embodiments herein, the antigen is an exogenous antigen (which is optionally substantially identical to an antigen arising from a subject, or from a disease state within a subject or from a disease related organism within the subject).

In other embodiments of the compositions herein, the number of antigen molecules and the number of fusion protein molecules are optionally approximately 1:1. In other embodiments, they are optionally in ratios wherein the number of antigen molecules is greater than or lesser than the number of fusion protein molecules, or wherein the number of fusion proteins is substantially saturated by the number of antigen molecules, or wherein the number of antigen molecules is substantially saturated by the number of fusion protein molecules.

The compositions of the invention are optionally incubated for a specific period of time and under specific conditions (e.g., overnight at 4° C., etc. or for even brief periods of time such as 1 second or less, etc.). The compositions of the invention also optionally comprise an excipient (e.g., a pharmaceutically acceptable excipient).

Examples I and II below, give several non-limiting examples of the compositions and administration of the compositions of the invention. See, below. It will be appreciated that different combinations of antibodies and immunostimulants will optionally require different administration profiles (e.g., certain immunostimulant domains optionally need a specific buffer, etc.). Additionally, some treatment regimes optionally will include additional therapeutic and/or prophylactic components (e.g., antibiotics and the like).

Administration

In typical embodiments, the antibody-immunostimulant fusion proteins and the antigen vaccinations are injected parenterally, (e.g., intravenously, intraperitoneally, intramuscularly, or subcutaneously) in a subject. In other embodiments, the compositions of the invention are delivered via non-injection means, see, below. Typically, the dosage ranges for such administration are large enough to elicit the desired effect in the subject (e.g., elicitation of humoral and/or cellular immune responses against the disease related antigen and/or, e.g., positive anti-tumor or anti-infection activity). The dosages given are optionally optimized for the individual subject based upon, e.g., the subject's age, gender, species, and weight, as well the extent or presence of the disease state to be treated (either therapeutically or prophylactically). For example, the dosage of the fusion protein/antigen compositions given can range from less than 0.1 mg/kg subject weight to 200 mg/kg subject weight or more. The dosage given depends upon, e.g., the specific subject (age, weight, general health, gender, species, etc.), the presence and/or progression or stage of a disease state, the specific antigen, the specific antibody fusion protein, and the specific immunostimulant. For example, some optional immunostimulants present toxicities in higher doses (thus, more composition does not necessarily equal more benefit). Thus, the administration is optionally tailored for each subject. Doses are optionally given in a series. In other words, multiple doses are optionally given over a course of treatment. The dosage course is optionally modified during the treatment based upon the subject's response. For example, if a subject does not response satisfactorily within a specific time period, the dosage and/or timing of dosages is optionally increased or altered.

Again, Examples I and II below, give non-limiting examples of dosage (amounts and timing) schedules using the compositions of the invention. Such treatment schedules, again, are solely examples tailored for use with the mice, etc. in the Examples, and are not to be taken as limiting.

The present invention also includes methods of therapeutically or prophylactically treating a disease or disorder, eliciting an immune response (humoral and/or cellular) in a subject and administering an immunological composition by administering in vivo or ex vivo one or more nucleic acids or polypeptides/fusion proteins/antigens of the invention as described herein (or compositions comprising a pharmaceutically acceptable excipient and one or more such nucleic acids or polypeptides and/or fusion proteins and/or antigens) to a subject, including, e.g., a mammal, including, e.g., a human, primate, mouse, pig, cow, goat, rabbit, rat, guinea pig, hamster, horse, sheep; or a non-mammalian vertebrate such as a bird (e.g., a chicken or duck) or a fish, or invertebrate.

In one optional aspect of the invention, in ex vivo methods, one or more cells or a population of cells of interest of the subject (e.g., dendritic cells, antigen presenting cells, etc.) are obtained or removed from the subject and contacted with an amount of a fusion protein and antigen of the invention that is effective in prophylactically or therapeutically treating a disease, disorder, or other condition. The contacted cells are then returned or delivered to the subject to the site from which they were obtained or to another site (e.g., via intramuscular injection, etc.) of interest in the subject to be treated. The methods/compositions of the invention optionally elicit an effective immune response whether such cells are delivered to a site of need (e.g., a tumor or infection site) or to a site unrelated to such (e.g., a distant body part, etc.). If desired, the contacted cells may be deposited, injected, grafted, etc. onto a tissue, organ, or system site (including, e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc) of interest in the subject using standard and well-known depositing, injection and grafting techniques or, e.g., delivered to the blood or lymph system using standard delivery or transfusion techniques.

The invention also optionally provides in vivo methods in which one or more cells or a population of cells of interest of the subject are contacted directly or indirectly with an amount of an antibody fusion protein and/or antigen of the invention effective in prophylactically or therapeutically treating a disease, disorder, or other condition. In either format, the antibody fusion protein and/or antigen is optionally administered or transferred to the cells (e.g., tumor cells, tumor tissue sample, infection site (such as an abscess, etc.) organ cells, blood cells, cells of the skin, lung, heart, muscle, brain, mucosae, liver, intestine, spleen, stomach, lymphatic system, cervix, vagina, prostate, mouth, tongue, etc.) by any of a variety of formats, including topical administration, injection (e.g., by using a needle or syringe), or vaccine or gene gun delivery, pushing into a tissue, organ, or skin site. The molecules can be delivered, for example, intramuscularly, intradermally, subdermally, subcutaneously, orally, intraperitoneally, intrathecally, intravenously, or placed within a cavity of the body (including, e.g., during surgery), or by inhalation or vaginal or rectal administration. In more typical embodiments, the antibody fusion protein and/or antigen of the invention are optionally administered or transferred to a site that is not directly in need of treatment, etc. For example, in typical embodiments, the antibody fusion protein and/or antigen of the invention are injected (e.g., see, above), e.g., intramuscularly or intravenously at a site distant from, e.g. a tumor, infection site, etc. (e.g., injection into the flank of an animal when the tumors to be combated are in the lungs, etc.). The immune response is still generated by the antibody-immunostimulant fusion proteins/antigen compositions of the invention.

In another optional aspect, the invention provides ex vivo methods in which one or more cells of interest or a population of cells of interest of the subject (e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc.) are obtained or removed from the subject and transformed by contacting said one or more cells or population of cells with a polynucleotide construct comprising a target nucleic acid sequence encoding antibody-immunostimulant fusion proteins and/or antigen used in the invention, as biologically active molecules that are effective in prophylactically or therapeutically treating the disease, disorder, or other condition. The one or more cells or population of cells is contacted with a sufficient amount of the polynucleotide construct (e.g., encoding antibody-immunostimulant fusion proteins and/or antigen) and a promoter controlling expression of said nucleic acid sequence such that uptake of the polynucleotide construct (and promoter) into the cell(s) occurs and sufficient expression of the target nucleic acid sequence of the invention results to produce an amount of the biologically active molecules effective to prophylactically or therapeutically treat the disease, disorder, or condition. The polynucleotide construct may include a promoter sequence (e.g., CMV promoter sequence) that controls expression of the nucleic acid sequence of the invention and/or, if desired, one or more additional nucleotide sequences encoding at least one or more of another molecule of the invention, such as a cytokine, adjuvant, or co-stimulatory molecule, or other polypeptide, etc. of interest, etc.

Following transfection, the transformed cells optionally are returned, delivered, or transferred to the subject to the tissue site or system from which they were obtained or to another site (e.g., tumor cells, tumor tissue sample, organ cells, blood cells, cells of the skin, lung, heart, muscle, brain, mucosae, liver, intestine, spleen, stomach, lymphatic system, cervix, vagina, prostate, mouth, tongue, etc.) in the subject. If desired, the cells may be grafted onto a tissue, skin, organ, or body system of interest in the subject using standard and well-known grafting techniques or delivered to the blood or lymphatic system using standard delivery or transfusion techniques. Such delivery, administration, or transfer of transformed cells is typically made by using one or more of the routes or modes of administration described above. Expression of the target nucleic acid occurs naturally or can be induced and an amount of the encoded antibody-immunostimulant fusion proteins and/or antigen is expressed sufficient and effective to treat the disease or condition. The site of expression of the compositions, etc. need not be at or near the site of need in the subject. As explained throughout, the antibody-immunostimulant fusion proteins and/or antigens in the compositions of the invention do not necessarily need to come into direct contact with, e.g., a tumor cell, infectious organism, etc. in order to elicit an immune response against such, e.g., tumor or infection.

In another optional aspect, the invention provides in vivo methods in which one or more cells of interest or a population of cells of the subject (e.g., including those cells and cells systems and subjects described above) are transformed in the body of the subject by contacting the cell(s) or population of cells with (or administering or transferring to the cell(s) or population of cells using one or more of the routes or modes of administration described above) a polynucleotide construct comprising a nucleic acid sequence that encodes a biologically active antibody-immunostimulant fusion protein and/or antigen used in the invention that is effective in prophylactically or therapeutically treating the disease, disorder, or other condition.

The polynucleotide construct optionally can be administered or transferred to cell(s) by first directly contacting cells using one or more of the routes or modes of administration described above with a sufficient amount of the polynucleotide construct comprising the nucleic acid sequence encoding the biologically active molecules, and a promoter controlling expression of the nucleic acid sequence, such that uptake of the polynucleotide construct (and promoter) into the cell(s) occurs and sufficient expression of the nucleic acid sequence of the invention results to produce an amount of the biologically active antibody fusion protein and/or antigen effective to prophylactically or therapeutically treat the disease or disorder. Expression of the target nucleic acid occurs naturally or can be induced such that an amount of the encoded antibody fusion protein and/or antigen is expressed sufficient and effective to treat the disease or condition by eliciting the appropriate immune response. The polynucleotide construct may include a promoter sequence (e.g., CMV promoter sequence) that controls expression of the nucleic acid sequence and/or, if desired, one or more additional nucleotide sequences encoding at least one or more of another molecule used in the invention, a cytokine, adjuvant, or co-stimulatory molecule, or other such molecules of interest.

In each of the in vivo and ex vivo treatment methods as described above, a composition comprising an excipient and the antibody fusion protein and/or antigen or nucleic acid encoding such as used in the invention can be administered or delivered. In one aspect, a composition comprising a pharmaceutically acceptable excipient and such molecules or nucleic acid as used in the invention is administered or delivered to the subject as described above in an amount effective to treat the disease or disorder.

In another aspect, in each in vivo and ex vivo treatment method described above, the amount of polynucleotide administered to the cell(s) or subject can be an amount sufficient that uptake of said polynucleotide into one or more cells of the subject occurs and sufficient expression of said nucleic acid sequence results to produce an amount of the biologically active molecules effective to enhance or elicit an immune response in the subject. In another aspect, for each such method, the amount of molecules administered to cell(s) or subject can be an amount sufficient to enhance or elicit an immune response in the subject.

In yet another aspect, in an in vivo or ex vivo treatment method in which a polynucleotide construct (or composition comprising a polynucleotide construct) is used, the expression of the polynucleotide construct can be induced by using an inducible on-and-off gene expression system. Examples of such on-and-off gene expression systems include the Tet-On™ Gene Expression System and Tet-Off™ Gene Expression System, respectively. Other controllable or inducible on-and-off gene expression systems are known to those of ordinary skill in the art. With such system, expression of the target nucleic of the polynucleotide construct can be regulated in a precise, reversible, and quantitative manner. Gene expression of the target nucleic acid can be induced, for example, after the stable transfected cells containing the polynucleotide construct comprising the target nucleic acid are delivered or transferred to or made to contact a tissue site, organ or system of interest. Such systems are of particular benefit in treatment methods and formats in which it is advantageous to delay or precisely control expression of the target nucleic acid (e.g., to allow time for completion of surgery and/or healing following surgery; to allow time for the polynucleotide construct comprising the target nucleic acid to reach the site, cells, system, or tissue for expression; to allow time for the graft containing cells transformed with the construct to become incorporated into the tissue or organ onto or into which it has been spliced or attached, etc.)

In some embodiments, the invention comprises a method of administering an immunological composition by providing an antibody-immunostimulant fusion protein and administering the fusion protein to a subject wherein the fusion protein comprises an effective adjuvant to a disease related antigen and wherein the fusion protein and the antigen in combination elicit an immune response in a subject. Furthermore, some embodiments involve the administration of such fusion protein along with providing a disease related antigen (e.g., administering the fusion protein and the antigen to a subject wherein the fusion protein is an effective adjuvant of the antigen). In some embodiments, the fusion protein comprises a cytokine (or a sequence or subsequence thereof), a chemokine (or a sequence or subsequence thereof), or an immunostimulant other than a chemokine or cytokine. In other embodiments, the methods of the invention use fusion proteins comprising an immunostimulant domain such as (but not limited to), e.g., cytokines, chemokines, interleukins, interferons, C-X-C chemokines, C-C family chemokines, C chemokines, CX3C chemokines, super antigens, growth factors, IL-1, IL-2, IL-4, IL-6, IL-7, IL-8, IL-10, IL-12, IL-13, IL-17, IL-18, RANTES, mip1α, mip1β, GMCSF, GCSF, gamma interferon, alpha interferon, TNF, CSFs, mip2α, mip2β, PF4, platelet basic protein, hIP10, LD78, Act-2, MCAF, 1309, TCA3, IP-10, lymphotactin, fractalkine, KLH, and fragments thereof of any of the above.

The antibody domain of the fusion proteins used in the embodiments of the methods of the invention are optionally specific for, e.g., HER2/neu antigen, a tumor antigen, a bacterial antigen, a viral antigen, a mycoplasm antigen, a fungal antigen, a prion antigen, an autoimmune disorder related antigen, an infectious parasite antigen (e.g., a parasite of a mammal). In other embodiments the antibody domain is specific for antigen comprising an antigen other than a tumor antigen. The antibody domain of the fusion proteins in such embodiments of the invention, are optionally (but are not limited to), e.g., an antibody fragment, an Fab domain, an Fab' domain, an F(ab')$_2$ domain, an F(ab)$_2$domain, an scFv domain, IgG, IgA, IgE, IgM, IgD, IgG1, IgG2, or IgG3. In some embodiments of these methods, the fusion protein has antibody specificity for the antigen.

These methods herein also encompass embodiments wherein the antigen comprises, e.g., a tumor antigen, a bacterial antigen, a viral antigen, a mycoplasm antigen, a prion antigen, an autoimmune disorder related antigen, a parasite antigen (e.g., one infecting a mammal), an antigen other than a tumor antigen, an antigen arising from the subject, an antigen arising form a disease state within the subject, or an antigen from a disease related organism within the subject. The disease state within the subject that optionally gives rise to such antigens, optionally is caused by, e.g., a tumor, a bacteria, a virus, a mycoplasm, a fungus, a prion, an autoimmune disorder, or a parasite (e.g., one infecting a mammal). The antigens in such embodiments of the invention are also optionally exogenous antigens, which can optionally be substantially identical to a disease related antigen arising from a subject, arising from a disease state within a subject, or arising from a disease related organism within a subject. Such exogenous antigen is optionally administered prior to administration of the antibody-immunostimulant fusion proteins, or optionally after the fusion proteins are administered to the subject, or approximately concurrently with the fusion proteins to the subject. Prior to the optional concurrent administration the antigen and the fusion protein can be incubated for a specific time period and under specific conditions (e.g., from 1 second or almost instantaneous incubation up to overnight or longer; at, e.g., 4° C., etc.). The antigen used in such embodiments of the invention also optionally comprises, e.g., HER2/neu, HER2/neu shed from tumor cells, or fragments of such HER2/neu. In some embodiments, the methods comprise wherein the number of antigen molecules and the number of fusion protein molecules are optionally approximately 1:1. In other embodiments, the number of antigen molecules and the number of fusion protein molecules are optionally in ratios wherein the number of antigen molecules is greater than or lesser than the number of fusion protein molecules, or wherein the number of fusion proteins is substantially saturated by the number of antigen molecules, or wherein the number of antigen molecules is substantially saturated by the number of fusion protein molecules. In other embodiments of these methods, more than one fusion protein is optionally used. Such multiple fusion proteins can comprise different immunostimulant domains (e.g., such as ones chosen from (but not limited to) non-cytokine/non-chemokine molecules, cytokines, chemokines, interleukins, interferons, C-X-C chemokines, C-C family chemokines, C chemokines, CX3C chemokines, super antigens, growth factors, IL-1, IL-2, IL-4, IL-6, IL-7, IL-8, IL-10, IL-12, IL-13, IL-17, IL-18, RANTES, mip1α, mip1β, GMCSF, GCSF, gamma interferon, alpha interferon, TNF, CSFs, mip2α, mip2β, PF4, platelet basic protein, hIP10, LD78, Act-2, MCAF, 1309, TCA3, IP-10, lymphotactin, fractalkine, KLH, and fragments thereof of any of the above. Furthermore, the multiple fusion proteins in these methods optionally have different specificity. The optional multiple fusion proteins can be specific for, e.g., different antigens on a single molecule, different antigens on a single cell, different antigens on a single tumor, or different antigens on a single organism (e.g., a virus, bacteria, fungus, mycoplasm, prion, parasite), etc. The methods of administering an immunological composition also include embodiments wherein such administration elicits an immune response in a subject.

In yet other embodiments, the current invention also includes methods of prophylactically and/or therapeutically treating a disease state in a subject. Such methods include administering an effective amount of an antibody-immunostimulant fusion protein to the subject, wherein the fusion protein comprises an effective adjuvant of a disease related antigen (e.g., one arising from the subject, arising from a disease state within the subject, or arising from a disease related organism within the subject) and wherein the administration elicits an immune response within the subject against the disease related antigen (or closely related antigens). Such method of prophylactically and/or therapeutically treating a disease state also optionally includes administering to the subject an effective amount of an antibody-immunostimulant fusion protein and administering a disease related antigen wherein the fusion protein comprises an effective adjuvant of the disease related antigen.

Use of the Invention to Elicit Immune Responses Against HER2/Neu Tumor Antigen and *Staphylococcus* Protein A Antigen One possibility to overcome problems presented in therapeutic and/or prophylactic treatment of some diseases/conditions/etc. (such as microorganism infections that have no effective drug treatment, e.g., multiple drug resistant bacteria, etc., or such as certain cancers, e.g., HER2/neu presenting cancers) is immunization with specific proteins to cause a strong immune response against the expressing tumors or infectious agents, etc. For example, as explained in more detail below, some embodiments of the invention involve treatment (e.g., injection/vaccination) of cancer patients with an appropriate antigen in hope of eliciting an immune response in the patient against the tumor cells. Additionally, such treatment (e.g., vaccination with appropriate antigens) is a common approach in eliciting an immune response against certain types of infectious organisms (e.g., viruses, etc.) Traditional vaccination strategies against infectious organisms are well known to those in the art.

The current invention, uses antibody-immunostimulant fusion proteins as adjuvants of protein vaccinations (see, e.g., Example I below detailing HER2/neu protein and Example II detailing *Staphylococcus aureus* protein A) as an effective means to elicit both humoral and/or cellular immune responses in subjects against disease related antigens from e.g., tumors, infectious agents such as viruses, etc. For example, as shown in Example I, below antibody-immunostimulant fusion proteins comprising anti-HER2/neu IgG3-(IL-2), anti-HER2/neu IgG3-(IL-12), and anti-HER2/neu IgG3-(GMCSF)) were used as adjuvants (i.e. immunoenhancers) of a soluble form of an antigen used as a protein vaccination (again, herein illustrated by HER2/neu). Of course, in other embodiments, different antigens are selected for use. See, above.

The current invention does not use the antibody-immunostimulant fusion proteins for direct targeting of, e.g., a tumor or an infectious agent, instead the antibody fusions, in conjunction with the antigen, are used to elicit a humoral and/or cellular immune response against the specific antigen (and, thus, against the tumor or infectious organism). It is important to stress that in this approach, direct targeting of a tumor or direct targeting of an infectious agent by the antibody fusion proteins is not a requirement to trigger an antitumor activity or immune activity against the infectious agent. For example, mixing an antibody-immunostimulant fusion protein with its specific antigen (e.g., extracellular domain of HER2/neu ($ECD^{HER2}$) in Example I) is enough to elicit a potent cellular and humoral immune response that results in an strong antitumor activity (i.e., the fusion protein of the invention stimulates an endogenous humoral/cellular immune response).

It will be appreciated that, as explained throughout, not only can different immunostimulant, antibody combinations be used against different diseases/conditions, but that in various embodiments, different combinations of antibody-immunostimulant fusion proteins can be used in conjunction with each other. For example, in some treatment regimens different antibody-immunostimulant fusions can be administered to a subject in the same course of treatment (e.g., as was done with the IgG3-IL-2, IgG3IL-12, etc. in Example I below) to produce a synergistic effect in stimulating an immune response. Additionally, in some optional embodiments, different antigens on the same tumor or infectious agent are targeted in the same course of treatment. For example, two or more surface antigens on an infectious bacterium are optionally targeted by two or more different antibody-immunostimulant fusion proteins of the invention.

As will become apparent upon examination of the following, the use of the methods, compositions, etc. of the current invention allow for time saving in the treatment of subjects. Quick responses and actions can be of utmost importance in treatment of many conditions (e.g., in treatment of late stage cancers, advanced bacterial infections, etc.). For example, the use of antibody fusion proteins as an adjuvant of an antigen vaccine takes advantage of the high affinity of an antibody for its antigen. Thus use of the invention is a straightforward way to combine a disease related antigen with an immunostimulant (e.g., a cytokine or other immunostimulatory molecule), thus, avoiding the need to construct antibody fusion proteins consisting of an antigen genetically fused to an immunostimulant (e.g., a cytokine or other immunostimulants). Such fusions can be cumbersome and sometimes can lead to the decrease or loss of activity of one or both of the covalently conjugated partners (i.e., loss or decrease of activity of the antibody or of the immunostimulant). In addition, the use of antibody-immunostimulant fusion protein as in the invention is the only way to target circulating antigens (e.g., shed soluble HER2/neu in vivo, soluble antigens from infectious microorganisms, etc.). Of course, once again, it will be appreciated that the benefits of the use of the current invention in treating HER2/neu presenting cancers and *Staphylococcus aureus* infections (as used as examples herein) accrues to treatment of many other disease states, infections, cancers, etc. as will be apparent from the information herein.

All of the exemplary proteins used herein to illustrate the properties of the invention (e.g., anti-HER2/neu IgG3-(IL-2), anti-HER2/neu IgG3-(IL-12), anti-HER2/neu IgG3-(GMCSF)) were determined to be properly assembled and secreted. Thus, the fusion proteins migrated on SDS-PAGE with the expected molecular weight under both reducing and non-reducing conditions. Furthermore, they bound the appropriate antigen and carried out ligand and antibody-related activities. More importantly, direct treatment (e.g., intravenous (i.v.) injection or other methods of application) with the exemplary antibody fusion proteins resulted in significant antitumor activity in murine tumor models expressing human HER2/neu under conditions in which the antibody alone (anti-HER2/neu IgG3 containing the same variable region) failed to confer protection (see, below, and Peng et al., 1999; Dela Cruz et al., 2000; Penichet et al., 2001, all supra).

One non-limiting example of the current invention includes using the antibody-cytokine fusion proteins (anti-HER2/neu IgG3-(IL-2), anti-HER2/neu IgG3-(IL-12), and anti-HER2/neu IgG3-(GMCSF)) as immunoenhancers for $ECD^{HER2}$ vaccination in animal models (see, below for a more detailed protocol description). It will be appreciated that $ECD^{HER2}$ comprises the extracellular domain of HER2neu (e.g., the domain shed by tumor cells; recombinant versions used in examples herein equate to such shed extracellular domain in subjects). In brief, mice were vaccinated with either human $ECD^{HER2}$, $ECD^{HER2}$ in combination with anti-HER2/neu antibody, or $ECD^{HER2}$ with each anti-HER2/neu antibody-cytokine fusion protein (separately). After a booster, mice were challenged with a syngeneic carcinoma which expressed the rat HER2/neu protein (TUBO). There was a significant retardation of tumor growth rate and an increase in long-term survivors in those mice vaccinated with $ECD^{HER2}$ plus all three antibody-cytokine fusion proteins as compared to the mice in the control groups (i.e., PBS, $ECD^{HER2}$ or $ECD^{HER2}$ plus anti-HER2/neu antibody). Increased $ECD^{HER2}$ specific antibody titer was detected in mice vaccinated with the $ECD^{HER2}$ plus antibody-immunostimulant fusion proteins as compared to the control groups. The group that was vaccinated with $ECD^{HER2}$ plus antibody-(GMCSF) showed the highest antibody titer. Immune sera from the mice showed significant in vitro anti-proliferative activity against SK-BR-3 (a human breast cancer which overexpresses HER2/neu). The level of inhibition of SK-BR-3 correlated with the level of anti-$ECD^{HER2}$ antibody. In addition, mice vaccinated with $ECD^{HER2}$ plus antibody-immunostimulant fusion proteins produced increased level of $ECD^{HER2}$ specific IgG2a antibodies, indicating that a $T_H1$ type immune response was elicited. When incubated with soluble $ECD^{HER2}$, splenocytes from mice vaccinated with $ECD^{HER2}$ plus antibody-(GMCSF) fusion proteins demonstrated significant stimulation and IFN-γ secretion as compared with the other groups. These results indicate that both humoral and cell-mediated responses are elicited by the compositions of the current invention and, thus contribute to the observed anti-tumor activity. The current results also indicate that anti-HER2/neu antibody-cytokine fusion proteins can be effective prophylactic and therapeutic agents against HER2/neu expressing tumors in patients (see, below). Once again, it is to be appreciated that the discussion of anti-HER2/neu antibody-immunostimulant fusion proteins is used as an illustration of the general class of antibody-immunostimulant fusion proteins that are used as adjuvants of protein vaccinations in the current invention.

In certain examples herein murine GMCSF and murine IL-12 were used because human GMCSF and human IL-12 are not active in mice. Using murine GMCSF and IL-12 in the fusion proteins examples herein allowed testing of the invention in murine models. Such constructions should not be taken to be limiting, and thus, the invention is applicable to other animal systems (e.g., human, etc.) and other animal molecules (e.g., human GMCSF, human IL-12, etc.). Additionally, in the illustrations herein, human IgG3 was used, however, any immunoglobulin isotype can be used (see, above). Moreover, the concepts of the invention can be directly applied to other kinds of antibody frameworks, including scFv, etc. See, above.

Discussion of Example I

Example I illustrates that immunization of mice with (ECD$^{HER2}$) plus antibody-cytokine fusion proteins results in a potent activation of both arms of the immune response: cellular ($T_H1$) and humoral ($T_H2$). This activation is associated with a significant antitumor activity when immunocompetent mice were challenged with HER2/neu expressing tumors. Optionally, such effects possibly occur though the antibody-immunostimulant (e.g., cytokine) fusion proteins target and deliver ECD$^{HER}$ into dendritic cells, DCs, (or into other antigen presenting cells (APCs) through the interaction of the antibody-cytokine fusion proteins with DC surface receptors such as GMCSF, IL-2, IL-12 receptors as illustrated in FIG. 2, and/or optionally through contribution per se of the antibody-immunostimulant fusion proteins to the enhancement of the immune response against the targeted antigen (disease related antigen), e.g., IL-2 cell proliferative signal, GMCSF APC activation, IL-12 deviation to $T_H1$, etc. As explained above, the optional mechanisms of action for the methods and compositions of the current invention should not be construed as limiting, nor should they be construed as limiting upon the efficaciousness or scope of the methods and compositions of the invention.

In Example I, the methods and compositions of the invention are illustrated through use against tumors expressing HER2/neu proteins. The HER2/neu proto-oncogene (also known as c-erbB-2) encodes a 185 kDa transmembrane glycoprotein receptor known as HER2/neu or p185$^{HER2}$ that has partial homology with the epidermal growth factor receptor and shares with that receptor intrinsic tyrosine kinase activity. See, Coussens et al., 1985 "Tyrosine kinase receptor with extensive homology to EGF receptor shares chromosomal location with neu oncogene" *Science* 230:1132-9; Akiyama et al., 1986 "The product of the human c-erbB-2 gene: a 185-kilodalton glycoprotein with tyrosine kinase activity" *Science* 232:1644-6; and Stern et al., 1986 "p185, a product of the neu proto-oncogene, is a receptorlike protein associated with tyrosine kinase activity" *Mol Cell Biol* 6:1729-40. It consists of three domains: a cysteine-rich extracellular domain, a transmembrane domain and a short cytoplasmic domain (see, e.g., Coussens, Akiyama, and Stem all, supra). Overexpression of HER2/neu is found in 25-30% (or 20-40% in other studies) of human breast cancer. (see, Hayes, et al. 2001 "Circulating HER-2/erbB-2/c-neu (HER-2) extracellular domain as a prognostic factor in patients with metastatic breast cancer: Cancer and Leukemia Groups B Study 8662" *Clin Cancer Res* 7:2703) as well as in ovarian, endometrial, non-small-cell lung, gastric, bladder, prostate (see, e.g., Esserman, et al. 2001 "Vaccination with the extracellular domain of p185 neu prevents mammary tumor development in neu transgenic mice" *Cancer Immunol Immunother* 47:337) and lung cancer (see, e.g., Kaptain, et al. 2001 "Her-2/neu and breast cancer" *Diagn Mol Pathol* 10:139). This overexpression may be 100 fold higher than in normal tissues as a result of HER2/neu gene amplification (see, e.g., Yarden, 2001 "Biology of HER2 and its importance in breast cancer" *Oncology* 61:1). The HER2/neu overexpression is an independent predictor of both relapse-free and overall survival in breast cancer patients. See, e.g., Slamon et al., 1987 "Human breast cancer: correlation of relapse and survival with amplification of HER-2/neu oncogene" *Science* 234:177-82; Slamon et al., 1989 "Studies of the HER-2/neu proto-oncogene in human breast and ovarian cancer" *Science* 244:707-12; Press et al., 1993 "Amplification and overexpression of HER-2/neu in carcinomas of the salivary gland: correlation with poor prognosis" *Cancer Res* 54:5675-82; and Seshadri et al., 1993 "Clinical significance of HER-2/neu oncogene amplification in primary breast cancer" *J Clin Oncol* 11:1936-42. Overexpression of HER2/neu also has prognostic significance in patients with ovarian cancer (see, Slamon et al., 1989, supra), gastric cancers (see, Yonemura et al., 1991, "Evaluation of immunoreactivity for erbb-2 protein as a marker of poor short term prognosis in gastric cancer" *Cancer Res* 51:1034-1038), endometrial cancer (see, Berchuck et al., 1991 "Overexpression of HER-2/neu in endometrial cancer is associated with advanced stage disease" *Am J Obstet Gynecol* 164:15-21), and salivary gland cancers (see, Press et al., 1994 "Amplification and overexpression of HER-2/neu in carcinomas of the salivary gland: correlation with poor prognosis" *Cancer Res* 54:5675-82). The increased occurrence of visceral metastasis and micrometastatic bone marrow disease in patients with HER2/neu overexpression has suggested a role for HER2/neu in metastasis (see, Pantel et al., 1993 "Differential expression of proliferation-associated molecules in individual micrometastatic carcinoma cells" *J Nat Cancer Inst* 85:1419-1424; and Kallioniemi et al., 1994 "Association of c-erbB-2 protein over-expression with high rate of cell proliferation, increased risk of visceral metastasis and poor long-term survival in breast cancer" *Int J Cancer* 49:650-5).

The HER2/neu is thought to function as a growth factor receptor and play a role in cell differentiation, adhesion and motility. See, e.g., Kaptain, supra. Studies suggest that overexpression of HER2/neu plays a direct role in the pathogenesis and aggressiveness of tumors (see, Kaptain, supra) and, again, is associated with a poor clinical outcome in patients with newly diagnosed primary breast cancer (see, Hayes, supra). At present, treatment of patients with advanced HER2/neu-expressing breast cancer, with the anti-HER2/neu antibody (Ab), Trastuzumab (Herceptin, Genentech, San Francisco, Calif.), can lead to an objective response. See, Kaptain, supra. Chemotherapy can synergize with Trastuzumab to enhance its anti-tumor activity. However, a positive response is observed in only a subset of patients (see, Kaptain, supra) and additional modalities designed to improve clinical outcome are still needed.

The elevated levels of the HER2/neu protein in malignancies along with the extracellular accessibility of this molecule, and the occasional tumor shedding of soluble ECD HER2/neu (as well as the seriousness and prevalence of the cancers it is associated with) make HER2/neu an excellent tumor-associated antigen (TAA) for tumor specific vaccinations. Unfortunately, however, immunizations using HER2/neu protein have been highly disappointing in animal (non-human) models. For example, see, e.g., Disis, M. L., and K. Schiffman. 2001 "Cancer vaccines targeting the HER2/neu oncogenic protein" Semin Oncol 28:12. Also, while some success has been achieved in use of antibody-cytokine fusions which directly target tumor cells (e.g., IL-2 antibody fusion protein with the variable region of Herceptin, see, e.g., Penichet 2001 (Human Antibodies), supra, Peng, 1999, supra, and Dela Cruz 2000, supra) such antibodies have drawbacks in treatment of certain tumors (e.g., lack of access to the tumor due to poor vascularization, lack of access to the tumor due to binding of the antibodies to shed antigens, etc.). Of course, such previous antibody-cytokine tumor treatments also are not adaptable to treatment (either therapeutic or prophylactic) of diseases/conditions due to infectious agents such as viruses, bacteria, etc.

HER2/neu has become an attractive target for active immunotherapy due to its low expression in normal tissues and its overexpression in many different type of cancers. See, Kaptain, supra. A vaccine specific for the HER2/neu protein will have wide application in the treatment and/or prevention of many different human malignancies. See, e.g., Disis, et al 2001 "Clinical translation of peptide-based vaccine trials: the HER-2/neu model" Crit Rev Immunol 21:263. Indeed, DNA-based vaccines have previously been shown to induce protective immunity against rat HER2/neu (neu) expressing tumors in neu transgenic animals. See, e.g., Rovero, et al. 2000 "DNA vaccination against rat her-2/Neu p185 more effectively inhibits carcinogenesis than transplantable carcinomas in transgenic BALB/c mice" J Immunol 165:5133; Lachman, et al. 2001 "DNA vaccination against neu reduces breast cancer incidence and metastasis in mice" Cancer Gene Ther 8:259; Chen et al, 1998 "DNA vaccines encoding full-length or truncated Neu induce protective immunity against Neu-expressing mammary tumors" Cancer Res 58:9165; and Pupa, et al. "Prevention of spontaneous neu-expressing mammary tumor development in mice transgenic for rat proto-neu by DNA vaccination" Gene Ther 8:75. Peptide-based vaccines of HER2/neu were also able to "break" tolerance and generate anti-tumor activity in animal models. See, e.g., Nagata, et al. 1997 "Peptides derived from a wild-type murine proto-oncogene c-erbB-2? HER2/neu can induce CTL and tumor suppression in syngeneic hosts" J Immunol 159:1336; and Disis, et al. 1996 "Peptide-based, but not whole protein, vaccines elicit immunity to HER-2/neu, oncogenic self-protein" J Immunol 156:3151. However, rats immunized with neu in incomplete Freund's adjuvant showed no neu specific response (see, Disis, 1996 supra). Immunization of rats with the human HER2/neu ECD protein did mount an immune response to neu (see, Taylor, et al., 1996 "Humoral and cellular responses raised against the human HER2 oncoprotein are cross-reactive with the homologous product of the new proto-oncogene, but do not protect rats against B104 tumors expressing mutated neu" Cancer Immunol Immunother 42:179), suggesting that foreign proteins with high homology to "self" tumor antigens, may be effective in generating a response to "self" tumor antigens (see, Disis, et al., 1998 "HER-2/neu oncogenic protein: issues in vaccine development", Crit Rev Immunol 18:37) although it did not confer protection against a neu expressing tumor (see, Taylor, supra). Thus, breaking of tolerance to a self tumor antigen may not be sufficient to confer tumor protection. This was also demonstrated in immunocompetent mice that did not reject syngeneic tumors expressing a xenogenic and immunogenic human HER2/neu protein. See, Foy, et al. 2001 "Vaccination with Her-2/neu DNA or protein subunits protects against growth of a Her-2/neu-expressing murine tumor" Vaccine 19:2598; Shiku, et al. 2000 "Development of a cancer vaccine: peptides, proteins, and DNA" Cancer Chemother Pharmacol 46:S77; and Penichet, et al. 1999 "In vivo properties of three human HER2/neu-expressing murine cell lines in immunocompetent mice" Lab Anim Sci 49:179. Notably, vaccination with human HER2/neu intracellular domain (ICD) and extracellular domain (ECD) both elicited detectable immune responses, however only mice vaccinated with HER2/neu ICD showed anti-tumor activity (see, Foy, supra). Thus illustrating that elicitation of an immune response does not necessarily lead to an anti-tumor response. Therefore, in addition to breaking tolerance, the enhancement of the appropriate response is essential for generating protection against tumor growth.

Although some levels of humoral and cellular immunity against the tumor-associated antigen (TAA), HER2/neu, have been shown to be present in patients with HER2/neu bearing malignancies. See, Disis, et al., 1998 "HER-2/neu oncogenic protein: issues in vaccine development" Crit Rev Immunol 18:37; Yip, et al., 2001 "Identification of epitope regions recognized by tumor inhibitory and stimulatory anti-ErbB-2 monoclonal antibodies: implications for vaccine design" J Immunol 166:5271; and Disis, M. L., et al., 2001 "Cancer vaccines targeting the HER2/neu oncogenic protein" Semin Oncol 28:12. Such immunity is clearly not sufficient to provide patients with protection. While, it has been anticipated that augmenting pre-existing immunity may have therapeutic effects (see, Disis 1998, supra), recent clinical trials aimed at boosting immunity to HER2/neu using peptide or peptide-pulsed dendritic cell (DC)-based vaccines, have yet to show clinical efficacy. See, e.g., Disis 1999, "Generation of immunity to the HER-2/neu oncogenic protein in patients with breast and ovarian cancer using a peptide-based vaccine" Clin Cancer Res 4:1289+; Brossart, P., et al., 2000 "Induction of cytotoxic T-lymphocyte responses in vivo after vaccinations with peptide-pulsed dendritic cells" Blood 96:3102; and Murray, J. et al., 2000 "Clinical trials of HER-2/neu-specific vaccines" Semin Oncol 27:71. Thus, vaccine modalities targeting the HER2/neu protein that are designed not only to break immune tolerance and boost pre-existing immunity, but also to generate an immune response that can eradicate the cancer, are still needed. Hence the methods, compositions, etc. of the current invention are applicable in treatment of disease states such as HER2/neu presenting cancers.

It has been suggested that the low immunogenicity of $ECD^{HER2}$ is related to the improper uptake and trafficking of the $ECD^{HER2}$ in dendritic cells (DCs), which results in deficient MHC class II presentation. See, Hiltbold et al., 2000, "The mechanism of unresponsiveness to circulating tumor antigen MUC1 is a block in intracellular sorting and processing by dendritic cells" J Immunol 165:3730-41. However, the optional interaction illustrated in FIG. 2 (e.g., the concepts of the current invention wherein the antibody-immunostimulant complexed with the antigen interacts with an APC or DC) optionally changes the quantity and/or quality of antigen presentation, which results in a strong T and B cell immune response against tumors expressing HER2/neu. Additionally, the optional general immunostimulatory activity of the immunostimulant (e.g., cytokines) which are fused to the antibody fusion proteins of the invention optionally contribute per se to the enhancement of the immune response against the targeted antigen (e.g., IL-2-cell proliferative signal, GMCSF-APC activation and IL-12-deviation to $T_H1$). Once again, such optional mechanisms of action should not be taken as limiting, see, above.

The elicited immune response (i.e., produced through use of the methods, etc. of the current invention) is against the HER2/neu expressed on the surface of cancer cells (humoral immune response) as well as against HER2/neu peptides associated with MHC class I on the surface of cancer cells (cellular immune response). Again, the current invention additionally elicits humoral and/or cellular immune responses against other antigens/tumors/cells when such antigens, etc. are targeted in different embodiments. In Example I, since HER2/neu has high homology with other growth factor receptors such as epidermal growth factor receptors 1, 2, and 3 (EGF1, EGF2, EGF3), the elicited immune response (humoral and/or cellular) will be directed not only against the targeted antigen (HER2/neu), but also against other homologous receptors that are expressed on the cancer cell.

In the illustrated Example I, the efficacy of anti-HER2/neu antibody-immunostimulant fusion proteins as adjuvants of $ECD^{HER2}$ protein vaccination was examined. While it has been suggested that immunization with the HER2/neu protein may lead to detrimental effects through inducing antibodies which stimulate tumor cell growth (see, Yip, supra), no such activity was observed in the use of the invention. Instead, vaccination with all antibody-immunostimulant fusion proteins, provided mice significant protection against murine cells that do not express the human HER2/neu but do express the rat neu protein (TUBO). In other words, TUBO cells express the rat neu protein and vaccinated mice were protected against such. See, below. Although the in vitro growth of TUBO cells was not affected by anti-$ECD^{HER2}$ antibodies, SK-BR-3 cells were growth inhibited, with the strongest inhibition observed when sera containing high levels of anti-$ECD^{HER2}$ IgG were used. Although a similar degree of anti-tumor activity was generated using the three different antibody-immunostimulant fusion proteins, analysis of the antibody and cellular immune responses suggested that these highly protective regimens function through different pathways. Also, the above illustrates that the immune response generated through the invention can also optionally produce responses against closely related and/or similar antigens. See, Example I, below.

In Example I, quality and magnitude of the anti-$ECD^{HER2}$ antibody response depended on the immunization schedule. Enhanced $T_H2$ (see, Su, et al., 2002 "IL-12 is required for antibody-mediated protective immunity against blood-stage Plasmodium chabaudi AS malaria infection in mice" *J Immunol* 168:1348) anti-$ECD^{HER2}$ IgG1 response was present only in mice vaccinated with IgG3-(GMCSF) and $ECD^{HER2}$ plus IgG3-(IL-2). Mice vaccinated with $ECD^{HER2}$ plus IgG3-(L-12) showed enhanced $T_H1$ (see, Su, supra) anti-$ECD^{HER2}$ IgG2a and IgG3 responses, while modest responses were elicited in mice vaccinated $ECD^{HER2}$ plus IgG3-(IL-2). Lesser IgG2 and IgG3 responses were elicited in mice vaccinated $ECD^{HER2}$ plus IgG3-(GMCSF). Transfer of sera obtained from these regimens indicates that protection against TUBO can be mediated through a humoral pathway. Characterization of the transferred immune sera suggested the quality and magnitude of the anti-$ECD^{HER2}$ antibody response may be important for tumor protection, (e.g., anti-$ECD^{HER2}$ IgG1 levels, for example, showed no correlation with the level of tumor protection). The observation that anti-$ECD^{HER2}$ IgG2a levels in unprotective serum from mice vaccinated with $ECD^{HER2}$ alone was comparable to protective serum from mice vaccinated with $ECD^{HER2}$ plus IgG3-(IL-2) suggested that tumor protection was not mediated through anti-$ECD^{HER2}$ IgG2a. Nevertheless, the levels of anti-$ECD^{HER2}$ IgG3 did correlate with the level of protection, suggesting its involvement in the observed protection. However, of course, such does not rule out that protection through anti-$ECD^{HER2}$ IgG1 or IgG2a may ensue in other immunological conditions using the invention.

In Example I, the magnitude of splenocyte proliferation and secretion of IFN-γ in the presence of soluble $ECD^{HER2}$, depended on the vaccination regimen. This implied that unique cellular immune repertoires were generated in vaccinated mice, thus, suggesting their importance in the observed protection against a challenge with TUBO. In fact, an inverse correlation with the ability of immune sera to protect naïve mice was found with the level of cellular activation. For example, transferred serum pooled from mice vaccinated with $ECD^{HER2}$ plus IgG3-(IL-12), but not of mice vaccinated with $ECD^{HER2}$ plus IgG3-(GMCSF) provided the strongest protection to naïve mice. However, splenocytes of mice vaccinated with $ECD^{HER2}$ plus IgG3-(GMCSF), but not of mice vaccinated with $ECD^{HER2}$ plus IgG3-(IL-12) showed amplified response to soluble $ECD^{HER2}$, thus indicating that the activation of a cellular response can be required in conditions in which protection through a humoral pathway is not sufficient.

Altogether, the results indicate that protection of mice vaccinated with $ECD^{HER2}$ plus IgG3-(IL-12) was primarily mediated through a humoral pathway, while protection of mice vaccinated with $ECD^{HER2}$ plus IgG3-(GMCSF) included the involvement of a cellular response. Additionally, the protection of mice vaccinated with $ECD^{HER2}$ plus IgG3-(IL-2) was dependent on both humoral and cellular responses. These results thus indicate that the combination of both humoral and cellular responses synergizes to mount a more potent anti-tumor response. Such was optionally the case in mice vaccinated with $ECD^{HER2}$ plus IgG3-(IL-2) wherein five mice were tumor free 19 days after a challenge with TUBO, compared to three mice in $ECD^{HER2}$ plus IgG3-(IL-12) or $ECD^{HER2}$ plus IgG3-(GMCSF) vaccinated mice and none in the control groups.

IFN-γ induced activation of cytotoxic effector cells is optionally necessary to potentiate an anti-tumor response against TUBO. In vivo, upon challenge of vaccinated mice with TUBO cells, APCs within the tumor microenvironment can process TUBO cell antigens, including the rat neu protein (with >90% homology to human HER2/neu (see, Taylor, et al., 1998 "Manipulation of the immune response of mice against neu/HER2-expressing tumours" *Oncol Rep* 5:1535), and present the antigens to $ECD^{HER2}$ primed T-cells. It seems indicated, based on the in vitro cellular assays, that in those mice vaccinated with $ECD^{HER2}$ plus IgG3-(GMCSF) and $ECD^{HER2}$ plus IgG3-(IL-2), that robust secretion of IFN-γ by activated T-cells induces the cytotoxic potential of effector cells such as granulocytes, macrophages, and monocytes (see, e.g., Arai, et al., 1990 "Cytokines: coordinators of immune and inflammatory responses" *Annu Rev Biochem* 59:783; Chen, et al., 1995 "Monocyte-mediated lysis of acute myeloid leukemia cells in the presence of the bispecific antibody 251×22 (anti-CD33×antiCD64)" *Clin Cancer Res* 1:1319; and Vaickus, et al., 1990 "Interferon gamma augments Lym-1-dependent, granulocyte-mediated tumor cell lysis" *Blood* 75:2408), as well as the upregulation of FcγRI receptors (see, e.g., Chen, supra; Vaickus, supra; Hartnell, et al., 1992 "IFN-gamma induces expression of Fc gamma RIII (CD16) on human eosinophils" *J Immunol* 148:1471; te Velde, et al., 1992 "IL-10 stimulates monocyte Fc gamma R surface expression and cytotoxic activity. Distinct regulation of antibody-dependent cellular cytotoxicity by IFN-gamma, IL-4, and IL-10" *J Immunol* 149:4048; Anselmino, et al., 1989 "Human basophils selectively express the Fc gamma RII (CDw32) subtype of IgG receptor" *J Allergy Clin Immu-* nol 84:907; Buckle, et al., 1989 "The effect of IFN-gamma and colony-stimulating factors on the expression of neutrophil cell membrane receptors" *J Immunol* 143:2295; and, Klebanoff, et al., 1992 "Effects of gamma-interferon on human neutrophils: protection from deterioration on storage" *Blood* 80:225) that is selectively utilized by murine IgG2a antibodies in antibody-dependent cellular cytotoxicity (ADCC) (see, e.g., Rodolfo, et al., 1998 "IgG2a induced by interleukin (IL) 12-producing tumor cell vaccines but not IgG1 induced by IL-4 vaccine is associated with the eradication of experimental metastases" *Cancer Res* 58:5812). Thus it is possible to mount a protective response against TUBO with relatively low anti-ECD$^{HER2}$ IgG2a levels as detected in mice vaccinated with ECD$^{HER2}$ plus IgG3-(GMCSF), on the condition that effector cells have an increased number of FcγRI receptors to mediate an effective ADCC. Indeed, in vitro, IFN-γ induced augmentation of ADCC via a murine IgG2a antibody was speculated to be the effect of FcγRI induction (see, Vaickus, supra). Also activated effector cells are optionally targeted to TUBO by anti-ECD$^{HER2}$ antibodies. Such can explain the weaker protective effect of transferred sera containing high levels of anti-ECD$^{HER2}$ IgG due to sub-optimal or otherwise lacking activated effector cells in naïve mice. Indeed, implanted TUBO, in protected neu-DNA vaccinated mice, was heavily infiltrated with PMNs and it has been suggested to have been mediated through elicited anti-neu antibodies (see, Rovero, supra).

Vaccine strategies (e.g., including those of the current invention) targeting HER2/neu might be more effective in the treatment of patients with HER2/neu expressing cancers than the passive infusion of monoclonal anti-HER2/neu antibodies. One drawback of passive monoclonal antibody infusion is that it is short-lived in circulation (see, Disis 2001, supra), which can lessen its therapeutic potential. Optimal circulating levels of Trastuzumab were found to be essential to induce a clinical response in patients (see, Baselga, et al., 1996 "Phase II study of weekly intravenous recombinant humanized anti-p185HER2 monoclonal antibody in patients with HER2/neu-overexpressing metastatic breast cancer" *J Clin Oncol* 14:737). Therefore an effective vaccine targeting HER2/neu should provide an active continuous supply of anti-HER2/neu antibodies (see, Disis 2001, supra) including HER2/neu directed cellular responses that should lead to a more effective immunity to HER2/neu malignancies. The native nature of an endogenous humoral response should circumvent any additional drawback of immunogenicity that limits the long term use of monoclonal antibodies (see, Disis 2001, supra).

The current invention provides protein vaccinations with whole ECD$^{HER2}$ using immunoenhancing antibody-immunostimulants (e.g., cytokines, etc.) as adjuvants, and as the examples herein illustrate, provides potent anti-tumor activity in animal models. The anti-tumor activity is optionally optimized herein through definition of optimal dose and schedule of regimens and potential synergism among different antibody-immunostimulant fusion proteins. Also optionally, the possible interaction between antibody-immunostimulant fusion proteins and the disease related antigen (e.g., the soluble ECD$^{HER2}$ herein) at vaccinations is examined and optimized herein to help in, e.g., tumor protection, etc. However, whether such optional interaction of the antibody-immunostimulant and the disease-related antigen is required, anti-HER2/neu antibody-immunostimulant fusion proteins can be used as adjuvants of disease related antigen protein vaccination in the therapy of patients (e.g., anti-HER2/neu with HER2/neu expressing tumors, etc.). See, e.g., Harvill, et al., 1996 "In vivo properties of an IgG3-IL-2 fusion protein. A general strategy for immune potentiation" *J Immunol* 157:3165 indicating that interaction between dansylated BSA and the anti-dansyl-(IL-2) antibody-fusion protein was necessary to enhance an anti-BSA antibody response.

Discussion of Example II

In addition to use as an anti-tumor treatment (either therapeutically and/or prophylactically) the methods and compositions of the invention are also optionally used as treatment (again, either therapeutically and/or prophylactically) against infectious disease agents (e.g., as treatment for viral, bacterial, mycoplasmal, fungal, prion, or parasitical infections, etc.). Such use is illustrated in Example II (see, below) using the bacterium *Staphylococcus aureus*.

*Staphylococcus aureus*, a gram positive bacterium, is common cause of community-acquired infections and is the most frequently isolated bacterial pathogen in hospital-acquired infections that result in a high mortality. See, e.g., Nickerson et al., 1995 "Mastitis in dairy heifers: initial studies on prevalence and control" *J Dairy Sci* 78:1607-18; Lowy, 1998 "*Staphylococcus aureus* infections" *N Engl J Med* 339:520-32; McKenney et al., 1999 "Broadly protective vaccine for *Staphylococcus aureus* based on an in vivo-expressed antigen" *Science* 284:1523-7; and Lorenz et al., 2000 "Human antibody response during sepsis against targets expressed by methicillin resistant *Staphylococcus aureus*" *FEMS Immunol Med Microbiol* 29:145-53. Among the human diseases caused by *Staphylococcus aureus* are pneumonia, endocarditis, osteomyelitis, septic arthritis, postoperative wound infections, septicemia, and toxic shock syndrome. See, e.g., Nickerson et al., supra; Lowy, supra; McKenney et al., supra; and Lorenz et al., supra. Additionally, *Staphylococcus aureus* is also a significant pathogen in economically important animals. See, e.g., Nickerson et al., supra; and McKenney et al., supra. Additionally, some strains of the bacterium are resistant to first-line drugs such as synthetic penicillins (e.g., methicillin). Methicillin-resistant *Staphylococcus aureus* (MRSA) strains are found in 40-60% of staphylococcal isolates in large hospitals. See, e.g., Nickerson et al., supra; Lowy, supra; and McKenney et al., supra. Of even greater concern, however, is the recent emergence of MRSA strains with reduced susceptibility to vancomycin, the so-called antibiotic of last resort. See, e.g., McKenney et al., supra. The appearance of these vancomycin-resistant (or intermediate) *Staphylococcus aureus* (VISA) strains raises the specter of untreatable staphylococcal infections. Thus, alternative strategies to treat *Staphylococcus aureus* infection are urgently need, and the bacterium presents an ideal target to illustrate the methods and compositions of the invention.

*Staphylococcus aureus* protein A (SpA), is a 42-kDa protein present in 95% of all *Staphylococcus aureus* strains. The protein contains five highly homologous extracellular Ig-binding domains in tandem, designated domains E, D, A, B, and C (see, e.g., Boyle, 1990, in Bacterial Immunoglobulin-Binding Proteins, ed. Boyle, M. P. D. (Academic, San Diego), Vol. 1, pp. 17-28; and Graille et al., 2000 "Crystal structure of a *Staphylococcus aureus* protein A domain complexed with the Fab fragment of a human IgM antibody: structural basis for recognition of B-cell receptors and superantigen activity" *Proc Natl Acad Sci USA* 97:5399-404). It exists in both secreted and membrane-associated forms, and although the mechanism(s) are not defined, experimental models indicate that secreted protein A (SpA) enhances staphylococcal virulence (see, e.g., Patel et al., 1987 "Virulence of protein A-deficient and alpha-toxin-deficient mutants of *Staphylococcus aureus* isolated by allele replacement" *Infect Immun* 55:3103-10; and Graille et al., 2000, supra).

Protein A possesses two distinct antibody-binding activities: first, each binding domain can bind Fc (the constant region of IgG involved in effector functions) and, second, the domains can bind Fab (the antibody fragment responsible for antigen recognition). See, e.g., Boyle, supra; and Graille et al., supra. The Fc binding site (i.e., where protein A binds to the antibody) has been localized to the elbow region at the $C_H2$ and $C_H3$ interface of most IgG subclasses. This binding property has been extensively used for the labeling and purification of antibodies (see, e.g., Tashiro, et al., 1995 "Structures of bacterial immunoglobulin-binding domains and their complexes with immunoglobulins" Curr Opin Struct Biol 4:471-81; and Graille et al., supra). The Fab binding specificity of protein A is less well characterized, but it has been shown to involve a site on the variable region of the antibody heavy chain. See, e.g., Vidal, et al., 1985 "Alternative mechanism of protein A-immunoglobulin interaction the $V_H$-associated reactivity of a monoclonal human IgM" J Immunol 135:1232-8; and Graille et al., supra. Correlation with antibody sequence usage indicates that the Fab binding specificity of protein A is restricted to products of the human variable region of the Fab heavy chain $V_H3$ family. The $V_H3$ family represents nearly half of inherited $V_H$ genes. See, e.g., Hillson et al., 1993 "The structural basis of germline-encoded $V_H3$ immunoglobulin binding to staphylococcal protein A" J Exp Med 178:331-6; and Graille et al., supra. The variable region of the Fab heavy chain ($V_H$) interacts with protein A through framework residues, without the involvement of the hypervariable regions implicated in antigen recognition.

The fact that protein A is present in most (if not all) *Staphylococcus aureus* strains, its role as a virulence factor, and its expression on the surface of the *Staphylococcus aureus* bacterium make protein A an excellent candidate for protein vaccination. As explained in Example II, below, the ability of antibody-immunostimulant fusion proteins used as adjuvants of protein vaccination to elicit a protective immune response was examined. See, below.

The ability to enhance an antibody response against both soluble and insoluble forms of protein A (i.e., free soluble protein a and protein A bound on the surface of Cowan I) is seen when mice are vaccinated with soluble protein A in the presence of IgG3-(IL-2) and IgG3-(GMCSF) antibody fusion proteins (with the necessity of a booster), see, below. Thus, the usefulness of the antibody fusion proteins lies with the fused immunostimulants (e.g., cytokines). The results indicate that the antibody fusion proteins are effective enhancers of an antibody immune response to protein A in mice, suggesting the potential use of this technology for the prevention and treatment of *Staphylococcus aureus* infection in both humans and animals.

EXAMPLES

The following examples utilize the HER2/neu antigen/antibody and various cytokines (e.g., IL-2, IL-12, GMCSF) as well as the protein A antigen from *Staphylococcus aureus*. However, once again, it is to be emphasized that the methods of the current invention (e.g., use of antibody-immunostimulant fusions as adjuvants of antigenic delivery) are applicable to many different combinations of antibodies and immunostimulants, etc., and are useful in the treatment of myriad diseases/conditions (i.e., not just for the treatment of HER2/neu presenting tumors or staphylococcal infections).

Example I

Anti-HER2/Neu Antibody Fusion Proteins as Effective Enhancers of Extracellular Domain HER2/Neu Protein Vaccination The molecule HER2/neu is overexpressed in a number of human cancers (e.g., breast, ovarian, prostate and lung cancers) and is associated with poor prognosis. As described above, some DNA and peptide based vaccines which target HER2/neu have elicited significant protection against HER2/neu expressing cancers in animal models. However, vaccines using the complete extracellular domain of HER2/neu ($ECD^{HER2}$) have not shown the same efficacy. As detailed herein, the current invention illustrates several anti-human HER2/neu antibody (Ab)-immunostimulant fusion proteins which contain the immunostimulatory cytokines: IL-2, IL-12 or GMCSF and their use (again, depending upon, e.g., the specific disease to be treated, the specific action to be potentiated, etc. different immunostimulatory molecules are optionally fused to construct the molecules used in the current invention).

The antibody-immunostimulant fusion proteins used in Example I (and also similar related fusions of the invention) retain both immunostimulant (e.g., cytokine) activity and the ability to bind HER2/neu. To determine if these antibody-immunostimulant fusion proteins act as immunoenhancers for $ECD^{HER2}$ vaccination, mice were vaccinated with either human $ECD^{HER2}$, $ECD^{HER2}$ with anti-HER2/neu antibody (IgG3), or $ECD^{HER2}$ with each antibody-immunostimulant fusion protein. After given a booster, mice were challenged with a syngeneic carcinoma that expressed the rat HER2/neu protein (i.e., TUBO). There was a significant retardation of tumor growth rate as well as in increase in long-term survivors in the groups of mice vaccinated with $ECD^{HER2}$ plus all three antibody-immunostimulant fusion proteins as compared to the mice in the control groups (i.e., those mice given PBS, $ECD^{HER2}$ or $ECD^{HER2}$ plus IgG3).

An anti-$ECD^{HER2}$ humoral immune response was detected in all vaccinated groups, with $ECD^{HER2}$ plus IgG3-(GMCSF) and $ECD^{HER2}$ plus IgG3-(IL-2) vaccinated mice showing enhanced levels. These two groups had increased level of anti-$ECD^{HER2}$ IgG1 and IgG2a antibodies, as compared to the control groups. These results indicate that both $T_H2$ and $T_H1$ immune responses were elicited. The mice vaccinated with $ECD^{HER2}$ plus IgG3-(IL-12) showed increased IgG2a antibodies but not IgG1 antibodies, indicating that a $T_H1$ immune responses was elicited (see, above).

Immune sera from the mice showed significant in vitro anti-proliferative activity against SK-BR-3 (a human breast cancer with overexpressed HER2/neu protein), with the level of inhibition correlated with the level of anti-$ECD^{HER2}$ antibody. When incubated with soluble $ECD^{HER2}$, splenocytes from mice vaccinated with $ECD^{HER2}$ plus antibody-(GMCSF) demonstrated significant proliferation and significant IFN-γ secretion as compared with the other groups. Such results indicate that the current invention (as illustrated by the example) elicits both humoral and cell-mediated responses. Thus, both the humoral and the cell-mediated immune responses can contribute to the observed anti-tumor activity (as seen in the current example). The current examples indicate that, through use of the current invention, it is possible to use anti-HER2/neu antibody-immunostimulant fusion proteins as adjuvants of protein vaccination as prophylactic and therapeutic regimens against, e.g., HER2/neu expressing tumors in patients. Importantly, patients who are unresponsive to other anti-HER2/neu antibody based treatments may benefit through use of the methods and compositions of the current invention (as illustrated in the current example). Once again, it is important to emphasize that other combinations of antibodies/immunostimulants/antigens can be targeted against different diseases, and are included in the current invention.

In the current example illustrating the invention, female BALB/c mice were vaccinated with the human $ECD^{HER2}$ protein in various compositions. Vaccinated mice were challenged with a transplantable carcinoma, TUBO, which overexpresses the rat neu protein. See, e.g., Rovero, S. A. et al. 2000, "DNA vaccination against rat her-2/Neu p185 more effectively inhibits carcinogenesis than transplantable carcinomas in transgenic BALB/c mice" *J Immunol* 165:5133. As seen below, mice immunized only with soluble $ECD^{HER2}$ showed only modest anti-tumor immunity compared to the control group. However, when the immuno-enhancing cytokines IL-2, IL-12 or GMCSF were fused to an anti-HER2/neu antibody (human IgG3) and used as vaccine adjuvants (i.e., as per the methods of the current invention), a remarkable enhancement of anti-tumor activity was seen. See, e.g., Peng, L. S., et al. 1999 "A single-chain IL-12 IgG3 antibody fusion protein retains antibody specificity and IL-12 bioactivity and demonstrates antitumor activity" *J Immunol* 163:250; Penichet, M. L., et al. 2001 "A recombinant IgG3-(IL-2) fusion protein for the treatment of human HER2/neu expressing tumors" *Hum Antibodies* 10:43; and Dela Cruz, J. S., et al. 2000 "Recombinant anti-human HER2/neu IgG3-(GMCSF) fusion protein retains antigen specificity and cytokine function and demonstrates antitumor activity" *J Immunol* 165:5112 for further information on anti-HER2 fusion proteins all of which are incorporated herein for all purposes.

Materials and Method

Mice

In the current example, female BALB/c mice 10-12 weeks of age obtained from Taconic Farms, Inc. (Germantown, N.Y.) were used. All experiments (both in Example I and Example II) were performed according to National Institutes of Health (NIH) (Bethesda, Md.) Guide for the Care and Use of Laboratory Animals.

Cell Lines

TUBO is a cloned cell line, which overexpresses the neu protein. The cell line was established from a lobular carcinoma that spontaneously arose in a BALB/c female mouse transgenic for the transforming rat neu oncogene driven by the mouse mammary tumor virus promoter. See, Rovero, S., et al, supra. TUBO cells grow progressively in normal BALB/c mice and give rise to lobular carcinomas which are histologically similar to those carcinomas that appear in BALB-neuT-transgenic mice, again, see, Rover, S., supra. In the current example, TUBO cells were cultured in Dubecco's Modified Eagle Medium (DMEM) supplemented with glutamax, glucose, 25 mM Hepes buffer, pyridoxine-HCl (GibcoBRL, Life Technologies, Rockville, Md.), and 20% fetal bovine serum (Atlas Biologicals, Fort Collins, Colo.). Also used in the current example was SK-BR-3, a human breast cancer cell line which overexpresses the HER2/neu protein (ATCC, Rockville, Md.). SK-BR-3 cells were cultured in Iscoves Modified Dubecco's Medium, IMDM, supplemented with L-glutamine, penicillin, and streptomycin with 5% bovine calf serum (Atlanta Biologicals, Norcross, Ga.).

Antibody-Immunostimulant Fusion Proteins and $ECD^{HER2}$

The construction, purification and analysis of biological activities of IgG3, IgG3-(GMCSF), IgG3-(IL-2) and IgG3-(IL-12) immunostimulant fusion proteins was described previously. See, Peng, L. S., et al. 1999 "A single-chain IL-12 IgG3 antibody fusion protein retains antibody specificity and IL-12 bioactivity and demonstrates antitumor activity" *J Immunol* 163:250; Penichet, M. L., et al. 2001 "A recombinant IgG3-(IL-2) fusion protein for the treatment of human HER2/neu expressing tumors" *Hum Antibodies* 10:43; and Dela Cruz, J. S., et al. 2000 "Recombinant anti-human HER2/neu IgG3-(GMCSF) fusion protein retains antigen specificity and cytokine function and demonstrates antitumor activity" *J Immunol* 165:5112 all of which are incorporated herein for all purposes. The IgG3 and antibody-immunostimulant fusion proteins used in this example contain the same variable region as the monoclonal anti-HER2/neu, Herceptin. BHK/erbB2, which is a cell line that secretes soluble human $ECD^{HER2}$ was provided by Dr. James D. Marks (University of California at San Francisco, San Francisco, Calif.). The soluble $ECD^{HER2}$ was purified from the BHK/erbB2 culture supernatants using affinity chromatography with IgG3 immobilized on Sepharose 4B (CNBr-activated Sepharose 4B, Amersham Pharmacia Biotech, Upsala, Sweden). All purified proteins were dialyzed against dialysis buffer (50 mM Tris base, 150 mM NaCl in deionized water at pH 7.8) and the concentrations were determined by bicinchoninic acid based protein assay (BCA protein Assay, Pierce Chemical Co., Rockford, Ill.). Prior to use, the proteins were analyzed by SDS-PAGE and Coomassie blue stained to assess purity, size and integrity.

Mice Vaccination and Challenge with TUBO

Two groups of eight mice were injected subcutaneously in their right flanks on day 0 and again on day 35 (week 5 "booster") with either 8 μg of $ECD^{HER2}$ alone, 8 μg of $ECD^{HER2}$ plus 14 μg of IgG3, 8 μg of $ECD^{HER2}$ plus 16 μg of IgG3-(GMCSF), 8 μg of $ECD^{HER2}$ plus 16 μg of IgG3-(IL-2), or 8 μg of $ECD^{HER2}$ plus 27 μg of IgG3-(IL-12). It will be appreciated that differing volumes of components were used in order to equalize the molarity to achieve 1:1 equivalence of binding units amongst the constituents of the composition. Antibody or antibody-immunostimulant fusion proteins were mixed with $ECD^{HER2}$ to allow a 1 $ECD^{HER2}$:1 F(ab')$_2$ ratio, at a concentration which allowed the injection of 150 μl per mouse. The mixtures were allowed to sit at 4° C. overnight prior to injection. Mice injected with a diluent (PBS) served as a control group. Three weeks after the booster (i.e., three weeks after day 35), one set of vaccinated mice in each vaccination group was challenged in the left flank with $10^6$ TUBO cells in 150 μl Hank's balanced salt solution, HBSS (GIBCOBRL, Life Technologies, Rockville, Md.). One out of the eight mice vaccinated with $ECD^{HER2}$ plus IgG3-(IL-2) died prior to a challenge with TUBO cells from a course unrelated to the vaccination.

Tumor growth in the mice was monitored and measured with a caliper beginning 7 days after the tumor challenge. Mice with tumors of 1.5 cm in diameter or greater were euthanized. On the same day the vaccinated mice were challenged with TUBO, blood (used in the serological studies and in passive transfer of immunity) and splenocytes were collected from the other group of unchallenged vaccinated mice and processed and used in additional studies described below.

Characterization of Murine Antibody Response to $ECD^{HER2}$

Sera obtained from mice 2 days prior to the challenge with TUBO or from the unchallenged vaccinated mice were analyzed by ELISA for antibodies to $ECD^{HER2}$. The ELISA was done using 96-well microtiter plates coated with 50 μl of ECD$^{HER2}$ at a concentration of 1 μg/ml. The plates were washed and blocked with 3% bovine serum albumin (BSA) (Sigma Chemical, St. Louis, Mo.) in PBS. After washing, dilutions of sera in PBS containing 1% BSA were added to the wells and incubated overnight at 4° C. Bound IgG was detected by incubating for 1 hour at 37° C. with AP-labeled rabbit anti-mouse IgG (Zymed, San Francisco, Calif.). After washing, p-nitrophenyl phosphate disodium dissolved in diethanolamine buffer (Sigma Chemical, St. Louis, Mo.) was added for 2 hours and the plates were read at 410 nm. Sera from naïve mice of the same age were used as a negative control. All ELISAs were performed in duplicate using an internal positive control curve for each plate. Murine anti-ECD$^{HER2}$IgG1, IgG2a and IgG3 responses were analyzed by ELISA using 96-well microtiter plates prepared as described above with AP-labeled rat anti-mouse IgG1, IgG2a (Zymed, San Francisco, Calif.) or AP-labeled goat anti-mouse IgG3 (Southern Biotechnology Associates, Inc., Birmingham, Ala.) used as detecting agents.

TUBO and SK-BR-3 In Vitro Proliferation Assay $5 \times 10^3$ TUBO cells or $2 \times 10^4$ SK-BR-3 cells in 100 μl of IMDM (supplemented with L-glutamine, penicillin, streptomycin and 5% bovine calf serum) were added to each well of a 96-well round bottom tissue culture plate. Pooled sera from each regimen of cells were depleted of complement by incubation at 56° C. for 30 minutes and then diluted in IMDM supplemented with L-glutamine, penicillin, streptomycin and 5% bovine calf serum, to give a final working dilution of 1:100 and 1:300. Immune sera in a volume of 100 μl were added to the TUBO cells or the SK-BR-3 cells to give a final volume of 200 μl/well. These cells where then incubated for 48 hours or 6 days, (TUBO and SK-BR-3 respectively), in a 5% $CO_2$, 37° C. incubator. Twelve hours prior to the end of the incubation period, the wells of the plates were pulsed with $^3$H-thymidine (ICN, Costa Mesa, Calif.) to give a final concentration of 5 μCi/ml. The cells were then harvested and passed through a glass-fiber filter (Wallac Oy, Turku, Finland) using a Micro Cell Harvester (Skatron, Norway). Any $^3$H-thymidine incorporation into DNA by actively growing cells was measured with a 1205 Betaplate Liquid Scintillation Counter (Wallac Oy, Turku, Finland). All of the assays were done in triplicate.

It should be noted that the use of fewer cells and a shorter incubation period was required for the TUBO cell in vitro assay, because of the rapid growth of TUBO cells in culture as compared to SK-BR-3 cells. Data herein are presented as $^3$H-thymidine (CPM) incorporation by TUBO cells or by SK-BR-3 cells after incubation with immune sera. IgG3, containing the same variable region as Herceptin, is effective in inhibiting the growth of SK-BR-3 in vitro, and was used as a positive control. No positive control was available for use with TUBO cells.

Transfer of Immune Sera

The mice were randomized and distributed into groups of 6 mice per group. At day −1, naïve mice received an intravenous injection of 175 μl of pooled immune sera. On day 0, $10^6$ TUBO cells in 150 μl of HBSS (GIBCOBRL, Life Technologies, Rockville, Md.), were injected in the right flank of the mice. An untreated group of mice of the same age was also challenged with TUBO cells. Tumor growth was monitored and measured with a caliper starting at day 7 and every three days until day 21.

Mouse Splenocyte Isolation, Stimulation with Soluble ECD$^{HER2}$ Protein and IFN-γ Quantification Spleens from vaccinated mice were removed, pooled and teased with two frosted specimen slides using aseptic techniques. Released splenocytes were passed through a 100 μm cell strainer (Becton Dickinson Labware, Franklin Lanes, N.J.) to remove large debris. Red blood cells (RBCs) were lysed in 0.85% ammonium chloride in deionized water. $5 \times 10^6$ splenocytes/ml/well were added into the wells of a 24-well tissue culture plate along with RPMI 1640 (Gibco-BRL, Life Technologies, Rockville, Md.) supplemented with 50 IU/ml of murine IL-2 (PeproTech, Inc., Rocky Hill, N.J.), 10% fetal bovine serum and 1 μg/ml of soluble ECD$^{HER2}$ protein. The well contents were incubated in a 5% $CO_2$, 37° C. incubator. After 84 hours, the wells were pulsed with 5 μCi of $^3$H-thymidine to a final concentration of approximately 5 μCi/ml for 12 hours (for a total stimulation period of 96 hours). Cells from a single well of the 24-well tissue culture plate were transferred to a 96-well round bottom tissue culture plate in quadruplicate and harvested. Any $^3$H-thymidine incorporation into DNA was measured as described above. Data herein are expressed as a stimulation index (SI) which is defined as the mean $^3$H CPM of the experimental wells divided by the mean $^3$H CPM of the control wells (splenocytes of mice vaccinated with PBS).

To determine the level of secreted IFN-γ, supernatants from a single well of a 24-well tissue culture plate were removed after 36 and 84 hours of stimulation and added, in duplicate, into 96-well microtiter plates that were pre-coated with an anti-IFN-γ capture antibody (PharMingen, San Diego, Calif.). The supernatants were diluted serially (1:2) and allowed to sit overnight at 4° C. The following day, the plates were washed and detecting AP-labeled antibody (PharMingen, San Diego, Calif.) was added. The plates were then allowed to sit at 37° C. for 1 hour. After washing, p-nitrophenyl phosphate disodium dissolved in diethanolamine buffer (Sigma Chemical, St. Louis, Mo.) was added to the wells and the plates were read at 410 nm. Quantitation of results was performed using a IFN-γ (PharMingen, San Diego, Calif.) standard curve generated in each plate. Data from such readings are presented as the concentration of IFN-γ (pg/ml) minus the background (PBS control) levels.

Statistical Analysis

All statistical analyses in the current example were made using the Mann-Whitney Rank Test, except for the survival curve for which the Trend Peto-Peto-Wilcoxon Test was used. For all cases, results were regarded as significant if the p values were ≦0.05.

Results for Example I

ECD$^{HER2}$ Vaccination and Anti-Tumor Activity

BALB/c mice were vaccinated subcutaneously on week 0 and week 5 with either PBS, ECD$^{HER2}$ alone, ECD$^{HER2}$ plus IgG3 or ECD$^{HER2}$ plus either IgG3-(GMCSF), IgG3-(IL-2) or IgG3-(IL-12) (as described above). No apparent side effects were observed throughout the duration of the vaccination. Eight weeks after the initial vaccination, $10^6$ TUBO cells were injected subcutaneously into the left flank of vaccinated mice. At 7 days post-challenge, measurable tumors were present in all mice vaccinated with PBS, ECD$^{HER2}$ alone and ECD$^{HER2}$ plus IgG3, while two out of eight mice in the ECD$^{HER2}$ plus IgG3-(GMCSF) or ECD$^{HER2}$ plus IgG3-(IL-12) group of vaccinated mice and five out of seven mice in the ECD$^{HER2}$ plus IgG3-(IL-2) vaccinated mice showed no tumors. See, FIG. 3a. Tumors grew uniformly and progressively in all PBS treated mice whereas mice vaccinated with $ECD^{HER2}$ alone and $ECD^{HER2}$ plus IgG3 showed dispersions in the sizes of tumors. The tumors in mice vaccinated with $ECD^{HER2}$ plus antibody-immunostimulant fusion proteins remained smaller or absent in those days indicated. See FIG. 3a.

Figure 3A:
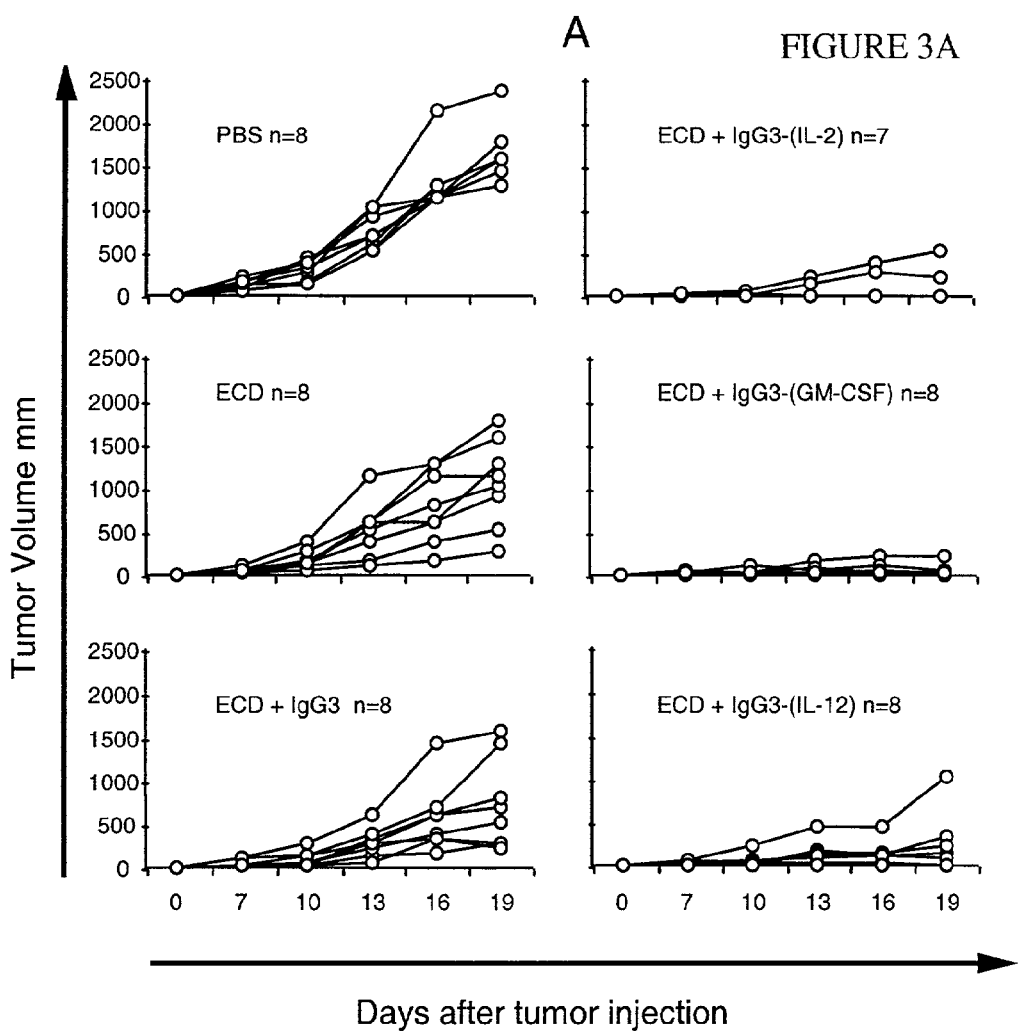
FIG. 3A-3C: Illustration of anti-tumor activity of exemplary fusion proteins/antigenic vaccination treatments of the invention in vaccinated mice challenged with TUBO.
Figure 3B:
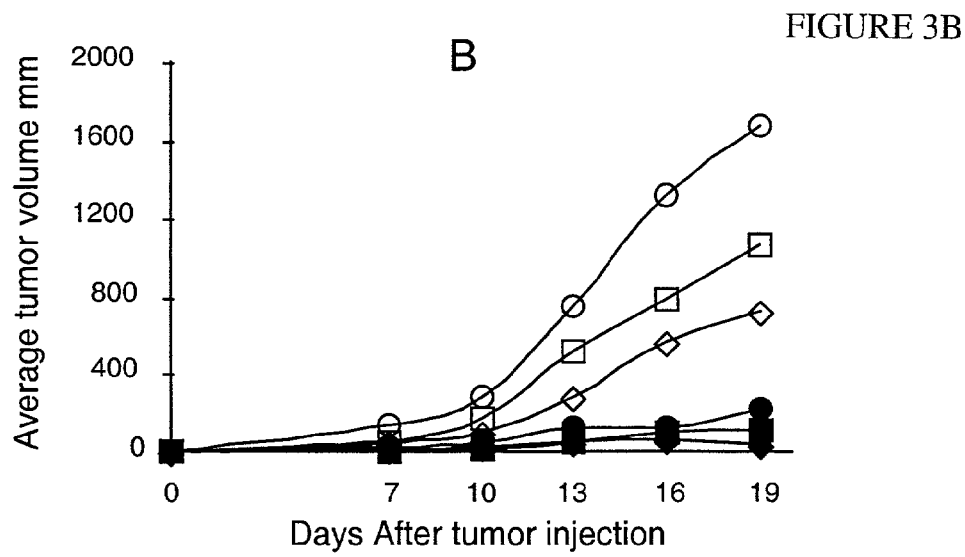
Figure 3C:
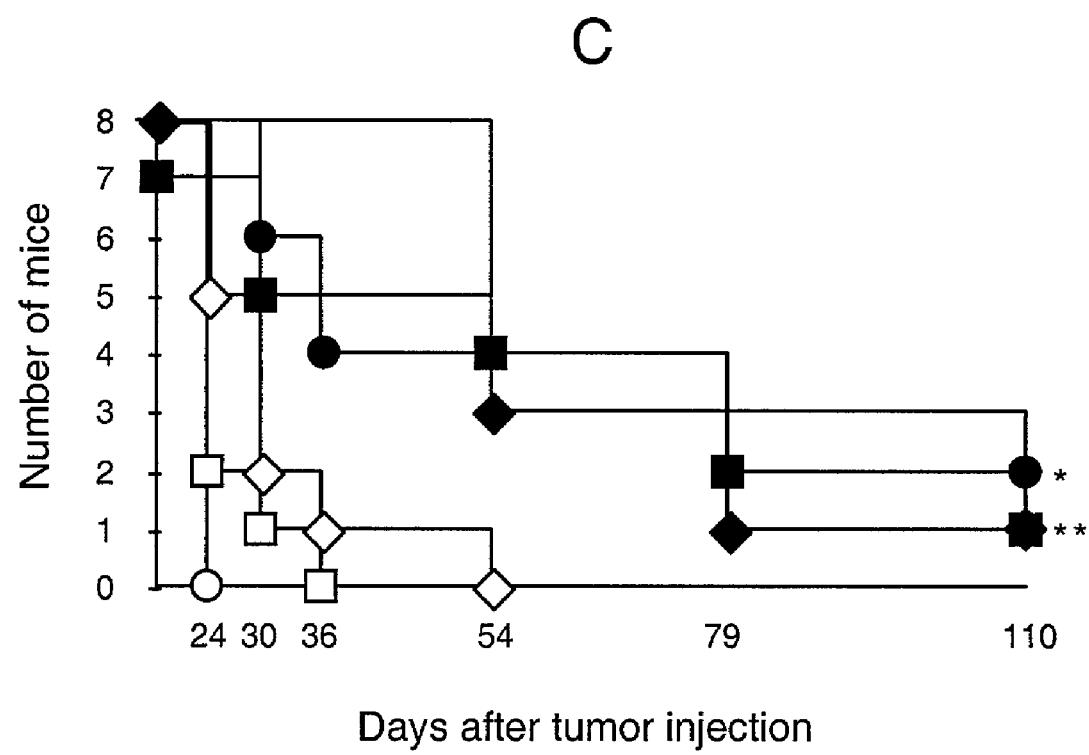

FIG. 3 displays tumor growth in vaccinated mice challenged with TUBO. As described above, groups of eight female BALB/c mice were vaccinated subcutaneously on day −56 and again on day −21 with either PBS (see, ○ in FIG. 3), $ECD^{HER2}$ protein alone (see, □ in FIG. 3), $ECD^{HER2}$ plus IgG3 (see, ◇ in FIG. 3), $ECD^{HER2}$ plus IgG3-(GMCSF) (see, ◆ in FIG. 3), $ECD^{HER2}$ plus IgG3-(IL-2) (see, ■ in FIG. 3) or ECD HER2 plus IgG3-(IL-12) (see, ● in FIG. 3). Again, as described above, on day 0, $10^6$ TUBO cells were injected subcutaneously in the left flank of the mice. The average tumor size of either individual (FIG. 3A) or average (FIG. 3B) were measured starting on day 7 and every three days until day 19. FIG. 3C shows a survival curve of the mice. Mice with tumors exceeding 1.5 cm in diameter at the time of inspection were euthanized and considered to have not survived the challenge. Mice free of tumors at day 110 are indicated by (*).

At day 19, smaller tumors (p<0.02) were apparent in $ECD^{HER2}$ alone and $ECD^{HER2}$ plus IgG3 vaccinated mice as compared to the PBS control. See, FIG. 3b. Tumor size was significantly smaller in those mice vaccinated with $ECD^{HER2}$ plus IgG3-(GMCSF) or mice vaccinated with $ECD^{HER2}$ plus IgG3-(IL-2) in all the days indicated (p≦0.05 as compared to the PBS, $ECD^{HER2}$ alone or $ECD^{HER2}$ plus IgG3 vaccinated mice). See, FIG. 3B. While the average size of tumors of mice vaccinated with $ECD^{HER2}$ plus IgG3-(IL-12) was smaller than those mice vaccinated with PBS, $ECD^{HER2}$ alone, or $ECD^{HER2}$ plus IgG3, significantly smaller tumors were present only on days 13, 16 and 19 (p<0.05). See, FIG. 3B.

Again, mice bearing tumors greater than 1.5 cm in diameter at the time of inspection were euthanized and considered to have not survived the challenge with TUBO. A survival curve, taking this into consideration, shows the superiority of vaccination regimens in which $ECD^{HER2}$ is combined with antibody-immunostimulant fusion proteins (p<0.05, compared to $ECD^{HER2}$ alone or $ECD^{HER2}$ plus IgG3 vaccinated mice). See, FIG. 3C. No significant difference was observed between the $ECD^{HER2}$ plus IgG3 and the mice vaccinated with $ECD^{HER2}$ alone (p=0.20). At 110 days post-challenge, one out of eight mice vaccinated with $ECD^{HER2}$ plus IgG3-(GMCSF) or $ECD^{HER2}$ plus IgG3-(IL-2) and two out of eight mice vaccinated with $ECD^{HER2}$ plus IgG3-(IL-12) showed no tumor development. See, FIG. 3c (indicated by asterisks).

Susceptibility of SK-BR-3 Cells (But not TUBO Cells) to Murine Anti-$ECD^{HER2}$ Mediated Tumor Growth Inhibition In Vitro An in vitro proliferation assay was performed to investigate the susceptibility of TUBO cells and SK-BR-3 cells to anti-$ECD^{HER2}$ antibody mediated tumor growth inhibition. No cell growth inhibition was detected when TUBO cells were incubated with the immune sera of vaccinated mice. See, FIG. 4a. With SK-BR-3 cells, immune sera exhibited significant anti-proliferative activity (see, FIG. 4b). As can be seen in FIG. 5, the level of cell growth inhibition correlated with the level of anti-$ECD^{HER2}$ IgG. Immune sera from the mice vaccinated with $ECD^{HER2}$ plus IgG3-(GMCSF) and $ECD^{HER2}$ plus IgG3-(IL-2) exhibited increased growth inhibition, while immune sera of mice vaccinated with $ECD^{HER2}$ plus IgG3-(IL-12) elicited modest inhibition which was still greater than the inhibition in the mice vaccinated with $ECD^{HER2}$ plus IgG3 and $ECD^{HER2}$ alone at the lower sera dilution.

Figure 4:
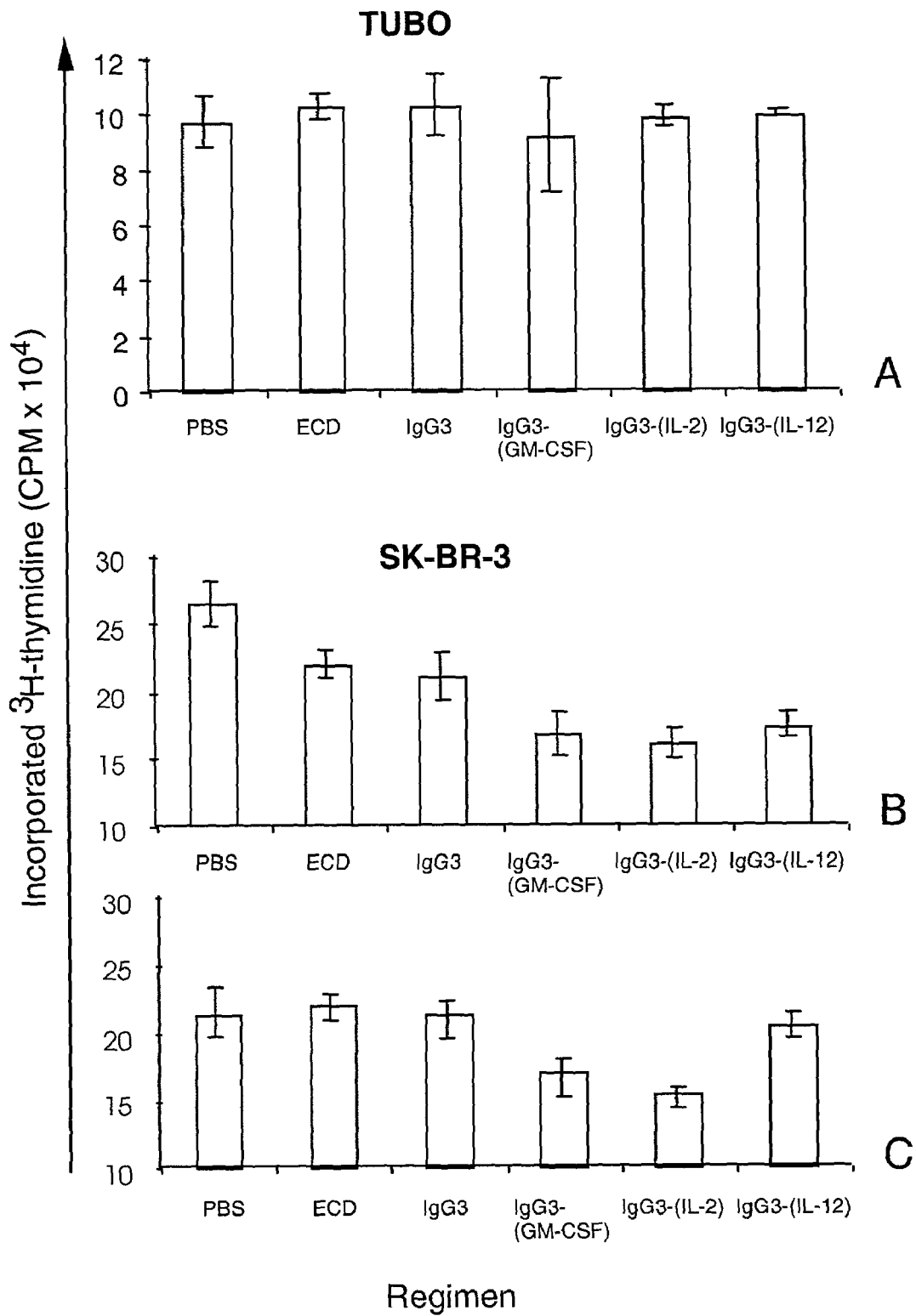
FIG. 4, Panels A-C: Illustration of the influence of sera on the in vitro proliferation of TUBO and SK-BR-3 cells.
Figure 5:
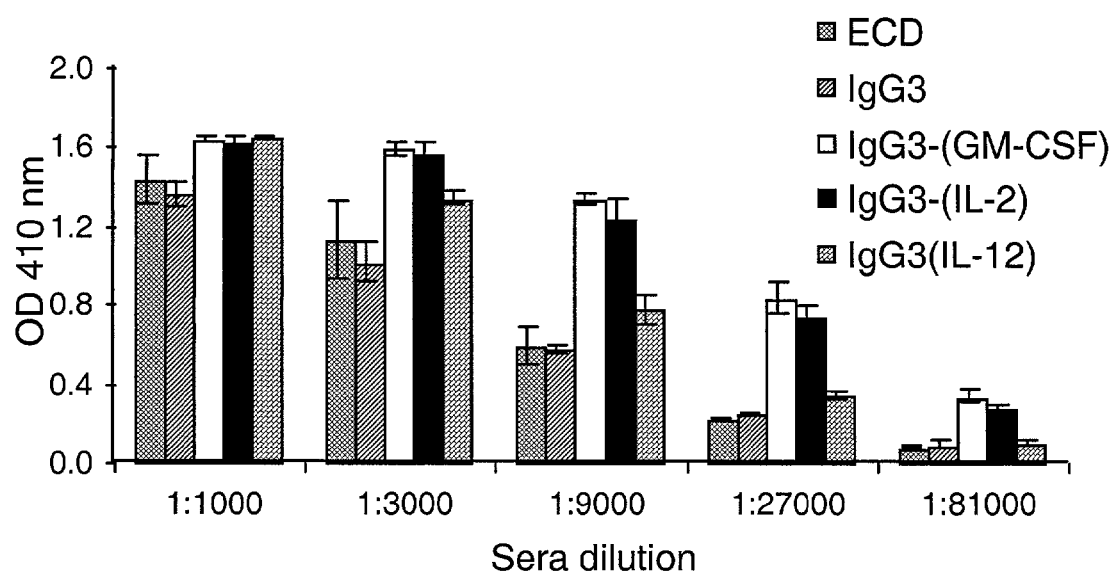
FIG. 5: Illustration of murine anti-ECD$^{HER2}$ antibody response in vaccinated mice.

FIG. 4 illustrates the influence of sera on the in vitro proliferation of TUBO cells and SK-BR-3 cells. TUBO or SK-BR-3 cells were incubated with complement-inactivated pooled immune sera obtained from vaccinated mice two days prior to the challenge with TUBO cells. The wells were pulsed with $^3$H-thymidine 12 hours prior to the end of the incubation. The data in FIG. 4A represent the $^3$H-thymidine (CPM) incorporated by the TUBO cells after 48 hours of incubation with the immune sera, diluted 1:100, and the data in FIG. 4B represent the level of $^3$H-thymidine (CPM) incorporated into the SK-BR-3 cells when incubated with immune sera diluted at 1:100 and at 1:300 (FIG. 4c). The error bars represent the range of values obtained.

FIG. 5 illustrates a murine anti-$ECD^{HER2}$ antibody response. Blood samples from vaccinated mice taken two days prior to a challenge with TUBO cells were collected and the sera was pooled. The pooled sera were examined for anti-$ECD^{HER2}$ IgG levels by ELISA. PBS control wells showed undetectable levels of anti-$ECD^{HER2}$ IgG and were used as blanks. Values in FIG. 5 represent the average intensity at $OD_{410\ nm}$ of duplicate wells at the indicated serum dilution. The error bars represent the range of duplicate values.

Passive Transfer of Immune Sera

The inability of anti-$ECD^{HER2}$ antibodies to inhibit the growth of TUBO cells in vitro suggested that perhaps an in vivo environment may be necessary to elicit an effective anti-tumor response against the TUBO cells. To examine this possibility, naïve mice were injected intravenously with pooled immune sera and then challenged subcutaneously the next day with $10^6$ TUBO cells. Tumor growth was monitored and measured with a caliper beginning 7 days post-challenge, and every three days following until day 21. Mice injected with sera from mice vaccinated with PBS, $ECD^{HER2}$ alone and $ECD^{HER2}$ plus IgG3 showed no apparent anti-tumor activity throughout the duration of the experiment. See, Table I, below. As compared to the untreated mice, smaller average size of tumors was observed in mice vaccinated with $ECD^{HER2}$ plus antibody-fusion proteins at the days indicated. However, only at day 13 were significantly smaller tumors observed in those mice injected with sera from mice vaccinated with $ECD^{HER2}$ plus IgG3-(GMCSF) (p=0.03, compared to the untreated mice). Mice injected with sera from mice vaccinated with $ECD^{HER2}$ plus IgG3-(IL-2) showed significantly smaller tumors at days 16 and 19 (p=0.03 and p=0.05 compared to the untreated mice, respectively). Mice injected with sera from mice vaccinated with $ECD^{HER2}$ plus IgG3-(IL-12) showed significantly smaller tumors at days 13, 16, 19 and 21 (p≦0.05 as compared to untreated mice). See, Table I.

TABLE I

Passive transfer of immunity[a].

| Groups | Average Tumor size (mm$^3$) | | | | | |
|---|---|---|---|---|---|---|
| | Day 7 | Day 10 | Day 13 | Day 16 | Day 19 | Day 21 |
| Control | 51 | 219 | 439 | 771 | 1045 | 1581 |
| PBS | 50 | 184 | 452 | 589 | 983 | 1468 |
| ECD | 93 | 160 | 451 | 595 | 932 | 1681 |
| IgG3 | 54 | 316 | 432 | 699 | 1242 | 1604 |
| IgG3- (GM-CSF) | 52 | 140 | 233 | 510 | 897 | 1077 |

TABLE I-continued

Passive transfer of immunity[a].

| Groups | Average Tumor size (mm³) | | | | | |
|---|---|---|---|---|---|---|
| | Day 7 | Day 10 | Day 13 | Day 16 | Day 19 | Day 21 |
| IgG3-(IL-2) | 39 | 150 | 261 | 381 | 605 | 977 |
| IgG3-(IL-12) | 19 | 135 | 161 | 389 | 489 | 804 |

[a]Groups of 6 female BALB/c mice were injected i.v. with 175 µl of pooled immune sera. The following day, day 0, 10⁶ TUBO cells were injected s.c. in the right flank. Tumor growth was examined and measured beginning on day 7 and every three days until day 21. Underlined-bold values indicate the average tumor size of mice in each group with p values ≦ 0.05 as compared to the average tumor size of untreated mice.

Characterization of Anti-ECD$^{HER2}$ Antibodies of Transferred Immune Sera

Figure 6:
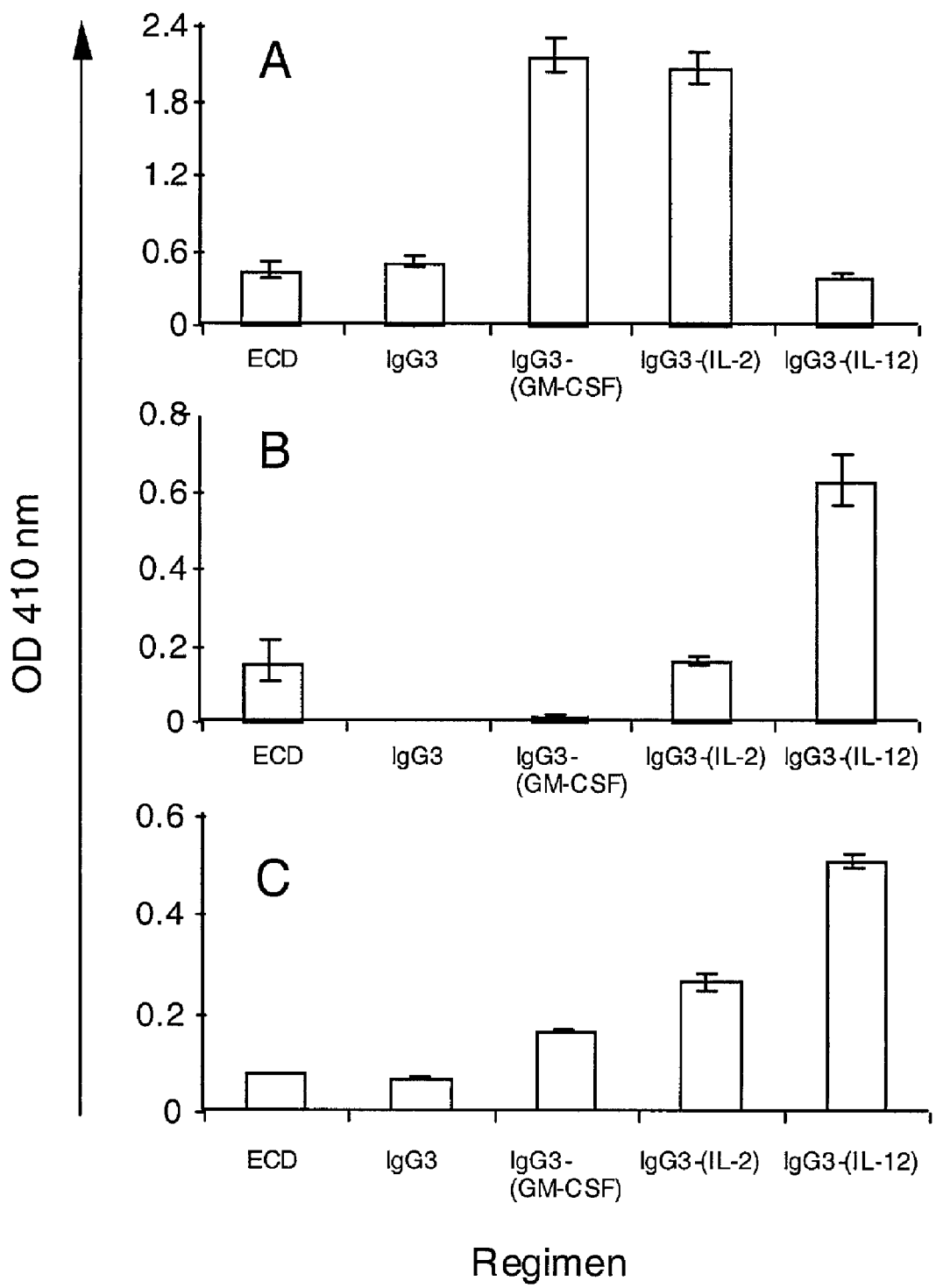
FIG. 6, Panels A-C: Characterization of anti-ECD$^{HER2}$ IgG of transferred immune sera of vaccinated mice.

Transferred immune sera were analyzed for the levels of anti-ECD$^{HER2}$ IgG1, IgG2a and IgG3. Pooled serum of mice vaccinated with ECD$^{HER2}$ plus IgG3-(GMCSF) and ECD$^{HER2}$ plus IgG3-(IL-2) showed higher levels of anti-ECD$^{HER2}$ IgG1 as compared to pooled serum of mice vaccinated with ECD$^{HER2}$ plus IgG3-(IL-12), ECD plus IgG3 or ECD$^{HER2}$ alone. See, FIG. 6a. In contrast, the anti-ECD$^{HER2}$ IgG2a response was markedly higher in pooled serum of mice vaccinated with ECD$^{HER2}$ plus IgG3-(IL-12), while a modest response was seen in mice vaccinated with ECD$^{HER2}$ plus IgG3-(IL-2) and lesser levels in ECD$^{HER2}$ plus IgG3-(GMCSF). See, FIG. 6b. Substantial anti-ECD$^{HER2}$ IgG2a levels were detected in the pooled serum of mice vaccinated with ECD$^{HER2}$ alone comparable to mice vaccinated with ECD$^{HER2}$ plus IgG3-(IL-2), while little to no anti-ECD$^{HER2}$ IgG2a was detected in mice vaccinated with ECD$^{HER2}$ plus IgG3. Analysis of serum of individual mice revealed that one overreacting mouse (out of eight of the mice vaccinated with ECD$^{HER2}$ alone) exhibited a detectable anti-ECD$^{HER2}$ IgG2a response. Little to no detectable anti-ECD$^{HER2}$ IgG2a response was detected in the other seven mice. See, Table II. Anti-ECD$^{HER2}$ IgG3 levels were similar to anti-ECD$^{HER2}$ IgG2a levels, however, no increased level of anti-ECD$^{HER2}$ IgG3 was observed in pooled serum of mice vaccinated with ECD$^{HER2}$ alone as compared to pooled serum of mice vaccinated with ECD$^{HER2}$ plus IgG3. See, FIG. 6c.

TABLE II

Murine anti-F ECD$^{HER2}$ IgG2a titers[a].

| Mouse No. | PBS | ECD | IgG3 | IgG3-(GMCSF) | IgG3-(IL-2) | IgG3-(IL-12) |
|---|---|---|---|---|---|---|
| 1 | 0[b] | 0[b] | 0[b] | 200 | 200 | 800 |
| 2 | 0[b] | 8100 | 0[b] | 100 | 0[b] | 800 |
| 3 | 0[b] | 0[b] | 0[b] | 200 | 3200 | 800 |
| 4 | 0[b] | 0[b] | 0[b] | 200 | 100 | 6400 |
| 5 | 0[b] | 0[b] | 0[b] | 100 | 100 | 6400 |
| 6 | 0[b] | 0[b] | 0[b] | 100 | 100 | 1600 |
| 7 | 0[b] | 0[b] | 0[b] | 100 | 800 | 800 |
| 8 | 0[b] | 0[b] | 0[b] | 100 | 200 | 800 |
| Average: | 0 | 1013 | 0 | 175 | 586 | 2300 |

[a]Groups of eight female BALB/c mice were injected s.c. in the right flank with either PBS, ECD$^{HER2}$ alone, ECD$^{HER2}$ plus IgG3, ECD$^{HER2}$ plus IgG3-(GM-CSF), ECD$^{HER2}$ plus IgG3-(IL-2), or ECD$^{HER2}$ plus IgG3-(IL-12), at week 0 and again at week 5. At week 8, blood samples were collected and sera from individual mice were examined for anti-ECD$^{HER2}$ IgG2a titers by ELISA. Values represent the average of duplicate dilutions of serum required to yield an absorbance OD$_{410\,nm}$ ≧ 0.05 after 2 hr of incubation.
[b]Absorbance at OD$_{410\,nm}$ < 0.05 at 1:50 initial sera dilution.

As explained above, FIG. 6 illustrates the characterization of anti-ECD$^{HER2}$ IgG of transferred immune sera. Transferred pooled serum from vaccinated mice was examined for anti-ECD$^{HER2}$ IgG1 (see, FIG. 6a), IgG2a (see, FIG. 6b), and IgG3 (see, FIG. 6c) levels by ELISA. Values represent the average intensity at OD$_{410\,nm}$ of duplicate wells at 1:1000, 1:50, and 1:50 serum dilution, respectively. PBS control wells were used as blanks. The error bars represent the range of duplicate values.

In Vitro Stimulation of Splenocytes from Vaccinated Mice by ECD$^{HER2}$ Protein To determine the cellular immune response elicited in vaccinated mice, the ability of splenocytes to proliferate following incubation with soluble ECD$^{HER2}$ protein in vitro was assessed. Proliferation was measured by ³H-thymidine incorporation into DNA. After 48 hours of incubation, significant proliferation was detected in splenocytes from the mice vaccinated with ECD$^{HER2}$ plus IgG3-(GMCSF) with less proliferation seen with splenocytes from mice vaccinated with ECD$^{HER2}$ plus IgG3-(IL-2). Very modest stimulation was observed when the splenocytes were from mice vaccinated with ECD$^{HER2}$ plus IgG3-(IL-12), ECD$^{HER2}$ alone or ECD$^{HER2}$ plus IgG3. See, FIG. 7a. Similar results were observed after 96 hours of incubation with the soluble ECD$^{HER2}$ protein. See, FIG. 7b.

Figure 7:
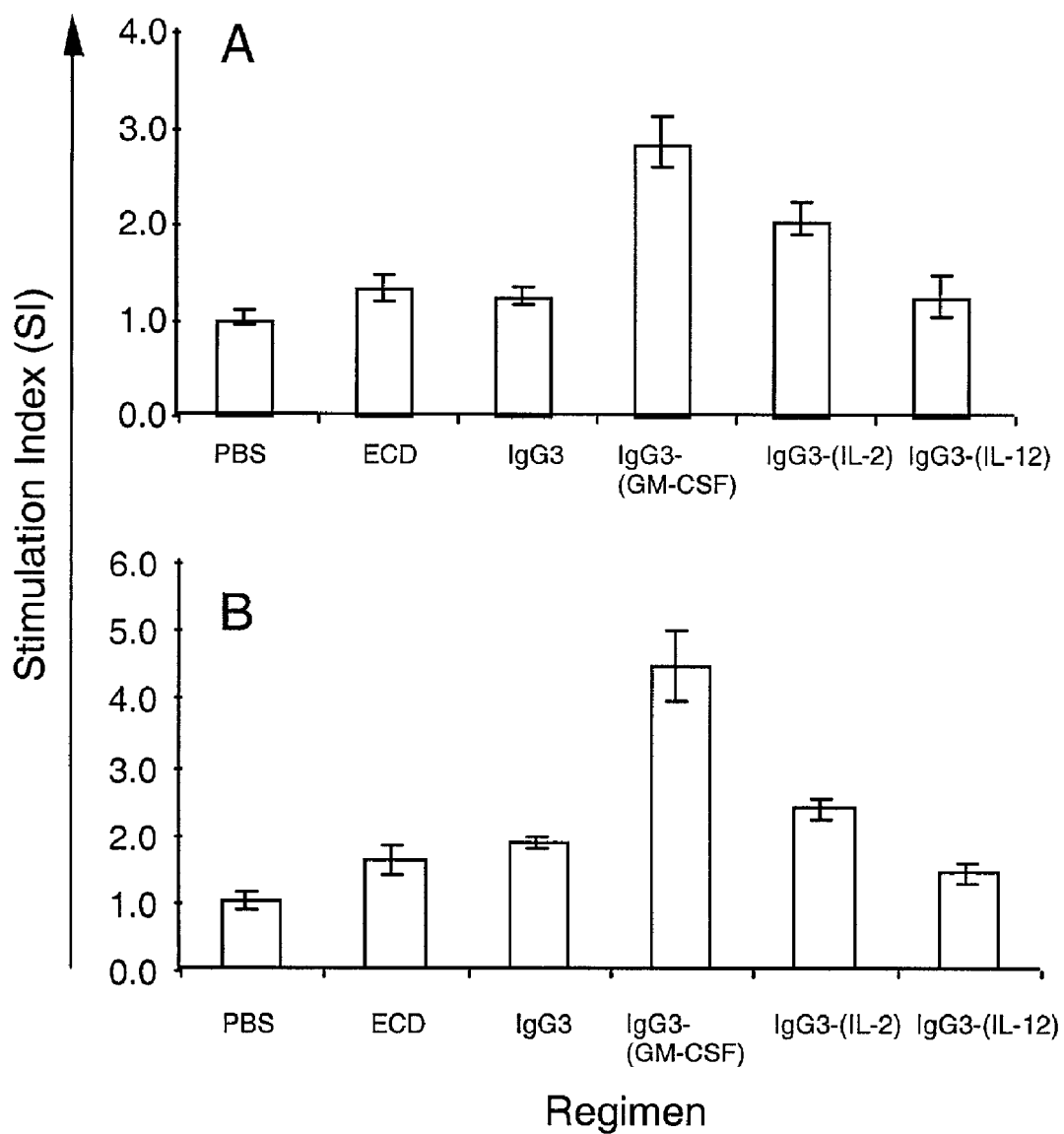
FIG. 7, Panels A-B: In vitro stimulation of proliferation of splenocytes of vaccinated mice by ECD$^{HER2}$ protein.

FIG. 7 displays in vitro stimulation of splenocyte proliferation by ECD$^{HER2}$ protein. Pooled splenocytes from vaccinated mice were incubated with soluble ECD$^{HER2}$ in a 24-well tissue culture plate and pulsed with ³H-thymidine 12 hours prior to the end of the incubation periods (i.e., 48 hours, as seen in FIG. 7a or 96 hours, as seen in FIG. 7b). Cells from a single well of a 24-well tissue culture plate were transferred to a 96-well round bottom tissue culture plate in quadruplicate and collected with a cell harvester. Incorporated ³H-thymidine (CPM) was measured using a scintillation counter. The data in FIG. 7 are expressed as a stimulation index (SI) (as defined above). The error bars represent the range of values obtained from the four determinations.

IFN-γ Production of Stimulated Splenocytes

The supernatants of splenocytes incubated with the soluble ECD$^{HER2}$ protein were examined for the levels of the $T_H1$ or $T_H2$ cytokines, IFN-γ and IL-4. See, e.g., Arai, K. I., et al. 1990 "Cytokines: coordinators of immune and inflammatory responses" *Annu Rev Biochem* 59:783+. After a stimulation period of 36 hours, increased IFN-γ production was detected in the supernatants of splenocytes from vaccinated mice compared to the PBS control with the level as follows: ECD$^{HER2}$ plus IgG3-(GMCSF)>ECD$^{HER2}$ plus IgG3-(IL-2)>ECD$^{HER2}$ plus IgG3-(IL-12)>ECD$^{HER2}$ plus IgG3>ECD$^{HER2}$ alone. See, FIG. 8a. No IFN-γ could be detected when splenocytes from mice treated with PBS were used. After 84 hours of stimulation, enhanced IFN-γ production was detected in the supernatant of splenocytes from mice vaccinated with ECD$^{HER2}$ plus IgG3-(GMCSF). The production peaked at approximately 1,500 pg/ml. See, FIG. 8b. A modest increase in IFN-γ was observed in the supernatants of mice vaccinated with ECD$^{HER2}$ plus IgG3-(IL-2), while little to no increase was seen in the supernatants of splenocytes from mice vaccinated with ECD$^{HER2}$ plus IgG3-(IL-12), ECD$^{HER2}$ alone or ECD$^{HER2}$ plus IgG3. See, FIG. 6b. After 36 hours the IL-4 level in all supernatant was below the sensitivity of the assay (<30 pg/ml, data not shown). After 84 hours however, low IL-4 levels could be measured only in the supernatant of splenocytes from mice vaccinated with ECD$^{HER2}$ plus IgG3-(GMCSF) (36 pg/ml).

Figure 8:
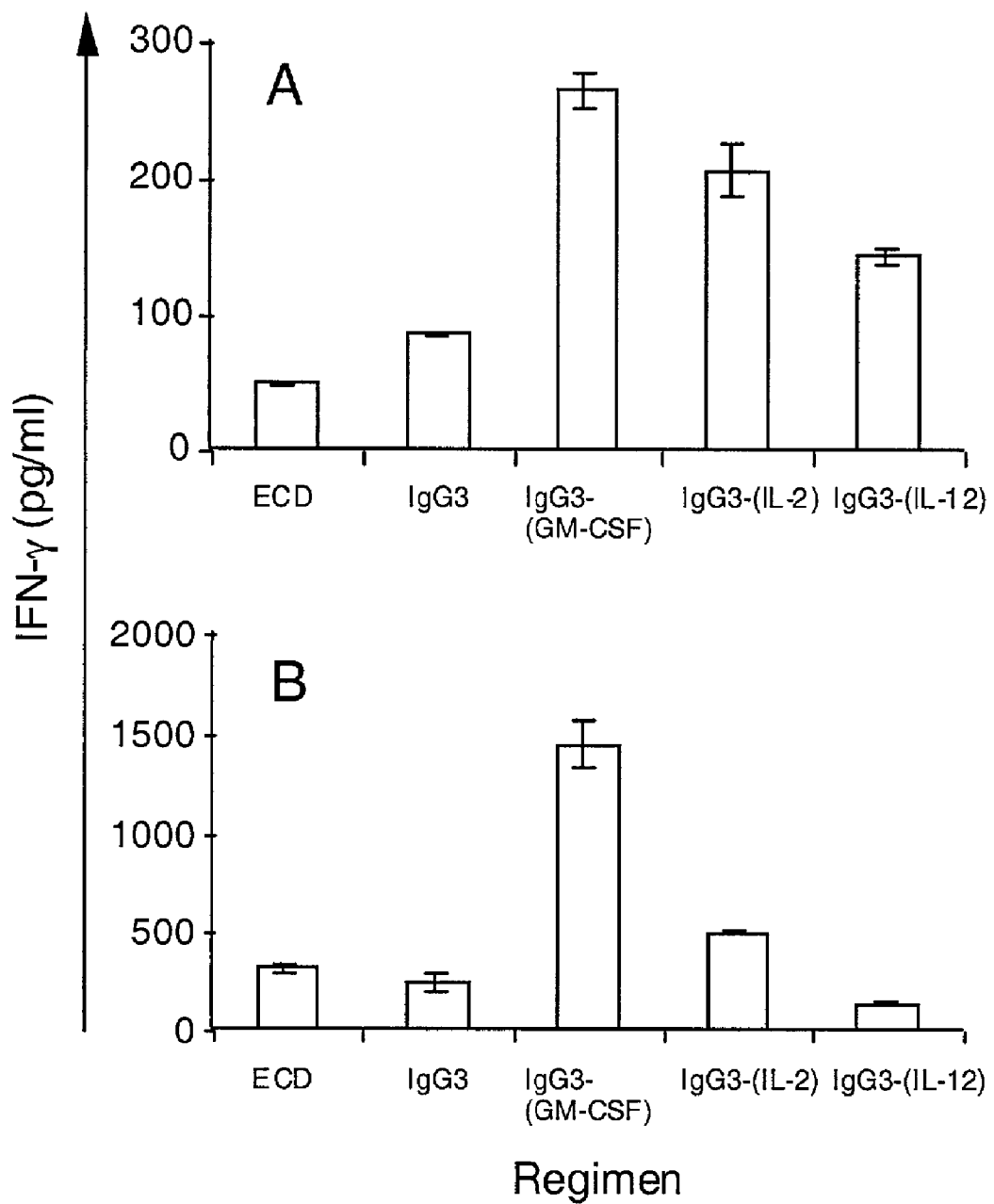
FIG. 8, Panels A-B: In vitro IFN-γ production by stimulated splenocytes from vaccinated mice.

FIG. 8 displays the in vitro IFN-γ production by stimulated splenocytes from vaccinated mice. Supernatants from splenocytes of vaccinated mice were harvested after either 36 hours (FIG. 8a) or 84 hours (FIG. 8b) of incubation with soluble ECD$^{HER2}$, and the level of IFN-γ secretion was quantified using a sandwich ELISA. A standard curve was generated in each plate and data was presented as the concentration of IFN-γ (pg/ml) minus the background (PBS control) levels. The error bars represent the range of duplicate values.

Example II

Use of Antibody-Immunostimulant Fusion Proteins to Enhance Immune Response Against *Staphylococcus aureus* Virulence Factor Protein A Protein A and Antibody-Immunostimulant Fusion Proteins As outlined above, antibody-immunostimulant (e.g., cytokine) fusion proteins specific for the extracellular domain of the human tumor associated antigen HER2/neu ($ECD^{HER2}$) were constructed and their action characterized. Such fusion proteins were composed of human IgG3 (containing the variable region of Trastuzumab (Herceptin, Genentech, San Francisco, Calif.)) which was genetically fused to the immunostimulatory cytokines interleukin-2 (IL-2), interleukin-12 (IL-12), or granulocyte-macrophage colony stimulator factor (GMCSF). See, Penichet, M. L. and Morrison, S. L. 2001, "Antibody-cytokine fusion proteins for the therapy of cancer" *J Immunol Methods* 248: 91-101; Peng, L. S., et al. 1999, "A single-chain IL-12 IgG3 antibody fusion protein retains antibody specificity and IL-12 bioactivity and demonstrates antitumor activity" *J Immunol* 163: 250-8; and Dela Cruz, J. S., et al. 2000, "Recombinant anti-human HER2/neu IgG3-(GMCSF) fusion protein retains antigen specificity, cytokine function and demonstrates anti-tumor activity" *J Immunol* 165: 5112-21.

During the work done characterizing anti-HER2/neu fusion proteins (i.e., see above) it was found that antibodies containing the variable regions of Herceptin would bind protein A. This observation was surprising since, by contrast with other isotypes, human IgG3 does not bind protein A. It was shown that such binding occurred through the variable region of the antibodies (Penichet et al., unpublished results). This finding was consistent with a recent report describing the Herceptin variable region as encoded by the $V_H3$ gene family (see, Meininger, D. P., et al. 2000 "Characterization of the binding interface between the E-domain of Staphylococcal protein A and an antibody Fv-fragment" *Biochemistry* 39: 26-36).

As stated above, antibodies with $V_H3$ regions bind to protein A through the "frame-work" of their variable regions. However, it must be noted that the protein A binding site is separated from the classical Fc binding site (see, Tashiro M., et al. 1995, "Structures of bacterial immunoglobulin-binding domains and their complexes with immunoglobulins" *Curr Opin Struct Biol* 4: 471-81; Vidal M. A., et al. 1985 "Alternative mechanism of protein A-immunoglobulin interaction the $V_H$-associated reactivity of a monoclonal human IgM" *J Immunol* 135: 1232-8; Graille M., et al. 2000, "Crystal structure of a *Staphylococcus aureus* protein A domain complexed with the Fab fragment of a human IgM antibody: structural basis for recognition of B-cell receptors and superantigen activity" *Proc Natl Acad Sci USA* 97: 5399-404). Thus, the anti-HER2/neu fusion proteins developed (e.g., those illustrated in Example I) also act as a family of "anti-protein A" fusion proteins.

The ability to bind soluble protein A through use of the two of the antibody fusion proteins (i.e., anti-HER2/neu IgG3-(IL-2) and anti-HER2/neu IgG3-(GMCSF) as utilized in Example I) was used to explore if such antibody-immunostimulant fusion proteins where able to enhance the immunogenicity of the protein A bacterial antigen.

Materials and Methods

Mice

Female BALB/c mice (6-8 weeks old) were purchased from Taconic Farms (Germantown, N.Y.). A group of mice were subcutaneously injected with soluble protein A either with or without the presence of antibody or antibody-immunostimulant fusion proteins. An additional group of mice were injected with PBS alone as a control. Each group contained a total of 8 mice per group.

Vaccination with Soluble Protein A

5 μg of soluble protein A (P4931, Sigma. St. Louis, Mo.) was incubated in 1×PBS (phosphate buffered saline) overnight at 4° C. with either 20 μg of anti-HER2/neu IgG3 (the antibody alone, without a fused immunostimulant), anti-HER2/neu IgG3-(GMCSF) or anti-HER2/neu IgG3-(IL-2) at an antibody molar ratio equivalent to 20 μg of IgG3. The following day samples of the mixtures were injected subcutaneously in the right flanks of the mice. A booster was given to each mouse during week 5 in the same flank.

Preparation of Serum for Enzyme Linked ImmunoSorbant Assay (ELISA) Assays

After immunization, the mice were bled every week for 8 weeks. The blood was collected and stored at 4° C. overnight. The following day the serum was collected and stored at −20° C. The sera of all of the mice in each group were pooled and diluted 1:150 to be used for serological studies.

Serological Studies Using ELISA

An ELISA was used to examine the level of any antibody response to soluble protein A and Cowan I (a standard strain of *Staphylococcus aureus* which expresses the insoluble surface protein, protein A) that was generated in the mice.

A solution of 10% m/v formalin-killed Cowan I (P7155, Sigma) was diluted in carbonate buffer (at approximately a 1:235 dilution) to give an $OD_{650\,nm}$ of 0.1. This was added to a 96 well plate (Immulon-2, Dyntex Technologies, Chantilly, Va.) at 50 μl per well and incubated overnight at 4° C. Protein A (P3838, Sigma. St. Louis, Mo.) was diluted in carbonate buffer to give a final concentration of 1 μg/ml. The diluted protein A was added to the 96 well plate at 50 μl per well, and incubated overnight at 4° C. A solution of 3% rabbit serum in PBS was used as a diluent and as a blocking solution to prevent the binding of murine antibodies to protein A through the Fc or Fab regions of the antibodies. It has previously been found that an incubation with 3% rabbit serum in PBS is extremely efficient in blocking the binding of murine antibodies to protein A through Fc or Fab regions (Penichet et al. unpublished results). Because of the blocking, the antibody binding detected in the current example is specific for different epitopes of protein A. The collected mouse serum was diluted 1:450 in 1% BSA (bovine serum albumin) in PBS and added to each well at a volume of 50 μl, followed by 1:2 serial dilutions. Pooled anti-sera showing a high antibody titer to insoluble protein A immobilized on Cowan I and to soluble protein A was diluted 1:1350 in 1% BSA in PBS and used as a positive control. An alkaline phosphatase (AP) labeled goat anti-murine IgG diluted 1:20,000 was used to detect bound murine IgG. The 96-well plates were washed 4 times with PBS and AP-substrate (dissolved in diethanolamine buffer) was added to the plates at a volume of 50 μl per well. The sera of mice vaccinated with PBS alone were included as a control and used as a blank to measure the absorbance at 410 nm.

Results

Figure 9:
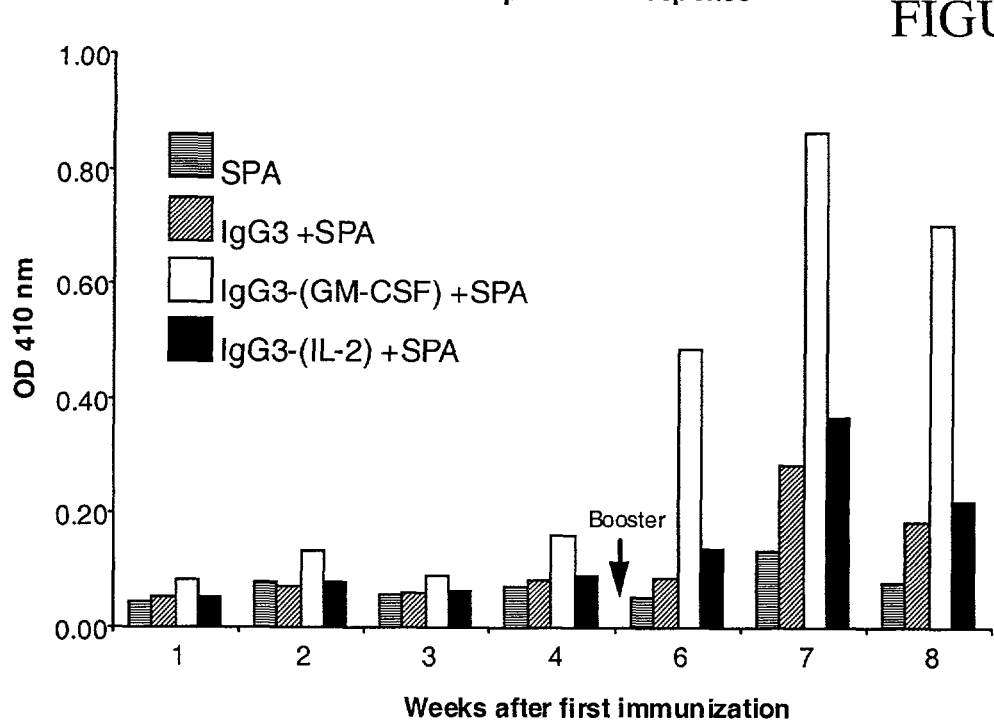
FIG. 9: Illustration of murine anti-protein A antibody response in vaccinated mice.

Detection of Antibody Immune Response Using Plates Coated with Soluble Protein A As illustrated in FIG. 9, sera from mice vaccinated with soluble protein A (SPA) in PBS or with IgG3, IgG3-(GMCSF) and IgG3-(IL-2) were collected and pooled weekly for 8 weeks after immunization. The samples were assayed (in duplicate) for anti-protein A response using ELISA with plates coated with soluble protein A. A negative control group consisting of mice given PBS alone, was included and used as a blank. The data in FIG. 9 is presented as the average $OD_{410}$ of duplicate wells. The booster (given 5 weeks after the first vaccination) is indicated by the arrow.

As can be seen in FIG. 9, both the IgG3 and the IgG3-(IL-2) groups did not show an enhanced antibody response to protein A as compared to the PBS group before booster. On the other hand, the IgG3-(GMCSF) group showed an enhanced anti-protein A response. After the booster was given, the IgG3, IgG3-(GMCSF), and IgG3-(IL-2) groups were able to generate enhanced anti-protein A response as compared with the PBS group. Furthermore, after the booster was given, the IgG3-(GMCSF) group generated the greatest enhancement of anti-protein A response as compared to both IgG3 and IgG3-(IL-2) groups.

Detection of Antibody Immune Response Using Plates Coated with Protein A Expressing Cowan I.

Figure 10:
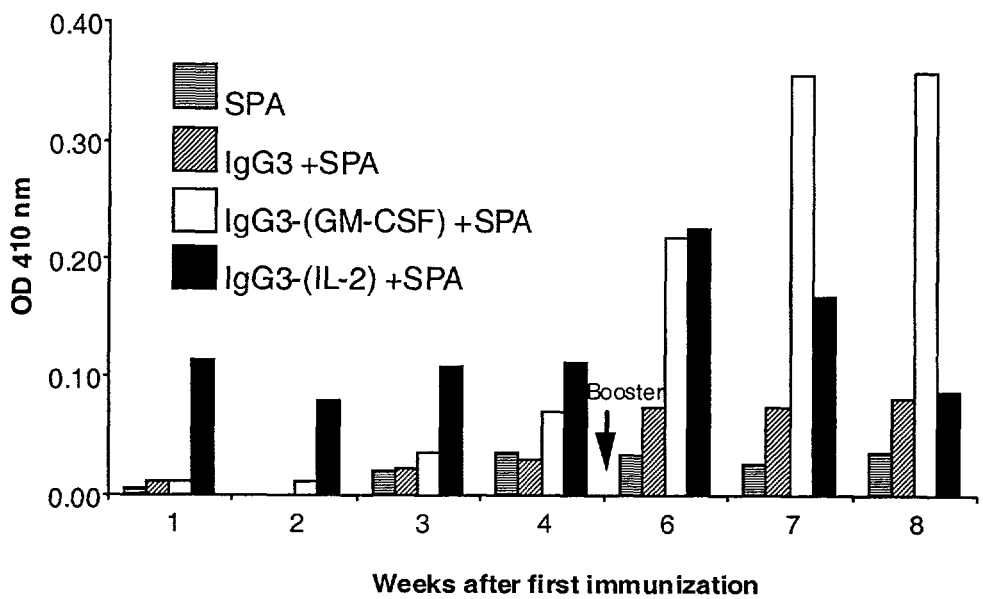
FIG. 10: Illustration of murine anti-protein A (bound on Cowan I) antibody response in vaccinated mice.

Sera from mice vaccinated with soluble protein A (SPA) in PBS or with IgG3, IgG3-(GMCSF) and IgG3-(IL-2) were collected and pooled weekly for 8 weeks after immunization. Using with plates coated with Cowan I, the samples were ELISA-assayed in duplicate for indication of an anti-protein A response (protein A being bound on the surface of Cowan I). A negative control group consisting of mice given PBS alone, was included and used as a blank. The data in FIG. 10 is presented as the average $OD_{410}$ of duplicate wells. A booster was given 5 weeks after the first vaccination (indicated by arrow). As illustrated in FIG. 10, only the IgG3-(IL-2) group generated an enhanced anti-protein A response (protein A being bound on the surface Cowan I) in the weeks before booster. No dramatic change in the later response was observed in the weeks after the booster was given. After the booster was given, the IgG3, IgG3-(GMCSF) and IgG3-(IL-2) groups showed response as compared with the PBS group. Furthermore the IgG3-(GMCSF) group generated the greatest enhancement of response after the booster, as compared to both IgG3 and IgG3-(IL-2) groups.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. An ex vivo pharmaceutical composition comprising: an antibody-immunostimulant fusion protein having an antibody domain and an immunostimulant domain, a disease-related antigen, one or more antigen presenting cells, and a pharmaceutically acceptable carrier or a pharmaceutically acceptable excipient, wherein the fusion protein acts as an effective adjuvant of the disease-related antigen;

wherein the antibody-immunostimulant fusion protein comprises antibody specificity against the antigen;

wherein the antibody domain comprises an intact antibody, comprising two light chains and two heavy chains, or an antibody fragment, which fragment is selected from the group consisting of an Fab domain, an Fab' domain, an $F(ab')_2$ domain, an scFv domain, and an $F(ab)_2$ domain; and, wherein the immunostimulant domain comprises an immunostimulant selected from the group consisting of IL-2, IL-12, and GM-CSF.

2. The composition of claim 1, wherein the antibody-immunostimulant fusion protein comprises a linker.

3. The composition of claim 1, wherein the antibody domain of the antibody-immunostimulant fusion protein comprises an antibody specific for a HER2/neu antigen.

4. The composition of claim 1, wherein the antibody domain of the antibody-immunostimulant fusion protein comprises an antibody specific for a tumor antigen.

5. The composition of claim 1, wherein the antibody-immunostimulant fusion protein comprises a domain selected from the group consisting of: IgG, IgA, IgE, IgM, IgD, IgG1, IgG2, and IgG3.

6. The composition of claim 1, wherein the antigen comprises HER2/neu, HER2/neu shed from a tumor cell, or a fragment of HER2/neu or HER2/neu shed from a tumor cell.

7. The composition of claim 1, wherein the antigen comprises an antigen arising from a subject, arising from a disease state within the subject, or arising from a disease related organism within the subject.

8. The composition of claim 7, wherein the disease state within the subject is caused by a tumor.

9. The composition of claim 7, wherein the antigen comprises a tumor antigen.

10. The composition of claim 1, wherein the antigen comprises an exogenous antigen.

11. The composition of claim 10, wherein the exogenous antigen comprises an antigen substantially identical to an antigen arising from a disease state within a subject or from a disease related organism within the subject.

12. The composition of claim 1, wherein the composition comprises a plurality of the antigen and a plurality of the antibody-immunostimulant fusion protein.

13. The composition of claim 1, wherein the antigen comprises one or more antigen chosen from the group consisting of: a soluble antigen, a soluble antigen bound to a matrix, an insoluble antigen bound to a matrix, an insoluble aggregate of antigens, an antigen comprising one or more epitopes, a nonviable cell-associated antigen, a nonviable organism-associated antigen, or an antigen conjugated with a liposome.

14. The composition of claim 12, wherein the members of the plurality of the antibody-immunostimulant fusion protein are substantially saturated by members of the plurality of the antigen.

15. The composition of claim 1, wherein the immunostimulant domain comprises an immunostimulant selected from the group consisting of IL-12 and GM-CSF.

16. The composition of claim 15, wherein the antibody domain of the antibody-immunostimulant fusion protein comprises an antibody specific for a HER2/neu antigen and wherein the antigen comprises HER2/neu, HER2/neu shed from a tumor cell, or a fragment of HER2/neu or HER2/neu shed from a tumor cell.

17. An ex vivo pharmaceutical composition comprising: an antibody-immunostimulant fusion protein having an antibody domain and an immunostimulant domain, a HER2/neu antigen, one or more antigen presenting cells, and a pharmaceutically acceptable carrier or a pharmaceutically acceptable excipient, wherein the fusion protein acts as an effective adjuvant of the HER2/neu antigen;

wherein the antibody-immunostimulant fusion protein comprises antibody specificity against the HER2/neu antigen;

wherein the antibody domain comprises IgG3; and, wherein the immunostimulant domain comprises an immunostimulant selected from the group consisting of IL-2, IL-12, and GM-CSF.

18. The composition of claim 17, wherein the immunostimulant domain comprises an immunostimulant selected from the group consisting of IL-12 and GM-CSF.

19. The composition of claim 1 or claim 17, wherein the antigen presenting cell is a dendritic cell.

\* \* \* \* \*